US011523902B2

(12) United States Patent
Ekvall et al.

(10) Patent No.: US 11,523,902 B2
(45) Date of Patent: Dec. 13, 2022

(54) APPARATUS AND METHODS FOR DELIVERY, REPOSITIONING, AND RETRIEVAL OF TRANSCATHETER PROSTHETIC VALVES

(71) Applicant: Tendyne Holdings, Inc., St. Paul, MN (US)

(72) Inventors: Craig A. Ekvall, East Bethel, MN (US); Khoi Le, Edina, MN (US); John F. Otte, Minneapolis, MN (US); Zachary J. Tegels, Minneapolis, MN (US); Robert M. Vidlund, Forest Lake, MN (US)

(73) Assignee: Tendyne Holdings, Inc., St. Paul, MN (US)

( * ) Notice: Subject to any disclaimer, the term of this patent is extended or adjusted under 35 U.S.C. 154(b) by 484 days.

(21) Appl. No.: 16/856,223

(22) Filed: Apr. 23, 2020

(65) Prior Publication Data

US 2020/0246143 A1 Aug. 6, 2020

Related U.S. Application Data

(60) Division of application No. 15/730,148, filed on Oct. 11, 2017, now Pat. No. 10,667,905, which is a
(Continued)

(51) Int. Cl.
*A61F 2/24* (2006.01)
*A61M 25/01* (2006.01)
(Continued)

(52) U.S. Cl.
CPC .......... *A61F 2/2433* (2013.01); *A61F 2/2412* (2013.01); *A61F 2/2436* (2013.01);
(Continued)

(58) Field of Classification Search
CPC .... A61F 2/2433; A61F 2/2412; A61F 2/2436; A61F 2/2466; A61F 2/9522; A61M 25/0102; A61B 2017/00292
See application file for complete search history.

(56) References Cited

U.S. PATENT DOCUMENTS 2,697,008 A 12/1954 Ross
3,409,013 A 11/1968 Berry
(Continued)

FOREIGN PATENT DOCUMENTS

CN 1486161 A 3/2004
CN 1961845 A 5/2007
(Continued)

OTHER PUBLICATIONS

US 9,155,620 B2, 10/2015, Gross et al. (withdrawn)
(Continued)

*Primary Examiner* — Suzette J Gherbi
(74) *Attorney, Agent, or Firm* — Wei & Sleman LLP

(57) ABSTRACT

Apparatus and methods are described herein for use in the delivery and deployment of a prosthetic mitral valve into a heart. In some embodiments, an apparatus includes a catheter assembly, a valve holding tube and a handle assembly. The valve holding tube is releasably couplable to a proximal end portion of the catheter assembly and to a distal end portion of the handle assembly. The handle assembly includes a housing and a delivery rod. The delivery rod is configured to be actuated to move distally relative to the housing to move a prosthetic heart valve disposed within the valve holding tube out of the valve holding tube and distally within a lumen of the elongate sheath of the catheter assembly. The catheter assembly is configured to be actuated
(Continued)

to move proximally relative to the housing such that the prosthetic valve is disposed outside of the lumen of the elongate sheath.

20 Claims, 46 Drawing Sheets

Related U.S. Application Data continuation of application No. PCT/US2016/027770, filed on Apr. 15, 2016.

(60) Provisional application No. 62/312,136, filed on Mar. 23, 2016, provisional application No. 62/148,579, filed on Apr. 16, 2015.

(51) Int. Cl.
  *A61F 2/95* (2013.01)
  *A61B 17/00* (2006.01)
  *A61M 25/06* (2006.01)

(52) U.S. Cl.
  CPC ....... *A61F 2/2466* (2013.01); *A61M 25/0102* (2013.01); *A61B 2017/00292* (2013.01); *A61F 2/2418* (2013.01); *A61F 2/2439* (2013.01); *A61F 2/9517* (2020.05); *A61F 2/9522* (2020.05); *A61F 2/9525* (2020.05); *A61F 2220/0016* (2013.01); *A61F 2230/005* (2013.01); *A61F 2230/0023* (2013.01); *A61F 2250/0039* (2013.01); *A61M 2025/0681* (2013.01)

(56) References Cited

U.S. PATENT DOCUMENTS

| | | |
|---|---|---|
| 3,472,230 A | 10/1969 | Fogarty et al. |
| 3,476,101 A | 11/1969 | Ross |
| 3,548,417 A | 12/1970 | Kischer |
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 3,976,079 A | 8/1976 | Samuels et al. |
| 4,003,382 A | 1/1977 | Dyke |
| 4,035,849 A | 7/1977 | Angell et al. |
| 4,056,854 A | 11/1977 | Boretos et al. |
| 4,073,438 A | 2/1978 | Meyer |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,470,157 A | 9/1984 | Love |
| 4,490,859 A | 1/1985 | Black et al. |
| 4,535,483 A | 8/1985 | Klawitter et al. |
| 4,574,803 A | 3/1986 | Storz |
| 4,585,705 A | 4/1986 | Broderick et al. |
| 4,592,340 A | 6/1986 | Boyles |
| 4,605,407 A | 8/1986 | Black et al. |
| 4,612,011 A | 9/1986 | Kautzky |
| 4,626,255 A | 12/1986 | Reichart et al. |
| 4,638,886 A | 1/1987 | Marietta |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,824,180 A | 4/1989 | Levrai |
| 4,829,990 A | 5/1989 | Fhuroff et al. |
| 4,830,117 A | 5/1989 | Capasso |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,923,013 A | 5/1990 | De Gennaro |
| 4,960,424 A | 10/1990 | Grooters |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 4,996,873 A | 3/1991 | Takeuchi |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,064,435 A | 11/1991 | Porter |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,201,880 A | 4/1993 | Wright et al. |
| 5,266,073 A | 11/1993 | Wall |
| 5,282,847 A | 2/1994 | Trescony et al. |
| 5,295,958 A | 3/1994 | Shturman |
| 5,306,296 A | 4/1994 | Wright et al. |
| 5,332,402 A | 7/1994 | Teitelbaum |
| 5,336,616 A | 8/1994 | Livesey et al. |
| 5,344,442 A | 9/1994 | Deac |
| 5,360,444 A | 11/1994 | Kusuhara |
| 5,364,407 A | 11/1994 | Poll |
| 5,370,685 A | 12/1994 | Stevens |
| 5,397,351 A | 3/1995 | Pavcnik et al. |
| 5,411,055 A | 5/1995 | Kane |
| 5,411,552 A | 5/1995 | Andersen et al. |
| 5,415,667 A | 5/1995 | Frater |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,184 A | 9/1996 | Machiraju |
| 5,554,185 A | 9/1996 | Block et al. |
| 5,571,175 A | 11/1996 | Vanney et al. |
| 5,591,185 A | 1/1997 | Kilmer et al. |
| 5,607,462 A | 3/1997 | Imran |
| 5,607,464 A | 3/1997 | Trescony et al. |
| 5,609,626 A | 3/1997 | Quijano et al. |
| 5,639,274 A | 6/1997 | Fischell et al. |
| 5,662,704 A | 9/1997 | Gross |
| 5,665,115 A | 9/1997 | Cragg |
| 5,674,279 A | 10/1997 | Wright et al. |
| 5,697,905 A | 12/1997 | d'Ambrosio |
| 5,702,368 A | 12/1997 | Stevens et al. |
| 5,716,417 A | 2/1998 | Girard et al. |
| 5,728,068 A | 3/1998 | Leone et al. |
| 5,728,151 A | 3/1998 | Garrison et al. |
| 5,741,333 A | 4/1998 | Frid |
| 5,749,890 A | 5/1998 | Shaknovich |
| 5,756,476 A | 5/1998 | Epstein et al. |
| 5,769,812 A | 6/1998 | Stevens et al. |
| 5,792,179 A | 8/1998 | Sideris |
| 5,800,508 A | 9/1998 | Goicoechea et al. |
| 5,833,673 A | 11/1998 | Ockuly et al. |

(56) References Cited

U.S. PATENT DOCUMENTS

| | | |
|---|---|---|
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,904,697 A | 5/1999 | Gifford, III et al. |
| 5,925,063 A | 7/1999 | Khosravi |
| 5,957,949 A | 9/1999 | Leonhardt et al. |
| 5,968,052 A | 10/1999 | Sullivan, III et al. |
| 5,968,068 A | 10/1999 | Dehdashtian et al. |
| 5,972,030 A | 10/1999 | Garrison et al. |
| 5,993,481 A | 11/1999 | Marcade et al. |
| 6,027,525 A | 2/2000 | Suh et al. |
| 6,042,607 A | 3/2000 | Williamson, IV et al. |
| 6,045,497 A | 4/2000 | Schweich, Jr. et al. |
| 6,063,112 A | 5/2000 | Sgro |
| 6,077,214 A | 6/2000 | Mortier et al. |
| 6,099,508 A | 8/2000 | Bousquet |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,183,411 B1 | 2/2001 | Mortier et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,260,552 B1 | 7/2001 | Mortier et al. |
| 6,261,222 B1 | 7/2001 | Schweich, Jr. et al. |
| 6,264,602 B1 | 7/2001 | Mortier et al. |
| 6,287,339 B1 | 9/2001 | Vazquez et al. |
| 6,299,637 B1 | 10/2001 | Shaolian et al. |
| 6,302,906 B1 | 10/2001 | Goicoechea et al. |
| 6,312,465 B1 | 11/2001 | Griffin et al. |
| 6,332,893 B1 | 12/2001 | Mortier et al. |
| 6,350,277 B1 | 2/2002 | Kocur |
| 6,358,277 B1 | 3/2002 | Duran |
| 6,379,372 B1 | 4/2002 | Dehdashtian et al. |
| 6,402,679 B1 | 6/2002 | Mortier et al. |
| 6,402,680 B2 | 6/2002 | Mortier et al. |
| 6,402,781 B1 | 6/2002 | Langberg et al. |
| 6,406,420 B1 | 6/2002 | McCarthy et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,537,198 B1 | 3/2003 | Vidlund et al. |
| 6,540,782 B1 | 4/2003 | Snyders |
| 6,569,196 B1 | 5/2003 | Vesely |
| 6,575,252 B2 | 6/2003 | Reed |
| 6,582,462 B1 | 6/2003 | Andersen et al. |
| 6,605,112 B1 | 8/2003 | Moll et al. |
| 6,616,684 B1 | 9/2003 | Vidlund et al. |
| 6,622,730 B2 | 9/2003 | Ekvall et al. |
| 6,629,534 B1 | 10/2003 | St. Goar et al. |
| 6,629,921 B1 | 10/2003 | Schweich, Jr. et al. |
| 6,648,077 B2 | 11/2003 | Hoffman |
| 6,648,921 B2 | 11/2003 | Anderson et al. |
| 6,652,578 B2 | 11/2003 | Bailey et al. |
| 6,669,724 B2 | 12/2003 | Park et al. |
| 6,706,065 B2 | 3/2004 | Langberg et al. |
| 6,709,456 B2 | 3/2004 | Langberg et al. |
| 6,723,038 B1 | 4/2004 | Schroeder et al. |
| 6,726,715 B2 | 4/2004 | Sutherland |
| 6,730,118 B2 | 5/2004 | Spenser et al. |
| 6,733,525 B2 | 5/2004 | Yang et al. |
| 6,740,105 B2 | 5/2004 | Yodat et al. |
| 6,746,401 B2 | 6/2004 | Panescu |
| 6,746,471 B2 | 6/2004 | Mortier et al. |
| 6,752,813 B2 | 6/2004 | Goldfarb et al. |
| 6,764,510 B2 | 7/2004 | Vidlund et al. |
| 6,797,002 B2 | 9/2004 | Spence et al. |
| 6,810,882 B2 | 11/2004 | Langberg et al. |
| 6,830,584 B1 | 12/2004 | Seguin |
| 6,854,668 B2 | 2/2005 | Wancho et al. |
| 6,855,144 B2 | 2/2005 | Lesh |
| 6,858,001 B1 | 2/2005 | Aboul-Hosn |
| 6,890,353 B2 | 5/2005 | Cohn et al. |
| 6,893,460 B2 | 5/2005 | Spenser et al. |
| 6,896,690 B1 | 5/2005 | Lambrecht et al. |
| 6,908,424 B2 | 6/2005 | Mortier et al. |
| 6,908,481 B2 | 6/2005 | Cribier |
| 6,936,067 B2 | 8/2005 | Buchanan |
| 6,945,996 B2 | 9/2005 | Sedransk |
| 6,955,175 B2 | 10/2005 | Stevens et al. |
| 6,974,476 B2 | 12/2005 | McGuckin, Jr. et al. |
| 6,976,543 B1 | 12/2005 | Fischer |
| 6,997,950 B2 | 2/2006 | Chawla |
| 7,018,406 B2 | 3/2006 | Seguin et al. |
| 7,018,408 B2 | 3/2006 | Bailey et al. |
| 7,044,905 B2 | 5/2006 | Vidlund et al. |
| 7,060,021 B1 | 6/2006 | Wilk |
| 7,077,862 B2 | 7/2006 | Vidlund et al. |
| 7,087,064 B1 | 8/2006 | Hyde |
| 7,100,614 B2 | 9/2006 | Stevens et al. |
| 7,101,395 B2 | 9/2006 | Tremulis et al. |
| 7,108,717 B2 | 9/2006 | Freidberg |
| 7,112,219 B2 | 9/2006 | Vidlund et al. |
| 7,115,141 B2 | 10/2006 | Menz et al. |
| 7,141,064 B2 | 11/2006 | Scott et al. |
| 7,175,656 B2 | 2/2007 | Khairkhahan |
| 7,198,646 B2 | 4/2007 | Figulla et al. |
| 7,201,772 B2 | 4/2007 | Schwammenthal et al. |
| 7,247,134 B2 | 7/2007 | Vidlund et al. |
| 7,252,682 B2 | 8/2007 | Seguin |
| 7,267,686 B2 | 9/2007 | DiMatteo et al. |
| 7,275,604 B1 | 10/2007 | Wall |
| 7,276,078 B2 | 10/2007 | Spenser et al. |
| 7,276,084 B2 | 10/2007 | Yang et al. |
| 7,316,706 B2 | 1/2008 | Bloom et al. |
| 7,318,278 B2 | 1/2008 | Zhang et al. |
| 7,326,236 B2 | 2/2008 | Andreas et al. |
| 7,329,278 B2 | 2/2008 | Seguin et al. |
| 7,331,991 B2 | 2/2008 | Kheradvar et al. |
| 7,335,213 B1 | 2/2008 | Hyde et al. |
| 7,374,571 B2 | 5/2008 | Pease et al. |
| 7,377,941 B2 | 5/2008 | Rhee et al. |
| 7,381,210 B2 | 6/2008 | Zarbatany et al. |
| 7,381,218 B2 | 6/2008 | Schreck |
| 7,393,360 B2 | 7/2008 | Spenser et al. |
| 7,404,824 B1 | 7/2008 | Webler et al. |
| 7,416,554 B2 | 8/2008 | Lam et al. |
| 7,422,072 B2 | 9/2008 | Dade |
| 7,429,269 B2 | 9/2008 | Schwammenthal et al. |
| 7,442,204 B2 | 10/2008 | Schwammenthal et al. |
| 7,445,631 B2 | 11/2008 | Salahieh et al. |
| 7,462,191 B2 | 12/2008 | Spenser et al. |
| 7,470,285 B2 | 12/2008 | Nugent et al. |
| 7,500,989 B2 | 3/2009 | Solem et al. |
| 7,503,931 B2 | 3/2009 | Kowalsky et al. |
| 7,510,572 B2 | 3/2009 | Gabbay |
| 7,510,575 B2 | 3/2009 | Spenser et al. |
| 7,513,908 B2 | 4/2009 | Lattouf |
| 7,524,330 B2 | 4/2009 | Berreklouw |
| 7,527,647 B2 | 5/2009 | Spence |
| 7,534,260 B2 | 5/2009 | Lattouf |
| 7,556,646 B2 | 7/2009 | Yang et al. |
| 7,579,381 B2 | 8/2009 | Dove |
| 7,585,321 B2 | 9/2009 | Cribier |
| 7,591,847 B2 | 9/2009 | Navia et al. |
| 7,618,446 B2 | 11/2009 | Andersen et al. |
| 7,618,447 B2 | 11/2009 | Case et al. |
| 7,621,948 B2 | 11/2009 | Herrmann et al. |
| 7,632,304 B2 | 12/2009 | Park |
| 7,632,308 B2 | 12/2009 | Loulmet |
| 7,635,386 B1 | 12/2009 | Gammie |
| 7,674,222 B2 | 3/2010 | Nikolic et al. |
| 7,674,286 B2 | 3/2010 | Alfieri et al. |
| 7,695,510 B2 | 4/2010 | Bloom et al. |
| 7,708,775 B2 | 5/2010 | Rowe et al. |

(56) References Cited

U.S. PATENT DOCUMENTS

| | | |
|---|---|---|
| 7,748,389 B2 | 7/2010 | Salahieh et al. |
| 7,766,961 B2 | 8/2010 | Patel et al. |
| 7,789,909 B2 | 9/2010 | Andersen et al. |
| 7,803,168 B2 | 9/2010 | Gifford et al. |
| 7,803,184 B2 | 9/2010 | McGuckin, Jr. et al. |
| 7,803,185 B2 | 9/2010 | Gabbay |
| 7,806,928 B2 | 10/2010 | Rowe et al. |
| 7,837,727 B2 | 11/2010 | Goetz et al. |
| 7,854,762 B2 | 12/2010 | Speziali et al. |
| 7,892,281 B2 | 2/2011 | Seguin et al. |
| 7,896,915 B2 | 3/2011 | Guyenot et al. |
| 7,901,454 B2 | 3/2011 | Kapadia et al. |
| 7,927,370 B2 | 4/2011 | Webler et al. |
| 7,931,630 B2 | 4/2011 | Nishtala et al. |
| 7,942,928 B2 | 5/2011 | Webler et al. |
| 7,955,247 B2 | 6/2011 | Levine et al. |
| 7,955,385 B2 | 6/2011 | Crittenden |
| 7,972,378 B2 | 7/2011 | Tabor et al. |
| 7,988,727 B2 | 8/2011 | Santamore et al. |
| 7,993,394 B2 | 8/2011 | Hariton et al. |
| 8,007,992 B2 | 8/2011 | Tian et al. |
| 8,029,556 B2 | 10/2011 | Rowe |
| 8,043,368 B2 | 10/2011 | Crabtree |
| 8,052,749 B2 | 11/2011 | Salahieh et al. |
| 8,052,750 B2 | 11/2011 | Tuval et al. |
| 8,052,751 B2 | 11/2011 | Aklog et al. |
| 8,062,355 B2 | 11/2011 | Figulla et al. |
| 8,062,359 B2 | 11/2011 | Marquez et al. |
| 8,070,802 B2 | 12/2011 | Lamphere et al. |
| 8,109,996 B2 | 2/2012 | Stacchino et al. |
| 8,142,495 B2 | 3/2012 | Hasenkam et al. |
| 8,152,821 B2 | 4/2012 | Gambale et al. |
| 8,157,810 B2 | 4/2012 | Case et al. |
| 8,167,932 B2 | 5/2012 | Bourang et al. |
| 8,167,934 B2 | 5/2012 | Styrc et al. |
| 8,187,299 B2 | 5/2012 | Goldfarb et al. |
| 8,206,439 B2 | 6/2012 | Gomez Duran |
| 8,216,301 B2 | 7/2012 | Bonhoeffer et al. |
| 8,226,711 B2 | 7/2012 | Mortier et al. |
| 8,236,045 B2 | 8/2012 | Benichou et al. |
| 8,241,274 B2 | 8/2012 | Keogh et al. |
| 8,252,051 B2 | 8/2012 | Chau et al. |
| 8,303,653 B2 | 11/2012 | Bonhoeffer et al. |
| 8,308,796 B2 | 11/2012 | Lashinski et al. |
| 8,323,334 B2 | 12/2012 | Deem et al. |
| 8,353,955 B2 | 1/2013 | Styrc et al. |
| RE44,075 E | 3/2013 | Williamson et al. |
| 8,449,599 B2 | 5/2013 | Chau et al. |
| 8,454,656 B2 | 6/2013 | Tuval |
| 8,470,028 B2 | 6/2013 | Thornton et al. |
| 8,480,730 B2 | 7/2013 | Maurer et al. |
| 8,486,138 B2 | 7/2013 | Vesely |
| 8,506,623 B2 | 8/2013 | Wilson et al. |
| 8,506,624 B2 | 8/2013 | Vidlund et al. |
| 8,578,705 B2 | 11/2013 | Sindano et al. |
| 8,579,913 B2 | 11/2013 | Nielsen |
| 8,579,963 B2 | 11/2013 | Tabor |
| 8,591,573 B2 | 11/2013 | Barone |
| 8,591,576 B2 | 11/2013 | Hasenkam et al. |
| 8,597,347 B2 | 12/2013 | Maurer et al. |
| 8,685,086 B2 | 4/2014 | Navia et al. |
| 8,790,394 B2 | 7/2014 | Miller et al. |
| 8,845,717 B2 | 9/2014 | Khairkhahan et al. |
| 8,888,843 B2 | 11/2014 | Khairkhahan et al. |
| 8,900,214 B2 | 12/2014 | Nance et al. |
| 8,900,295 B2 | 12/2014 | Migliazza et al. |
| 8,926,696 B2 | 1/2015 | Cabiri et al. |
| 8,932,342 B2 | 1/2015 | McHugo et al. |
| 8,932,348 B2 | 1/2015 | Solem et al. |
| 8,945,208 B2 | 2/2015 | Jimenez et al. |
| 8,956,407 B2 | 2/2015 | Macoviak et al. |
| 8,979,922 B2 | 3/2015 | Jayasinghe et al. |
| 8,986,376 B2 | 3/2015 | Solem |
| 9,011,522 B2 | 4/2015 | Annest |
| 9,023,099 B2 | 5/2015 | Duffy et al. |
| 9,034,032 B2 | 5/2015 | McLean et al. |
| 9,034,033 B2 | 5/2015 | McLean et al. |
| 9,039,757 B2 | 5/2015 | McLean et al. |
| 9,039,759 B2 | 5/2015 | Alkhatib et al. |
| 9,078,749 B2 | 7/2015 | Lutter et al. |
| 9,084,676 B2 | 7/2015 | Chau et al. |
| 9,095,433 B2 | 8/2015 | Lutter et al. |
| 9,125,742 B2 | 9/2015 | Yoganathan et al. |
| 9,149,357 B2 | 10/2015 | Seguin |
| 9,161,837 B2 | 10/2015 | Kapadia |
| 9,168,137 B2 | 10/2015 | Subramanian et al. |
| 9,232,998 B2 | 1/2016 | Wilson et al. |
| 9,232,999 B2 | 1/2016 | Maurer et al. |
| 9,241,702 B2 | 1/2016 | Maisano et al. |
| 9,254,192 B2 | 2/2016 | Lutter et al. |
| 9,265,608 B2 | 2/2016 | Miller et al. |
| 9,289,295 B2 | 3/2016 | Aklog et al. |
| 9,289,297 B2 | 3/2016 | Wilson et al. |
| 9,345,573 B2 | 5/2016 | Nyuli et al. |
| 9,364,325 B2 | 6/2016 | Alon et al. |
| 9,480,557 B2 | 11/2016 | Pellegrini et al. |
| 9,480,559 B2 | 11/2016 | Vidlund et al. |
| 9,526,611 B2 | 12/2016 | Tegels et al. |
| 9,597,181 B2 | 3/2017 | Christianson et al. |
| 9,610,159 B2 | 4/2017 | Christianson et al. |
| 9,675,454 B2 | 6/2017 | Vidlund et al. |
| 9,730,792 B2 | 8/2017 | Lutter et al. |
| 10,667,905 B2 * | 6/2020 | Ekvall ................. A61F 2/95 |
| 2001/0018611 A1 | 8/2001 | Solem et al. |
| 2001/0021872 A1 | 9/2001 | Bailey et al. |
| 2001/0025171 A1 | 9/2001 | Mortier et al. |
| 2002/0010427 A1 | 1/2002 | Scarfone et al. |
| 2002/0116054 A1 | 8/2002 | Lundell et al. |
| 2002/0139056 A1 | 10/2002 | Finnell |
| 2002/0151961 A1 | 10/2002 | Lashinski et al. |
| 2002/0161377 A1 | 10/2002 | Rabkin |
| 2002/0173842 A1 | 11/2002 | Buchanan |
| 2003/0010509 A1 | 1/2003 | Hoffman |
| 2003/0036698 A1 | 2/2003 | Kohler et al. |
| 2003/0050694 A1 | 3/2003 | Yang et al. |
| 2003/0078652 A1 | 4/2003 | Sutherland |
| 2003/0100939 A1 | 5/2003 | Yodat et al. |
| 2003/0105519 A1 | 6/2003 | Fasol et al. |
| 2003/0105520 A1 | 6/2003 | Alferness et al. |
| 2003/0120340 A1 | 6/2003 | Liska et al. |
| 2003/0130731 A1 | 7/2003 | Vidlund et al. |
| 2003/0149476 A1 | 8/2003 | Damm et al. |
| 2003/0212454 A1 | 11/2003 | Scott et al. |
| 2004/0039436 A1 | 2/2004 | Spenser et al. |
| 2004/0049266 A1 | 3/2004 | Anduiza et al. |
| 2004/0064014 A1 | 4/2004 | Melvin et al. |
| 2004/0092858 A1 | 5/2004 | Wilson et al. |
| 2004/0093075 A1 | 5/2004 | Kuehne |
| 2004/0097865 A1 | 5/2004 | Anderson et al. |
| 2004/0127983 A1 | 7/2004 | Mortier et al. |
| 2004/0133263 A1 | 7/2004 | Dusbabek et al. |
| 2004/0147958 A1 | 7/2004 | Lam et al. |
| 2004/0152947 A1 | 8/2004 | Schroeder et al. |
| 2004/0162610 A1 | 8/2004 | Liska et al. |
| 2004/0163828 A1 | 8/2004 | Silverstein et al. |
| 2004/0181239 A1 | 9/2004 | Dorn et al. |
| 2004/0186565 A1 | 9/2004 | Schreck |
| 2004/0186566 A1 | 9/2004 | Hindrichs et al. |
| 2004/0260317 A1 | 12/2004 | Bloom et al. |
| 2004/0260389 A1 | 12/2004 | Case et al. |
| 2005/0004652 A1 | 1/2005 | van der Burg et al. |
| 2005/0004666 A1 | 1/2005 | Altieri et al. |
| 2005/0075727 A1 | 4/2005 | Wheatley |
| 2005/0080402 A1 | 4/2005 | Santamore et al. |
| 2005/0096498 A1 | 5/2005 | Houser et al. |
| 2005/0107661 A1 | 5/2005 | Lau et al. |
| 2005/0113798 A1 | 5/2005 | Slater et al. |
| 2005/0113810 A1 | 5/2005 | Houser et al. |
| 2005/0113811 A1 | 5/2005 | Houser et al. |
| 2005/0119519 A9 | 6/2005 | Girard et al. |
| 2005/0121206 A1 | 6/2005 | Dolan |
| 2005/0125012 A1 | 6/2005 | Houser et al. |
| 2005/0137688 A1 | 6/2005 | Salahieh et al. |
| 2005/0137695 A1 | 6/2005 | Salahieh et al. |

(56) References Cited

U.S. PATENT DOCUMENTS

| | | |
|---|---|---|
| 2005/0137698 A1 | 6/2005 | Salahieh et al. |
| 2005/0148815 A1 | 7/2005 | Mortier et al. |
| 2005/0177180 A1 | 8/2005 | Kaganov et al. |
| 2005/0197695 A1 | 9/2005 | Stacchino et al. |
| 2005/0203614 A1 | 9/2005 | Forster et al. |
| 2005/0203615 A1 | 9/2005 | Forster et al. |
| 2005/0203617 A1 | 9/2005 | Forster et al. |
| 2005/0234546 A1 | 10/2005 | Nugent et al. |
| 2005/0240200 A1 | 10/2005 | Bergheim |
| 2005/0251209 A1 | 11/2005 | Saadat et al. |
| 2005/0256567 A1 | 11/2005 | Lim et al. |
| 2005/0288763 A1 | 12/2005 | Andreas et al. |
| 2005/0288766 A1 | 12/2005 | Plain et al. |
| 2006/0004442 A1 | 1/2006 | Spenser et al. |
| 2006/0025784 A1 | 2/2006 | Starksen et al. |
| 2006/0025857 A1 | 2/2006 | Bergheim et al. |
| 2006/0030885 A1 | 2/2006 | Hyde |
| 2006/0042803 A1 | 3/2006 | Gallaher |
| 2006/0047338 A1 | 3/2006 | Jenson et al. |
| 2006/0052868 A1 | 3/2006 | Mortier et al. |
| 2006/0058872 A1 | 3/2006 | Salahieh et al. |
| 2006/0094983 A1 | 5/2006 | Burbank et al. |
| 2006/0129025 A1 | 6/2006 | Levine et al. |
| 2006/0142784 A1 | 6/2006 | Kontos |
| 2006/0161040 A1 | 7/2006 | McCarthy et al. |
| 2006/0161249 A1 | 7/2006 | Realyvasquez et al. |
| 2006/0167541 A1 | 7/2006 | Lattouf |
| 2006/0195134 A1 | 8/2006 | Crittenden |
| 2006/0195183 A1 | 8/2006 | Navia et al. |
| 2006/0229708 A1 | 10/2006 | Powell et al. |
| 2006/0229719 A1 | 10/2006 | Marquez et al. |
| 2006/0241745 A1 | 10/2006 | Solem |
| 2006/0247491 A1 | 11/2006 | Vidlund et al. |
| 2006/0259135 A1 | 11/2006 | Navia et al. |
| 2006/0259136 A1 | 11/2006 | Nguyen et al. |
| 2006/0259137 A1 | 11/2006 | Artof et al. |
| 2006/0276874 A1 | 12/2006 | Wilson et al. |
| 2006/0282161 A1 | 12/2006 | Huynh et al. |
| 2006/0287716 A1 | 12/2006 | Banbury et al. |
| 2006/0287717 A1 | 12/2006 | Rowe et al. |
| 2007/0005131 A1 | 1/2007 | Taylor |
| 2007/0005231 A1 | 1/2007 | Seguchi |
| 2007/0010877 A1 | 1/2007 | Salahieh et al. |
| 2007/0016286 A1 | 1/2007 | Herrmann et al. |
| 2007/0016288 A1 | 1/2007 | Gurskis et al. |
| 2007/0027535 A1 | 2/2007 | Purdy et al. |
| 2007/0038291 A1 | 2/2007 | Case et al. |
| 2007/0050020 A1 | 3/2007 | Spence |
| 2007/0061010 A1 | 3/2007 | Hauser et al. |
| 2007/0066863 A1 | 3/2007 | Rafiee et al. |
| 2007/0073387 A1 | 3/2007 | Forster et al. |
| 2007/0078297 A1 | 4/2007 | Rafiee et al. |
| 2007/0083076 A1 | 4/2007 | Lichtenstein |
| 2007/0083259 A1 | 4/2007 | Bloom et al. |
| 2007/0088431 A1 | 4/2007 | Bourang et al. |
| 2007/0093890 A1 | 4/2007 | Eliasen et al. |
| 2007/0100439 A1 | 5/2007 | Cangialosi et al. |
| 2007/0112422 A1 | 5/2007 | Dehdashtian |
| 2007/0112425 A1 | 5/2007 | Schaller et al. |
| 2007/0118151 A1 | 5/2007 | Davidson |
| 2007/0118154 A1 | 5/2007 | Crabtree |
| 2007/0118210 A1 | 5/2007 | Pinchuk |
| 2007/0118213 A1 | 5/2007 | Loulmet |
| 2007/0142906 A1 | 6/2007 | Figulla et al. |
| 2007/0161846 A1 | 7/2007 | Nikolic et al. |
| 2007/0162103 A1 | 7/2007 | Case et al. |
| 2007/0168024 A1 | 7/2007 | Khairkhahan |
| 2007/0185565 A1 | 8/2007 | Schwammenthal et al. |
| 2007/0185571 A1 | 8/2007 | Kapadia et al. |
| 2007/0203575 A1 | 8/2007 | Forster et al. |
| 2007/0213813 A1 | 9/2007 | Von Segesser et al. |
| 2007/0215362 A1 | 9/2007 | Rodgers |
| 2007/0221388 A1 | 9/2007 | Johnson |
| 2007/0233239 A1 | 10/2007 | Navia et al. |
| 2007/0239265 A1 | 10/2007 | Birdsall |
| 2007/0256843 A1 | 11/2007 | Pahila |
| 2007/0265658 A1 | 11/2007 | Nelson et al. |
| 2007/0267202 A1 | 11/2007 | Mariller |
| 2007/0270932 A1 | 11/2007 | Headley et al. |
| 2007/0270943 A1 | 11/2007 | Solem et al. |
| 2007/0293944 A1 | 12/2007 | Spenser et al. |
| 2008/0009940 A1 | 1/2008 | Cribier |
| 2008/0065011 A1 | 3/2008 | Marchand et al. |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0082163 A1 | 4/2008 | Woo |
| 2008/0082166 A1 | 4/2008 | Styrc et al. |
| 2008/0091264 A1 | 4/2008 | Machold et al. |
| 2008/0114442 A1 | 5/2008 | Mitchell et al. |
| 2008/0125861 A1 | 5/2008 | Webler et al. |
| 2008/0147179 A1 | 6/2008 | Cai et al. |
| 2008/0154355 A1 | 6/2008 | Benichou et al. |
| 2008/0154356 A1 | 6/2008 | Obermiller et al. |
| 2008/0161911 A1 | 7/2008 | Revuelta et al. |
| 2008/0172035 A1 | 7/2008 | Starksen et al. |
| 2008/0177381 A1 | 7/2008 | Navia et al. |
| 2008/0183203 A1 | 7/2008 | Fitzgerald et al. |
| 2008/0188928 A1 | 8/2008 | Salahieh et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0243150 A1 | 10/2008 | Starksen et al. |
| 2008/0243245 A1 | 10/2008 | Fhambar et al. |
| 2008/0255660 A1 | 10/2008 | Guyenot et al. |
| 2008/0255661 A1 | 10/2008 | Straubinger et al. |
| 2008/0281411 A1 | 11/2008 | Berreklouw |
| 2008/0288060 A1 | 11/2008 | Kaye et al. |
| 2008/0293996 A1 | 11/2008 | Evans et al. |
| 2009/0005863 A1 | 1/2009 | Goetz et al. |
| 2009/0048668 A1 | 2/2009 | Wilson et al. |
| 2009/0054968 A1 | 2/2009 | Bonhoeffer et al. |
| 2009/0054974 A1 | 2/2009 | McGuckin, Jr. et al. |
| 2009/0054976 A1 | 2/2009 | Tuval et al. |
| 2009/0062908 A1 | 3/2009 | Bonhoeffer et al. |
| 2009/0076598 A1 | 3/2009 | Salahieh et al. |
| 2009/0082619 A1 | 3/2009 | De Marchena |
| 2009/0088836 A1 | 4/2009 | Bishop et al. |
| 2009/0099410 A1 | 4/2009 | De Marchena |
| 2009/0112309 A1 | 4/2009 | Jaramillo et al. |
| 2009/0131849 A1 | 5/2009 | Maurer et al. |
| 2009/0132035 A1 | 5/2009 | Roth et al. |
| 2009/0137861 A1 | 5/2009 | Goldberg et al. |
| 2009/0138079 A1 | 5/2009 | Tuval et al. |
| 2009/0157175 A1 | 6/2009 | Benichou |
| 2009/0164005 A1 | 6/2009 | Dove et al. |
| 2009/0171432 A1 | 7/2009 | Von Segesser et al. |
| 2009/0171447 A1 | 7/2009 | Von Segesser et al. |
| 2009/0171456 A1 | 7/2009 | Kveen et al. |
| 2009/0177266 A1 | 7/2009 | Powell et al. |
| 2009/0192601 A1 | 7/2009 | Rafiee et al. |
| 2009/0210052 A1 | 8/2009 | Forster et al. |
| 2009/0216322 A1 | 8/2009 | Le et al. |
| 2009/0222076 A1 | 9/2009 | Figulla et al. |
| 2009/0224529 A1 | 9/2009 | Gill |
| 2009/0234318 A1 | 9/2009 | Loulmet et al. |
| 2009/0234435 A1 | 9/2009 | Johnson et al. |
| 2009/0234443 A1 | 9/2009 | Ottma et al. |
| 2009/0240320 A1 | 9/2009 | Tuval et al. |
| 2009/0248149 A1 | 10/2009 | Gabbay |
| 2009/0276040 A1 | 11/2009 | Rowe et al. |
| 2009/0281619 A1 | 11/2009 | Le et al. |
| 2009/0287299 A1 | 11/2009 | Tabor et al. |
| 2009/0319037 A1 | 12/2009 | Rowe et al. |
| 2009/0326575 A1 | 12/2009 | Galdonik et al. |
| 2010/0016958 A1 | 1/2010 | St. Goar et al. |
| 2010/0021382 A1 | 1/2010 | Dorshow et al. |
| 2010/0023117 A1 | 1/2010 | Yoganathan et al. |
| 2010/0036479 A1 | 2/2010 | Hill et al. |
| 2010/0049313 A1 | 2/2010 | Alon et al. |
| 2010/0082094 A1 | 4/2010 | Quadri et al. |

(56) References Cited

U.S. PATENT DOCUMENTS

| | | |
|---|---|---|
| 2010/0161041 A1 | 6/2010 | Maisano et al. |
| 2010/0168839 A1 | 7/2010 | Braido et al. |
| 2010/0179641 A1 | 7/2010 | Ryan et al. |
| 2010/0185277 A1 | 7/2010 | Braido et al. |
| 2010/0185278 A1 | 7/2010 | Schankereli |
| 2010/0191326 A1 | 7/2010 | Alkhatib |
| 2010/0192402 A1 | 8/2010 | Yamaguchi et al. |
| 2010/0204781 A1 | 8/2010 | Alkhatib |
| 2010/0210899 A1 | 8/2010 | Schankereli |
| 2010/0217382 A1 | 8/2010 | Chau et al. |
| 2010/0234940 A1 | 9/2010 | Dolan |
| 2010/0249489 A1 | 9/2010 | Jarvik |
| 2010/0249923 A1 | 9/2010 | Alkhatib et al. |
| 2010/0262157 A1 | 10/2010 | Silver |
| 2010/0280604 A1 | 11/2010 | Zipory et al. |
| 2010/0286768 A1 | 11/2010 | Alkhatib |
| 2010/0298755 A1 | 11/2010 | McNamara et al. |
| 2010/0298931 A1 | 11/2010 | Quadri et al. |
| 2011/0004296 A1 | 1/2011 | Lutter et al. |
| 2011/0015616 A1 | 1/2011 | Straubinger et al. |
| 2011/0015728 A1 | 1/2011 | Jimenez et al. |
| 2011/0015729 A1 | 1/2011 | Jimenez et al. |
| 2011/0029072 A1 | 2/2011 | Gabbay |
| 2011/0046712 A1 | 2/2011 | Melsheimer et al. |
| 2011/0066231 A1 | 3/2011 | Cartledge et al. |
| 2011/0112632 A1 | 5/2011 | Chau et al. |
| 2011/0137397 A1 | 6/2011 | Chau et al. |
| 2011/0137408 A1 | 6/2011 | Bergheim |
| 2011/0224655 A1 | 9/2011 | Asirvatham et al. |
| 2011/0224678 A1 | 9/2011 | Gabbay |
| 2011/0224728 A1 | 9/2011 | Martin et al. |
| 2011/0224784 A1 | 9/2011 | Quinn |
| 2011/0245911 A1 | 10/2011 | Quill et al. |
| 2011/0251682 A1 | 10/2011 | Murray, III et al. |
| 2011/0264206 A1 | 10/2011 | Tabor |
| 2011/0288637 A1 | 11/2011 | De Marchena |
| 2011/0319988 A1 | 12/2011 | Schankereli et al. |
| 2011/0319989 A1 | 12/2011 | Lane et al. |
| 2012/0010694 A1 | 1/2012 | Lutter et al. |
| 2012/0016468 A1 | 1/2012 | Robin et al. |
| 2012/0022640 A1 | 1/2012 | Gross et al. |
| 2012/0035703 A1 | 2/2012 | Lutter et al. |
| 2012/0035713 A1 | 2/2012 | Lutter et al. |
| 2012/0035722 A1 | 2/2012 | Tuval |
| 2012/0059487 A1 | 3/2012 | Cunanan et al. |
| 2012/0083874 A1 | 4/2012 | Dale et al. |
| 2012/0089171 A1 | 4/2012 | Hastings et al. |
| 2012/0101571 A1 | 4/2012 | Thambar et al. |
| 2012/0101572 A1 | 4/2012 | Kovalsky et al. |
| 2012/0116351 A1 | 5/2012 | Chomas et al. |
| 2012/0123529 A1 | 5/2012 | Levi et al. |
| 2012/0165930 A1 | 6/2012 | Gifford, III et al. |
| 2012/0179244 A1 | 7/2012 | Schankereli et al. |
| 2012/0203336 A1 | 8/2012 | Annest |
| 2012/0215303 A1 | 8/2012 | Quadri et al. |
| 2012/0239142 A1 | 9/2012 | Liu et al. |
| 2012/0283824 A1 | 11/2012 | Lutter et al. |
| 2013/0030522 A1 | 1/2013 | Rowe et al. |
| 2013/0053950 A1 | 2/2013 | Rowe et al. |
| 2013/0059747 A1 | 3/2013 | Mann et al. |
| 2013/0066341 A1 | 3/2013 | Ketai et al. |
| 2013/0079873 A1 | 3/2013 | Migliazza et al. |
| 2013/0131788 A1 | 5/2013 | Quadri et al. |
| 2013/0172978 A1 | 7/2013 | Vidlund et al. |
| 2013/0184811 A1 | 7/2013 | Rowe et al. |
| 2013/0190860 A1 | 7/2013 | Sundt, III |
| 2013/0190861 A1 | 7/2013 | Chau et al. |
| 2013/0197622 A1 | 8/2013 | Mitra et al. |
| 2013/0226288 A1 | 8/2013 | Goldwasser et al. |
| 2013/0231735 A1 | 9/2013 | Deem et al. |
| 2013/0268064 A1 | 10/2013 | Duffy |
| 2013/0274874 A1 | 10/2013 | Hammer |
| 2013/0282101 A1 | 10/2013 | Eidenschink et al. |
| 2013/0310928 A1 | 11/2013 | Morriss et al. |
| 2013/0317603 A1 | 11/2013 | McLean et al. |
| 2013/0325041 A1 | 12/2013 | Annest et al. |
| 2013/0325110 A1 | 12/2013 | Khalil et al. |
| 2013/0338752 A1 | 12/2013 | Geusen et al. |
| 2014/0005767 A1 | 1/2014 | Glazier et al. |
| 2014/0081323 A1 | 3/2014 | Hawkins |
| 2014/0094918 A1 | 4/2014 | Vishnubholta et al. |
| 2014/0128963 A1* | 5/2014 | Quill .............. A61F 2/2436 623/2.11 |
| 2014/0142691 A1 | 5/2014 | Pouletty |
| 2014/0163668 A1 | 6/2014 | Rafiee |
| 2014/0194981 A1 | 7/2014 | Menk et al. |
| 2014/0214159 A1 | 7/2014 | Vidlund et al. |
| 2014/0222142 A1 | 8/2014 | Kovalsky et al. |
| 2014/0243966 A1 | 8/2014 | Garde et al. |
| 2014/0277419 A1 | 9/2014 | Garde et al. |
| 2014/0296969 A1 | 10/2014 | Tegels et al. |
| 2014/0296970 A1 | 10/2014 | Ekvall et al. |
| 2014/0296971 A1 | 10/2014 | Tegels et al. |
| 2014/0296972 A1 | 10/2014 | Tegels et al. |
| 2014/0296975 A1 | 10/2014 | Tegels et al. |
| 2014/0303718 A1 | 10/2014 | Tegels et al. |
| 2014/0309732 A1 | 10/2014 | Solem |
| 2014/0316516 A1 | 10/2014 | Vidlund et al. |
| 2014/0316518 A1 | 10/2014 | Kheradvar et al. |
| 2014/0324160 A1 | 10/2014 | Benichou et al. |
| 2014/0324161 A1 | 10/2014 | Tegels et al. |
| 2014/0324164 A1 | 10/2014 | Gross et al. |
| 2014/0358224 A1 | 12/2014 | Tegels et al. |
| 2014/0364944 A1 | 12/2014 | Lutter et al. |
| 2014/0379076 A1 | 12/2014 | Vidlund et al. |
| 2015/0005874 A1 | 1/2015 | Vidlund et al. |
| 2015/0011821 A1 | 1/2015 | Gorman et al. |
| 2015/0025553 A1 | 1/2015 | Del Nido et al. |
| 2015/0057705 A1 | 2/2015 | Vidlund |
| 2015/0073542 A1 | 3/2015 | Heldman |
| 2015/0073545 A1 | 3/2015 | Braido |
| 2015/0105856 A1 | 4/2015 | Rowe et al. |
| 2015/0112430 A1* | 4/2015 | Creaven .......... A61F 2/2436 623/2.11 |
| 2015/0119936 A1 | 4/2015 | Gilmore et al. |
| 2015/0119978 A1 | 4/2015 | Tegels et al. |
| 2015/0127096 A1 | 5/2015 | Rowe et al. |
| 2015/0142100 A1 | 5/2015 | Morriss et al. |
| 2015/0142101 A1 | 5/2015 | Coleman et al. |
| 2015/0142103 A1 | 5/2015 | Vidlund |
| 2015/0142104 A1 | 5/2015 | Braido |
| 2015/0173897 A1 | 6/2015 | Raanani et al. |
| 2015/0196393 A1 | 7/2015 | Vidlund et al. |
| 2015/0196688 A1 | 7/2015 | James et al. |
| 2015/0202044 A1 | 7/2015 | Chau et al. |
| 2015/0216653 A1 | 8/2015 | Freudenthal |
| 2015/0216660 A1 | 8/2015 | Pintor et al. |
| 2015/0223820 A1 | 8/2015 | Olson et al. |
| 2015/0223934 A1 | 8/2015 | Vidlund et al. |
| 2015/0238729 A1 | 8/2015 | Jenson et al. |
| 2015/0272731 A1 | 10/2015 | Racchini et al. |
| 2015/0305860 A1 | 10/2015 | Wang et al. |
| 2015/0305864 A1 | 10/2015 | Quadri et al. |
| 2015/0305867 A1 | 10/2015 | Liu et al. |
| 2015/0305868 A1 | 10/2015 | Lutter et al. |
| 2015/0327995 A1 | 11/2015 | Morin et al. |
| 2015/0328001 A1 | 11/2015 | McLean et al. |
| 2015/0335424 A1 | 11/2015 | McLean et al. |
| 2015/0335429 A1 | 11/2015 | Morriss et al. |
| 2015/0342717 A1 | 12/2015 | O'Donnell et al. |
| 2015/0351903 A1 | 12/2015 | Morriss et al. |
| 2015/0351906 A1 | 12/2015 | Hammer et al. |
| 2016/0008131 A1 | 1/2016 | Christianson et al. |
| 2016/0067042 A1 | 3/2016 | Murad et al. |
| 2016/0074160 A1 | 3/2016 | Christianson et al. |
| 2016/0106537 A1 | 4/2016 | Christianson et al. |
| 2016/0113764 A1 | 4/2016 | Sheahan et al. |
| 2016/0143736 A1 | 5/2016 | Mdlund et al. |
| 2016/0151155 A1 | 6/2016 | Lutter et al. |
| 2016/0206280 A1 | 7/2016 | Vidlund et al. |
| 2016/0242902 A1 | 8/2016 | Morriss et al. |
| 2016/0262879 A1 | 9/2016 | Meiri et al. |
| 2016/0262881 A1 | 9/2016 | Schankereli et al. |
| 2016/0317290 A1 | 11/2016 | Chau et al. |

(56) References Cited

U.S. PATENT DOCUMENTS

| | | | |
|---|---|---|---|
| 2016/0324635 A1 | 11/2016 | Vidlund et al. |
| 2016/0331527 A1 | 11/2016 | Vidlund et al. |
| 2016/0346086 A1 | 12/2016 | Solem |
| 2016/0367365 A1 | 12/2016 | Conklin |
| 2016/0367367 A1 | 12/2016 | Maisano et al. |
| 2016/0367368 A1 | 12/2016 | Vidlund et al. |
| 2017/0079790 A1 | 3/2017 | Vidlund et al. |
| 2017/0128208 A1 | 5/2017 | Christianson et al. |
| 2017/0181854 A1 | 6/2017 | Christianson et al. |
| 2017/0196688 A1 | 7/2017 | Christianson et al. |
| 2017/0252153 A1 | 9/2017 | Chau et al. |
| 2017/0266001 A1 | 9/2017 | Vidlund et al. |
| 2021/0220135 A1* | 7/2021 | Kovalsky | A61F 2/2433 |

FOREIGN PATENT DOCUMENTS

| | | |
|---|---|---|
| CN | 2902226 Y | 5/2007 |
| CN | 101146484 A | 3/2008 |
| CN | 101180010 A | 5/2008 |
| CN | 101180010 | 12/2010 |
| CN | 101984938 A | 3/2011 |
| CN | 102639179 A | 8/2012 |
| CN | 102869317 A | 1/2013 |
| CN | 102869318 A | 1/2013 |
| CN | 102869321 A | 1/2013 |
| CN | 103220993 A | 7/2013 |
| DE | 2246526 | 3/1973 |
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049815 A1 | 4/2002 |
| DE | 102006052564 B3 | 12/2007 |
| DE | 102006052710 A1 | 5/2008 |
| DE | 102007043831 A1 | 4/2009 |
| EP | 0103546 A1 | 3/1984 |
| EP | 1057460 A1 | 12/2000 |
| EP | 1088529 A2 | 4/2001 |
| EP | 1469797 | 10/2004 |
| EP | 1469797 B1 | 11/2005 |
| EP | 2111800 A1 | 10/2009 |
| EP | 2193762 A1 | 6/2010 |
| EP | 2278944 A2 | 2/2011 |
| EP | 2747707 A1 | 7/2014 |
| EP | 2918248 A1 | 9/2015 |
| FR | 2788217 A1 | 7/2000 |
| FR | 2815844 A1 | 5/2002 |
| JP | 2003505146 A | 2/2003 |
| JP | 2008504078 A | 2/2008 |
| JP | 2009511229 A | 3/2009 |
| JP | 2009514628 A | 4/2009 |
| JP | 2013525039 A | 6/2013 |
| JP | 2013538086 A | 10/2013 |
| JP | 2014513585 A | 6/2014 |
| NL | 1017275 C2 | 8/2002 |
| SU | 1271508 | 11/1986 |
| WO | 9217118 A1 | 10/1992 |
| WO | 9301768 A1 | 2/1993 |
| WO | 9829057 A1 | 7/1998 |
| WO | 9940964 A1 | 8/1999 |
| WO | 9947075 A1 | 9/1999 |
| WO | 2000018333 A1 | 4/2000 |
| WO | 2000030550 A1 | 6/2000 |
| WO | 200041652 A1 | 7/2000 |
| WO | 200047139 A1 | 8/2000 |
| WO | 2001035878 A2 | 5/2001 |
| WO | 2001049213 A2 | 7/2001 |
| WO | 0154625 A1 | 8/2001 |
| WO | 2001054624 A1 | 8/2001 |
| WO | 2001056512 A1 | 8/2001 |
| WO | 2001061289 A1 | 8/2001 |
| WO | 0176510 A2 | 10/2001 |
| WO | 200176510 A2 | 10/2001 |
| WO | 0182840 | 11/2001 |
| WO | 2001082840 A1 | 11/2001 |
| WO | 2002004757 A1 | 1/2002 |
| WO | 0222054 A1 | 3/2002 |
| WO | 2002022054 A1 | 3/2002 |
| WO | 2002028321 A2 | 4/2002 |
| WO | 0236048 A1 | 5/2002 |
| WO | 2002041789 A2 | 5/2002 |
| WO | 0243620 A1 | 6/2002 |
| WO | 0249540 A2 | 6/2002 |
| WO | 2002043620 A1 | 6/2002 |
| WO | 2002049540 A2 | 6/2002 |
| WO | 2002076348 A1 | 10/2002 |
| WO | 2003003943 A2 | 1/2003 |
| WO | 2003030776 A2 | 4/2003 |
| WO | 03047468 A1 | 6/2003 |
| WO | 2003049619 A2 | 6/2003 |
| WO | 2004019825 A1 | 3/2004 |
| WO | 2005102181 A1 | 11/2005 |
| WO | 2006005082 A2 | 1/2006 |
| WO | 2006014233 A2 | 2/2006 |
| WO | 2006034008 A2 | 3/2006 |
| WO | 2006070372 A2 | 7/2006 |
| WO | 2006113906 A1 | 10/2006 |
| WO | 2006127756 A2 | 11/2006 |
| WO | 2007081412 A1 | 7/2007 |
| WO | 2008005405 A2 | 1/2008 |
| WO | 2008035337 A2 | 3/2008 |
| WO | 2008091515 A2 | 7/2008 |
| WO | 2008125906 A2 | 10/2008 |
| WO | 2008147964 A1 | 12/2008 |
| WO | 2009024859 A2 | 2/2009 |
| WO | 2009026563 A2 | 2/2009 |
| WO | 2009045338 A1 | 4/2009 |
| WO | 2009094500 A1 | 7/2009 |
| WO | 2009132187 A1 | 10/2009 |
| WO | 2010022138 A2 | 2/2010 |
| WO | 2010090878 A2 | 8/2010 |
| WO | 2010098857 A1 | 9/2010 |
| WO | 2010121076 A2 | 10/2010 |
| WO | 2011017440 A2 | 2/2011 |
| WO | 2011022658 A1 | 2/2011 |
| WO | 2011069048 A2 | 6/2011 |
| WO | 2011072084 A2 | 6/2011 |
| WO | 2011106735 A1 | 9/2011 |
| WO | 2011109813 A2 | 9/2011 |
| WO | 2011159342 A1 | 12/2011 |
| WO | 2011163275 A2 | 12/2011 |
| WO | 2012027487 A2 | 3/2012 |
| WO | 2012036742 A2 | 3/2012 |
| WO | 2012177942 A2 | 12/2012 |
| WO | 2013045262 A1 | 4/2013 |
| WO | 2013096411 A1 | 6/2013 |
| WO | 2013175468 A2 | 11/2013 |
| WO | 2014071077 A1 | 5/2014 |
| WO | 2014121280 A2 | 8/2014 |
| WO | 2014144247 A1 | 9/2014 |
| WO | 2014144937 A2 | 9/2014 |
| WO | 2014162306 A2 | 10/2014 |
| WO | 2014189974 A1 | 11/2014 |
| WO | 2015051430 A1 | 4/2015 |
| WO | 2015058039 A1 | 4/2015 |
| WO | 2015063580 A2 | 5/2015 |
| WO | 2015065646 A1 | 5/2015 |
| WO | 2015120122 A2 | 8/2015 |
| WO | 2015138306 A2 | 9/2015 |
| WO | 2016112085 A1 | 7/2016 |
| WO | 2016126942 A2 | 8/2016 |
| WO | 2016168609 A1 | 10/2016 |
| WO | 2016196933 A1 | 12/2016 |

OTHER PUBLICATIONS

Bernacca, G. M. et al., "Polyurethane heart valves: Fatigue failure, calcification, and polyurethane structure," Journal of Biomedical Materials Research, Mar. 5, 1997, 34(3):371-379.

Drawbaugh, K., "Feature—Heart Surgeons Explore Minimally Invasive Methods," Reuters Limited, Jul. 16, 1996, 3 pages.

(56) References Cited

OTHER PUBLICATIONS

Henning Rud Andersen, "Transluminal Catheter Implanted Prosthetic Heart Valves," International Journal of Angiology, 1998, Issue 2, vol. 7 pp. 102-106.

Ma L., et al., Double-crowned valved stents for off-pump mitral valve replacement. Eur J Cardiothorac Surg. Aug. 200528(2): 194-198.

Moazami, N et al., "Transluminal aortic valve placement: A feasibility study with a newly designed collapsible aortic valve," ASAIO Journal, Sep./ Oct. 1996 42(5):M381-M385.

Rosch, J. et al., "The Birth, Early Years and Future of Interventional Radiology," J Vasc Interv Radiol., Jul. 2003, 4:841-853.

US 9,155,620, Oct. 2015, Gross et al. (withdrawn)

Extended European Search Report including Written Opinion for Application No. EP20168419.8, dated Jul. 21, 2020, pp. 1-8.

Al Zaibag, Muayed, et al., "Percutaneous Balloon Valvotomy in Tricuspid Stenos's," British Heart Journal, Jan. 1987, vol. 57, No. 1, pp. 51-53.

Al-Khaja, N. et al., "Eleven Years' Experience with Carpentier-Edwards Biological Valves in Relation to Survival and Complications," European Journal of Cardiothoracic Surgery, Jun. 30, 1989, 3:305-311.

Almagor, Y. et al., "Balloon Expandable Stent Implantation in Stenotic Right Heart Valved Conduits," Journal of the American College of Cardiology, Nov. 1, 1990, 16(6):1310-1314.

H. R. Andersen et al., "Transluminal Implantation of Artificial Heart Valves: Description of a New Expandable Aortic Valve and Initial Results with Implantation by Catheter Technique in Closed Chest Pigs," European Heart Journal, 1992, Issue 5, vol. 13, pp. 704-708.

Andersen, H. R., "History of Percutaneous Aortic Valve Prosthesis," Herz, Aug. 2009, 34(5):343-346.

Andersen, H. R., "Transluminal catheter implanted prosthetic heart valves," International Journal of Angiology, 1998, 7(2):102-106.

Robert C. Ashton Jr., "Development of an Intraluminal Device for the Treatment of Aortic Regurgitation: Prototype and in Vitro Testing System," Journal of Thoracic and Cardiovascular Surgery, 1996, Issue/vol. 112, pp. 979-983.

Benchimol, A. et al., "Simultaneous Left Ventricular Echocardiography and Aortic Blood Velocity During Rapid Right Ventricular Pacing in Man," The American Journal of the Medical Sciences, Jan.-Feb. 1977, 273(1):55-62.

G. M. Bernacca, et al., "Polyurethane Heart Valves: Fatigue Failure, Calcification, and Polyurethane Structure," Journal of Biomedical Materials Research, Mar. 5, 1997, Issue 3, vol. 34, pp. 371-379.

Boudjemline, Y. et al., "Steps Toward the Percutaneous Replacement of Atrioventricular Valves: An Experimental Study," Journal of the American College of Cardiology, Jul. 2005, 46(2):360-365.

Buckberg, G. et al., "Restoring Papillary Muscle Dimensions During Restoration In Dilated Hearts," Interactive Cardiovascular and Thoracic Surgery, 2005, 4:475-477.

Chamberlain, G., "Ceramics Replace Body Parts," Design News, Jun. 9, 1997, Issue 11, vol. 52, 5 pages.

Choo, S. J. et al., "Aortic Root Geometry: Pattern of Differences Between Leaflets and Sinuses of Valsava," The Journal of Heart Valve Disease, Jul. 1999, 8:407-415.

Declaration of Malcolm J. R. Dalrymple-Hay, Nov. 9, 2012, pp. 1-11; with Curriculum Vitae, Oct. 4, 2012.

Dotter, C. T. et al., "Transluminal Treatment of Arteriosclerotic Obstruction. Description of a New Technic and a Preliminary Report of its Application," Circulation, Nov. 1964, 30:654-670.

Gray, H., The Aorta, Anatomy of the Human Body, 1918, Retrieved from the Internet <http://www.bartleby.com/107/142.html>, Dec. 10, 2012, 5 pages.

Gray, H., The Heart, Anatomy of the Human Body, 1918, Retrieved from the Internet <http://education.yahoo.com/reference/gray/subjects/subject/138>, Aug. 10, 2012, 9 pages.

Greenhalgh, E. S., "Design and characterization of a biomimetic prosthetic aortic heart valve," 1994, ProQuest Dissertations and Theses, Department of Fiber and Polymer Science, North Carolina State University at Raleigh, 159 pages.

Inoue, K. et al., "Clinical Application of Transvenous Mitral Commissurotomy by a New Balloon Catheter," The Journal of Thoracic and Cardiovascular Surgery, 1984, 87:394-402.

Jin, X. Y. et al., "Aortic Root Geometry and Stentless Porcine Valve Competence," Seminars in Thoracic and Cardiovascular Surgery, Oct. 1999, 11(4):145-150.

Knudsen, L. L. et al., "Catheter-implanted prosthetic heart valves. Transluminal catheter implantation of a new expandable artificial heart valve in the descending thoracic aorta in isolated vessels and closed chest pigs," The International Journal of Artificial Organs, 1993, 16(5):253-262.

Kolata, G., "Device That Opens Clogged Arteries Gets a Failing Grade in a New Study," New York Times [online], <http://www.nytimes.com/1991/01/03/health/device-that-opens-clogged-ar-teries-gets-a-faili . . . ,>, published Jan. 3, 1991,retrieved from the Internet on Feb. 5, 2016, 3 pages.

Lawrence, D. D., "Percutaneous Endovascular Graft: Experimental Evaluation," Radiology, 1987, 163:357-360.

Lozonschi, L., et al. "Transapical mitral valved stent implantation: A survival series in swine," The Journal of Thoracic and Cardiovascular Surgery, 140(2):422-426 (Aug. 2010) published online Mar. 12, 2010, 1 page.

Lutter, Georg, et al., Mitral valved stent implantation, European Journal of Cardio-Thoracic Surgery, 2010, vol. 38, pp. 350-355.

Ma, L. et al., "Double-crowned valved stents for off-pump mitral valve replacement," European Journal of Cardio-Thoracic Surgery, Aug. 2005, 28(2): 194-198.

Orton, C., "Mitralseal: Hybrid Transcatheter Mitral Valve Replacement," Symposium: Small Animal Proceedings, 2011, pp. 311-312.

Pavcnik, D. et al. "Development and Initial Experimental Evaluation of a Prosthetic Aortic Valve for Transcatheter Placement," Radiology, 1992; 183:151-154.

Porstmann, W. et al., "Der Verschluβ des Ductus Arteriosus Persistens ohne Thorakotomie," Thoraxchirurgie Vaskuläre Chirurgie, Band 15, Heft 2, Stuttgart, Apr. 1967, pp. 199-203.

Rashkind, W. J., "Creation of an Atrial Septal Defect Without Thoracotomy," The Journal of the American Medical Association, Jun. 13, 1966, 196( 11 ): 173-174.

Rashkind, W. J., "Historical Aspects of Interventional Cardiology: Past, Present, Future," Texas Heart Institute Journal, Dec. 1986, 13(4):363-367.

Reul, H. et al., "The Geomety of the Aortic Root in Health, at Valve Disease and After Valve Replacement," J. Biomechanics, 1990, 23(2):181-191.

Ross, D. N., "Aortic Valve Surgery," Guy's Hospital, London, 1968, pp. 192-197.

Rousseau, E. P. M. et al., "A Mechanical Analysis of the Closed Hancock Heart Valve Prosthesis," Journal of Biomechanics, 1998, 21(7):545-562.

Sabbah, A. N. et al., "Mechanical Factors in the Degeneration of Porcine Bioprosthetic Valves: An Overview," Dec. 1989, Journal of Cardiac Surgery, 4(4):302-309.

Selby, M.D., J. Bayne, "Experience with New Retrieval Forceps for Foreign Body Removal in the Vascular, Urinary, and Biliary Systems," Radiology 1990; 176:535-538.

Serruys, P.W., et al., "Stenting of Coronary Arteries. Are we the Sorcerer?s Apprentice?," European Heart Journal (1989) 10, 774-782, pp. 37-45, Jun. 13, 1989.

Sigwart, U., "An Overview of Intravascular Stents: Old and New," Chapter 48, Interventional Cardiology, 2nd Edition, W.B. Saunders Company, Philadelphia, PA, © 1994, 1990, pp. 803-815.

Tofeig, M. et al., "Transcatheter Closure of a Mid-Muscular Ventricular Septal Defect with an Amplatzer VSD Occluder Device," Heart, 1999, 81:438-440.

Uchida, Barry T., et al., "Modifications of Gianturco Expandable Wire Stents," AJR:150, May 1988, Dec. 3, 1987, pp. 1185-1187.

Watt, A.H., et al. "Intravenous Adenosine in the Treatment of Supraventricular Tachycardia; a Dose-Ranging Study and Interaction with Dipyridamole," British Journal of Clinical Pharmacology (1986), 21, pp. 227-230.

Webb, J. G. et al., "Percutaneous Aortic Valve Implantation Retrograde from the Femoral Artery," Circulation, 2006, 113:842-850.

(56) References Cited

OTHER PUBLICATIONS

Wheatley, M.D., David J., "Valve Prostheses," Rob & Smith's Operative Surgery, Fourth Edition, pp. 415-424, ButtenNorths 1986.
Yoganathan, A. P. et al., "The Current Status of Prosthetic Heart Valves," In Polymetric Materials and Artificial Organs, Mar. 20, 1983, pp. 111-150, American Chemical Society.
"Shape Memory Alloys," Retrieved from the Internet: <http://webdocs.cs.ualberta.ca/~database/MEMS/sma.html>, Feb. 5, 2016, 3 pages.

* cited by examiner

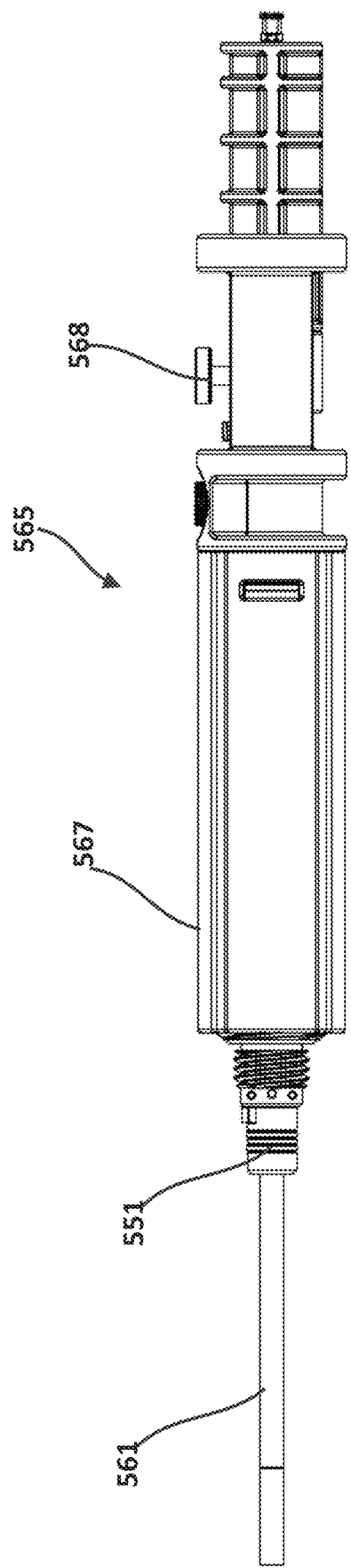
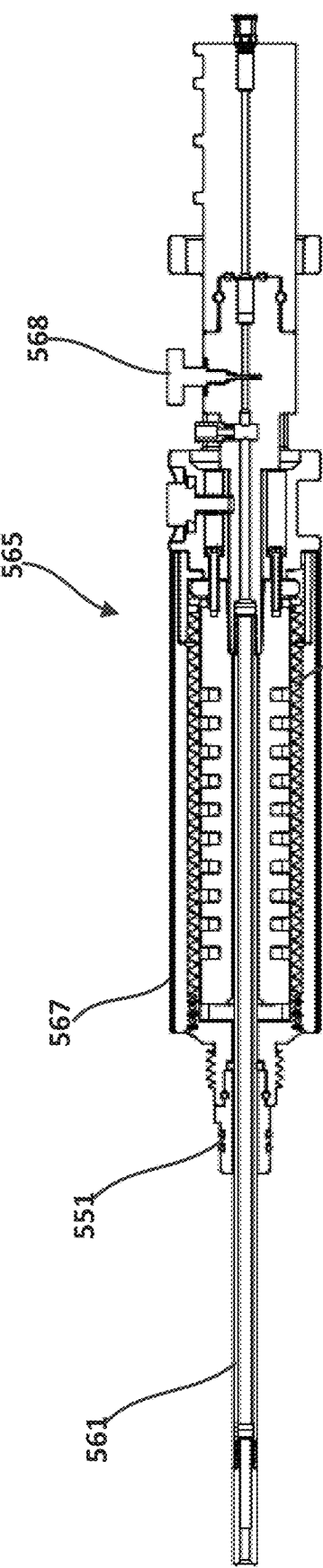
FIG. 21A
FIG. 21B

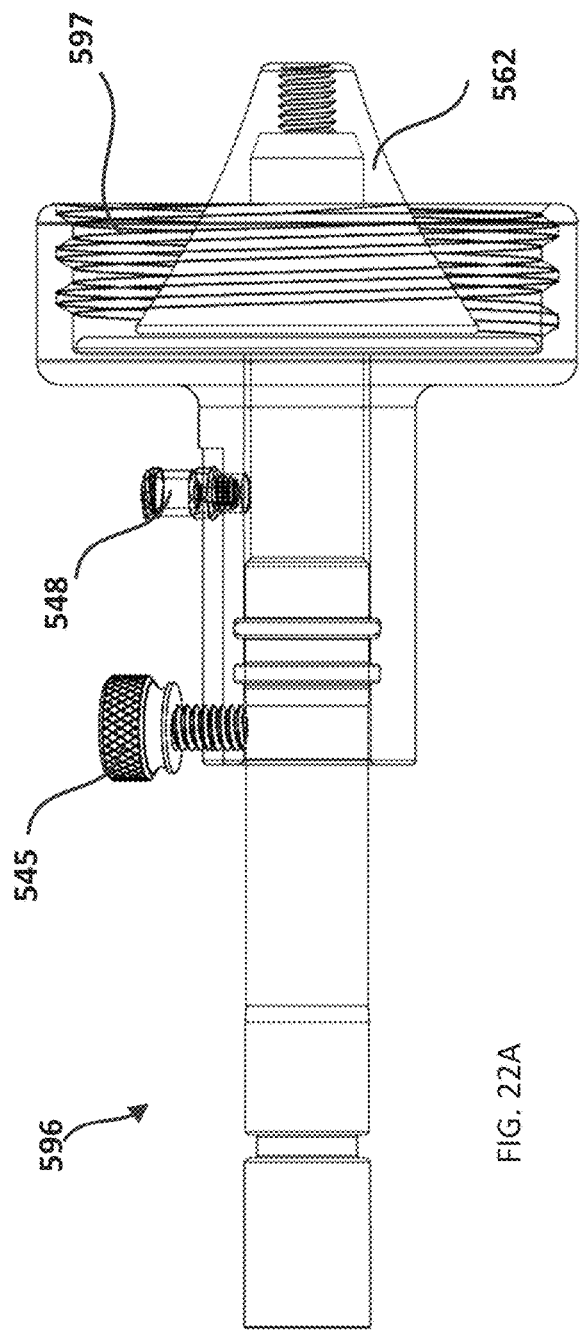
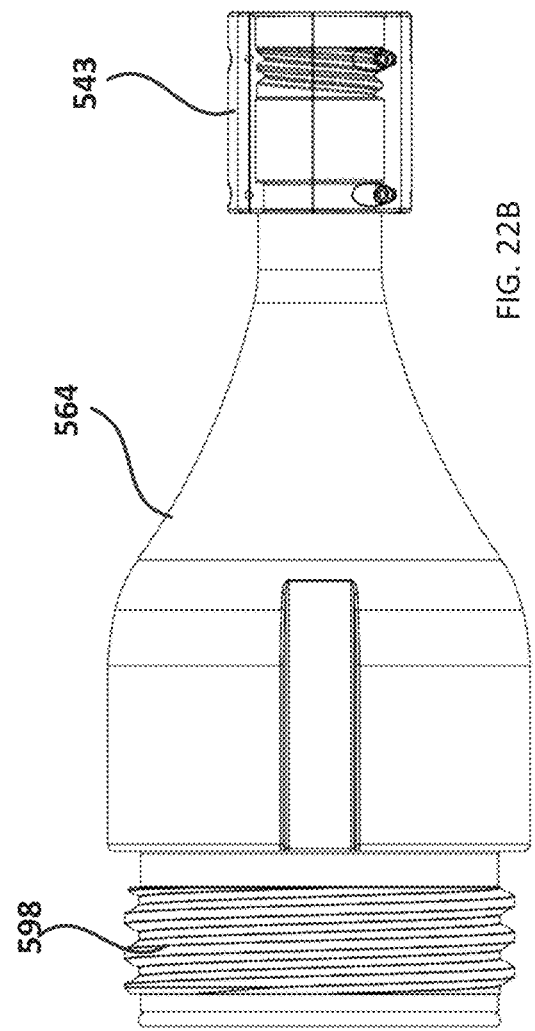
FIG. 22A
FIG. 22B

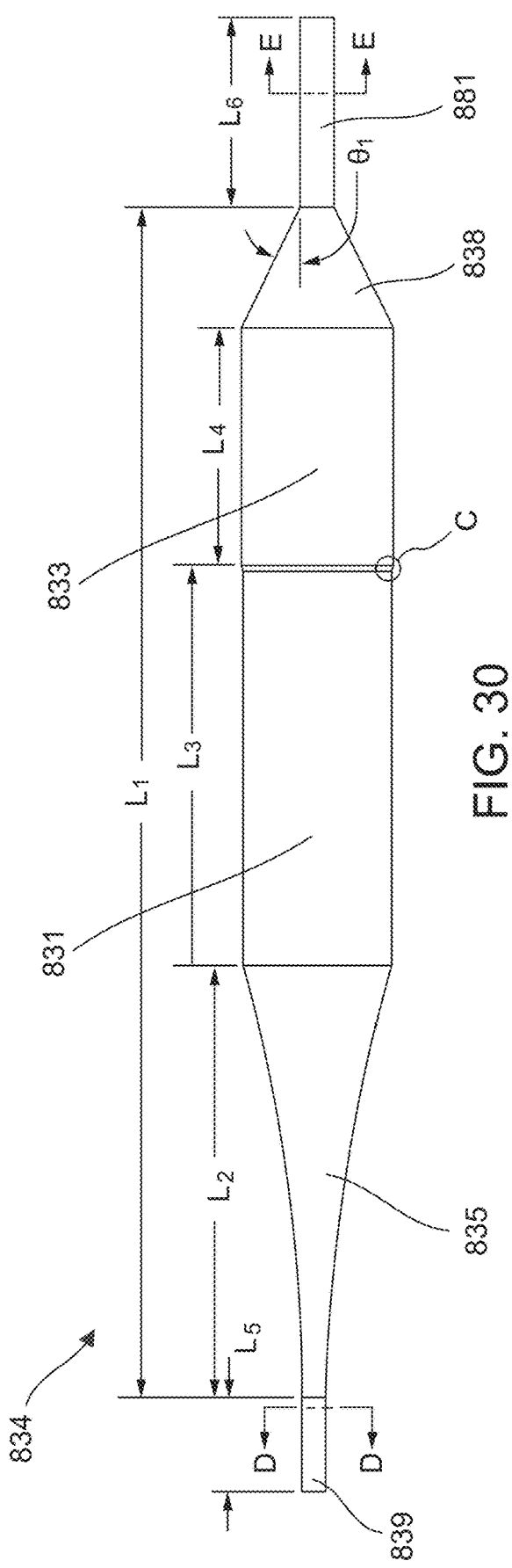
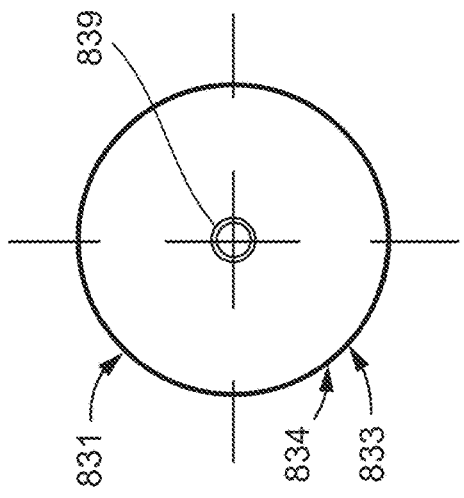
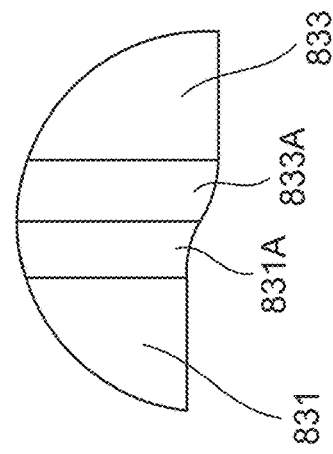
FIG. 30
FIG. 33
FIG. 32

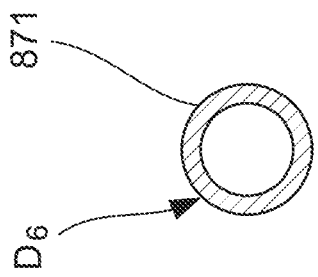
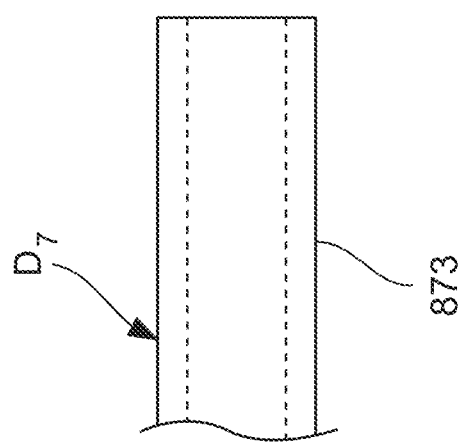
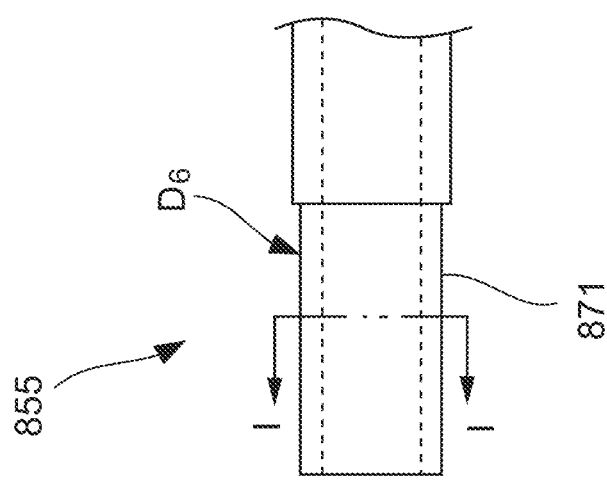

APPARATUS AND METHODS FOR DELIVERY, REPOSITIONING, AND RETRIEVAL OF TRANSCATHETER PROSTHETIC VALVES

CROSS-REFERENCE TO RELATED APPLICATIONS

This application is a divisional of U.S. application Ser. No. 15/730,148, filed on Oct. 11, 2017, which is a continuation of International Application No. PCT/US2016/027770, filed on Apr. 15, 2016, which claims priority to and the benefit of U.S. Provisional Patent Application No. 62/312, 136, entitled "Apparatus and Methods for Delivery, Repositioning, and Retrieval of Transcatheter Prosthetic Valves," filed Mar. 23, 2016, and U.S. Provisional Patent Application No. 62/148,579, entitled "Apparatus and Methods for Delivery, Repositioning, and Retrieval of Transcatheter Prosthetic Valves," filed Apr. 16, 2015, each of the disclosures of which is incorporated herein by reference in its entirety.

BACKGROUND

Embodiments are described herein that relate to devices and methods for use in the delivery, deployment, repositioning and retrieval of transcatheter prosthetic heart valves.

Prosthetic heart valves can pose particular challenges for delivery and deployment within a heart. Valvular heart disease, and specifically, aortic and mitral valve disease is a significant health issue in the United States (US); annually approximately 90,000 valve replacements are conducted in the US. Traditional valve replacement surgery involving the orthotopic replacement of a heart valve, is considered an "open heart" surgical procedure. Briefly, the procedure necessitates surgical opening of the thorax, the initiation of extra-corporeal circulation with a heart-lung machine, stopping and opening the heart, excision and replacement of the diseased valve, and re-starting of the heart. While valve replacement surgery typically carries a 1-4% mortality risk in otherwise healthy persons, a significantly higher morbidity is associated to the procedure largely due to the necessity for extra-corporeal circulation. Further, open heart surgery is often poorly tolerated in elderly patients. Thus elimination of the extra-corporeal component of the procedure could result in reduction in morbidities and cost of valve replacement therapies could be significantly reduced.

While replacement of the aortic valve in a transcatheter manner is the subject of intense investigation, lesser attention has been focused on the mitral valve. This is in part reflective of the greater level of complexity associated to the native mitral valve apparatus, and thus, a greater level of difficulty with regards to inserting and anchoring the replacement prosthesis. Thus, a need exists for delivery devices and methods for transcatheter heart valve replacements. There is also a need for devices and methods for repositioning and/or retrieving deployed prosthetic heart valves.

SUMMARY

Apparatus and methods are described herein for use in the delivery and deployment of a prosthetic mitral valve into a heart. In some embodiments, an apparatus includes a catheter assembly, a valve holding tube and a handle assembly. The valve holding tube is releasably couplable to a proximal end portion of the catheter assembly and to a distal end portion of the handle assembly. The handle assembly includes a housing and a delivery rod. The delivery rod is configured to be actuated to move distally relative to the housing to move a prosthetic heart valve disposed within the valve holding tube out of the valve holding tube and distally within a lumen of the elongate sheath of the catheter assembly. The catheter assembly is configured to be actuated to move proximally relative to the housing such that the prosthetic valve is disposed outside of the lumen of the elongate sheath.

BRIEF DESCRIPTION OF THE FIGURES

FIG. 21A is a side view of a handle assembly of the valve loading device of FIG. 18.

FIG. 21B is a cross-sectional view of the handle assembly of FIG. 21A.

FIG. 22A is a side view of a top cap assembly of the valve loading device of FIG. 18.

FIG. 22B is a side view of an outer funnel of the valve loading device of FIG. 18.

FIG. 30 is a side view of a balloon member of the dilator device of FIG. 28 in an expanded configuration.

FIG. 32 is an enlarged view of detail C in FIG. 30.

FIG. 33 is a distal end view of the balloon member of FIG. 30.

FIG. 41 is a side view of a distal portion of the elongate inflation tube of FIG. 28.

FIG. 42 is a cross-sectional view of the elongate inflation tube of FIG. 41 taken along line I-I in FIG. 41.

DETAILED DESCRIPTION

Figure 1:
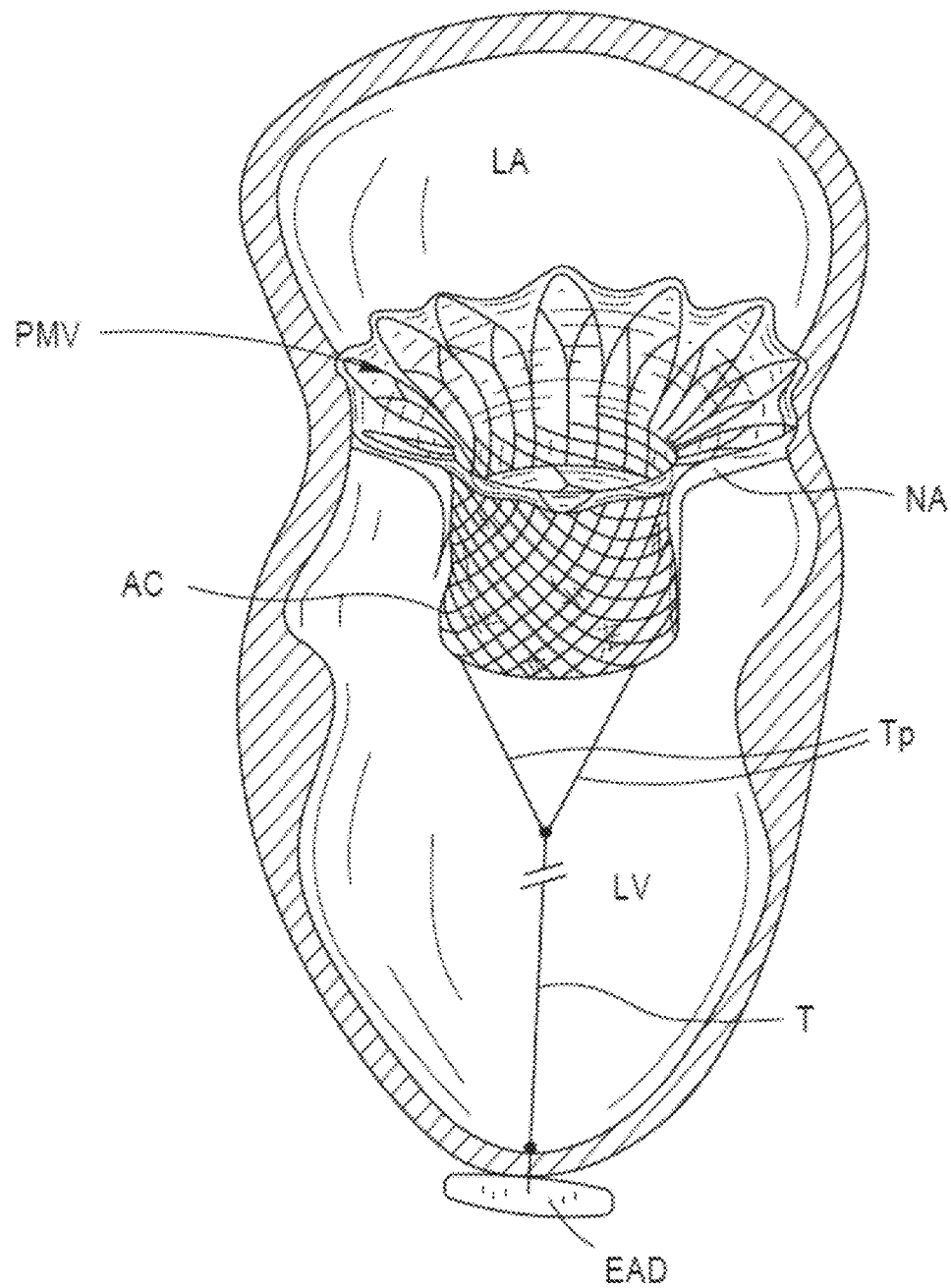
FIG. 1 is a cross-sectional illustration of portion of a heart with a prosthetic mitral valve implanted therein.

Apparatus and methods are described herein for use in the delivery and deployment of a prosthetic heart valve (e.g., a prosthetic mitral valve) into a heart. In some embodiments, a delivery device as described herein can be used to deploy and reposition a prosthetic heart valve. In some embodiments, a delivery device as described herein can include a two-stage controlled deployment mechanism for allowing accurate valve deployment. A delivery device as described herein can include a single 34Fr all-in-one system that can accommodate a variety of valve sizes. In some embodiments, a repositioning and retrieval device is described herein that can be used to reposition and/or retrieve a deployed prosthetic heart valve. The repositioning and retrieval device can include a two-stage controlled capture of a prosthetic valve implanted within a heart to reposition and/or remove/retrieve the prosthetic valve.

Although some embodiments are described herein with reference to a prosthetic mitral valve, it should be understood that the apparatus and methods described herein can be used to deploy, reposition and/or remove other any type of heart valve. For example, the apparatus and methods described herein can be used to deploy, reposition and/or remove a tricuspid heart valve, a pulmonary heart valve or an aortic heart valve. Further, the apparatus and methods described herein can be used from various delivery approaches to the heart, such as, for example, a transapical approach, transatrial, or a transventricular or transvascular approach (e.g., transjugular, transfemoral).

In some embodiments, a dilator device can be coupled to or incorporated within the delivery device. In some embodiments, the dilator device can include a balloon dilator member and be inserted through a port defined in, for example, the handle assembly or the catheter assembly of the delivery device. Such a dilator device is described below with reference to FIGS. 13 and 28-43. Use of a dilator device can help reduce the risk of damaging the prosthetic valve and/or the heart (e.g., the atrium).

As described herein, in some embodiments, a delivery device can include a handle assembly having one or more actuators, a delivery catheter assembly and a valve holding tube. The valve holding tube can be removably coupled to a distal end portion of the handle assembly and removably coupled to a hub of the delivery catheter assembly. In some embodiments, the valve holding tube can be coupled to the handle assembly, and the valve holding tube and handle assembly can be collectively and movably coupled to the delivery catheter. In some embodiments, the valve holding tube can be coupled to the catheter assembly prior to being coupled to the handle assembly. In some embodiments, during use, the valve holding tube is coupled to the handle assembly and to the catheter assembly prior to the catheter assembly being inserted into a heart. In some embodiments, the valve holding tube and handle assembly can be collectively and movably coupled to the delivery catheter assembly after the catheter assembly has been inserted into the heart. A dilator device is also described herein that can optionally be used during a procedure to deliver a prosthetic valve (e.g., prosthetic mitral valve) to the heart and can be received through a lumen of the delivery catheter. The delivery devices described herein can be used to deploy a prosthetic mitral valve into the heart in a controlled manner providing incremental movement of the prosthetic mitral valve within the delivery catheter and into the heart.

In some embodiments, an apparatus includes a catheter assembly, a valve holding tube and a handle assembly. The valve holding tube is releasably couplable to a proximal end portion of the catheter assembly and to a distal end portion of the handle assembly. The handle assembly includes a housing and a delivery rod. The delivery rod is configured to be actuated to move distally relative to the housing to move a prosthetic heart valve disposed within the valve holding tube out of the valve holding tube and distally within a lumen of the elongate sheath of the catheter assembly. The catheter assembly is configured to be actuated to move proximally relative to the housing such that the prosthetic valve is disposed outside of the lumen of the elongate sheath.

In some embodiments, an apparatus includes a loading funnel assembly configured to receive therein a prosthetic heart valve when the valve is in a non-collapsed or biased expanded configuration and a valve holding tube that defines an interior region that is configured to receive a prosthetic heart valve in a collapsed configuration. The valve holding tube has a first end portion configured to be releasably coupled to the loading funnel assembly and a second end portion. The apparatus further includes a handle assembly that includes a handle and a loading leadscrew. The loading leadscrew can be releasably coupled to the second end portion of the valve holding tube. The handle assembly further includes a tether retention mechanism and an actuator knob. The tether retention mechanism can secure a tether extending from a prosthetic heart valve disposed within the funnel assembly in a fixed position relative to the handle assembly. The actuator knob is operatively coupled to the loading leadscrew and the handle such that relative movement between the handle and the loading leadscrew causes the prosthetic valve to be disposed within the valve holding tube.

In some embodiments, an apparatus includes a recapture device that can be used to remove or reposition a prosthetic heart valve deployed within a heart. The recapture device includes an outer sheath, an outer dilator, an inner dilator, and a handle assembly. The outer sheath defines a first lumen and the outer dilator defines a second lumen and is movably disposed at least partially within the first lumen of the outer sheath. The inner dilator is movably disposed at least partially within the second lumen of the outer dilator and includes a distal tip. The handle assembly includes an actuator operatively coupled to the inner dilator and operatively coupled to the outer dilator and a tether retention mechanism to secure to the handle assembly a tether extending from the prosthetic heart valve. The actuator includes a drive mechanism operatively coupled to a first spring coupled to the inner dilator and to a second spring coupled to the outer dilator. When the actuator is actuated, the inner dilator moves proximally relative to the outer dilator when the tether extending from the prosthetic heart valve is secured to the tether retention mechanism such that a first portion of the prosthetic heart valve is pulled to within the second lumen of the outer dilator and moved to a collapsed configuration. The outer dilator can be actuated sequentially after the inner dilator to move the outer dilator proximally relative to the outer sheath such that a second portion of the prosthetic heart valve, distal of the first portion of the prosthetic heart valve, is pulled within the first lumen of the outer sheath and moved to a collapsed configuration.

In some embodiments, a method of delivering a transcatheter mitral valve replacement to the mitral annulus of a heart includes deploying into the mitral annulus a transcatheter mitral valve prosthesis using a delivery device as described herein. The transcatheter mitral valve prosthesis can be made from an expandable metal stent body having valve leaflets disposed therein. The stent body can be covered with a synthetic material or stabilized pericardial tissue and the valve leaflets can be made from stabilized pericardial tissue. The expandable metal stent body can have an optional atrial cuff and the cuff can optionally have a covering made from a synthetic material and/or stabilized pericardial tissue. The transcatheter mitral valve prosthesis can be deployed via catheter in a compressed state and expanded upon ejection from the catheter. The mitral valve prosthesis (also referred to herein as "prosthetic mitral valve" or "prosthetic valve" or "prosthetic heart valve") may include one or more tethers coupled to a proximal end portion of the mitral valve prosthesis.

A distal end of the one or more tethers can be anchored, for example, in the left ventricle. The one or more tethers can be tightened and/or otherwise adjusted to a desired tension prior to fastening the one or more tethers to establish a fixed length and securing the tethers to, for example, an apex region of the heart. Prosthetic mitral valves that can be delivered with the devices and methods disclosed herein can include, for example, those disclosed in International Patent Application Serial Nos. PCT/US14/40188 entitled "Structural Members for Prosthetic Mitral Valves," filed May 30, 2014 ("PCT application '40188"), PCT/US14/44047 entitled "Thrombus Management and Structural Compliance Features For Prosthetic Heart Valves," filed Jun. 25, 2014 ("PCT application '44047"), PCT/US14/58826 entitled "Prosthetic Heart Valve and Systems and Methods for Delivering the Same," filed Oct. 2, 2014 ("PCT application '58826"), and PCT/US16/12305 entitled Prosthetic Mitral Valves and Apparatus and Methods for Delivery of Same" filed Jan. 6, 2016 ("PCT application '12305"), the disclosures of which are incorporated herein by reference.

In some embodiments, a surgical kit can include a delivery device as described herein and accessory components that can be used with the delivery device in a procedure to deliver a transcatheter prosthetic valve as described herein. The delivery device and the accessory components can be disposed within a sterile package. For example, in some embodiments, a kit can include a delivery device and a dilator device and/or a valve loading device as described herein. In some embodiments, a kit can also include a transcatheter valve (e.g., a prosthetic mitral valve) and/or an epicardial pad that can be used to secure the transcatheter valve in position within the heart. In some embodiments, a kit can include a retrieval and repositioning device as described herein.

As used herein, the words "proximal" and "distal" refer to a direction closer to and away from, respectively, an operator of, for example, a medical device. Thus, for example, the end of the medical device closest to the patient's body (e.g., contacting the patient's body or disposed within the patient's body) would be the distal end of the medical device, while the end opposite the distal end and closest to, for example, the user (or hand of the user) of the medical device, would be the proximal end of the medical device.

FIG. 1 is a cross-sectional illustration of the left ventricle LV and left atrium LA of a heart having a transcatheter prosthetic mitral valve PMV deployed therein and an epicardial anchor device EAD securing the prosthetic mitral valve PMV to the apex region of the heart. FIG. 1 illustrates the prosthetic mitral valve PMV seated into the native valve annulus NA and held there using an atrial cuff AC of the prosthetic mitral valve PMV, the radial tension from the native leaflets, and a ventricular tether T secured with attachment portions Tp to the prosthetic mitral valve PMV and to the epicardial anchor EAD. The apparatus and methods described herein can be used in conjunction with the various different types and embodiments of an epicardial anchor device, such as those described in pending International Patent Application No. PCT/US14/49218 entitled "Epicardial Anchor Devices and Methods," ("PCT application '49218") the disclosure of which is incorporated herein by reference in its entirety.

Figure 2:
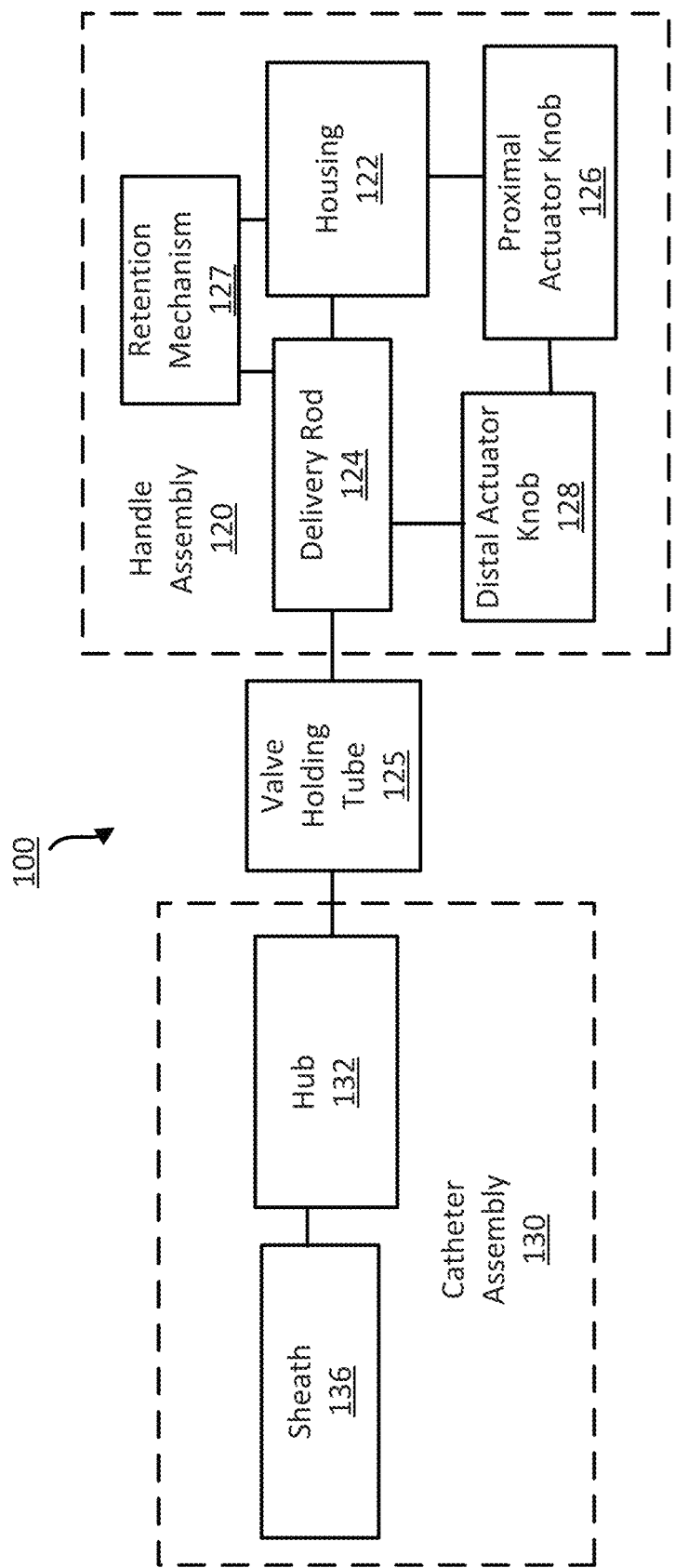
FIG. 2 is a schematic illustration of a delivery device, according to an embodiment.

FIG. 2 is a schematic illustration of a delivery device, according to an embodiment. A delivery device 100 can be used to deliver and deploy a prosthetic heart valve within the heart, such as, for example, a prosthetic mitral valve. The delivery device 100 includes a catheter assembly 130, a handle assembly 120 removably couplable to the catheter assembly 130, and a valve holding tube 125 removably couplable to the handle assembly 120 and to the catheter assembly 130.

The catheter assembly 130 includes a hub 132 and a delivery sheath 136. The delivery sheath 136 defines a lumen (not shown in FIG. 2) through which the valve holding tube 125 can be inserted to deliver a prosthetic valve (not shown in FIG. 2) disposed within the valve holding tube 125 as described in more detail below. In some embodiments, the delivery sheath 136 can be for example, a 34Fr braided sheath. The hub 132 is disposed at a proximal end of the sheath 136 and defines an interior region through which the prosthetic valve is first introduced prior to insertion into the lumen of the sheath 136. In use, the hub 132 remains outside the heart and can provide access to the lumen of the sheath when it is inserted into the heart. The hub 132 can also include a port (not shown in FIG. 2) through which a device, such as a dilator device, can be introduced as described in more detail below.

The handle assembly 120 includes a housing 122, a tether retention and mechanical retention coupler (also referred to herein as "retention mechanism") 127 coupled to the housing 122, a delivery rod 124 extending distally from the housing 122, a proximal actuator knob 126 (also referred to as "proximal actuator" or "first actuator") coupled to the housing 122, and a distal actuator knob 128 (also referred to as "distal actuator" or "second actuator") coupled to the housing. The proximal actuator knob 126 can be operatively coupled to the delivery rod 124 and used to move or push distally within the delivery sheath 136, a prosthetic heart valve that is pre-loaded into the valve holding tube 125 and coupled to the handle assembly 120 as described in more detail below. The distal actuator knob 128 can be operatively coupled to the delivery sheath 136 and used to actuate or move the delivery sheath 136 during deployment of the prosthetic valve into the heart. For example, the prosthetic valve can first be moved distally by the delivery rod 124 until it is positioned within a distal end portion of the delivery sheath 136, and then to deploy the prosthetic valve within the heart, the delivery sheath 136 is moved proximally, disposing the prosthetic valve outside of the delivery sheath 136 and within the heart. The distal actuator 128 can provide a slow, controlled deployment of the prosthetic valve. In some embodiments, the delivery sheath 136 can also be actuated to recapture a prosthetic heart valve that has already been deployed within a heart such that the prosthetic valve can be repositioned or removed. For example, upon initial deployment of the valve within the heart, it may be desirable to reposition the valve. The delivery device 100 can be actuated to partially recapture a proximal portion of the valve to make adjustments to its position. For example, the delivery sheath can be actuated to move distally to recapture a portion of the valve, then after the valve has been repositioned, the sheath can be actuated to move proximally again to release the valve. The delivery rod 124 can also be used to recapture a portion of the prosthetic valve. For example, the delivery rod 124 can define a lumen and can be actuated to move distally such that a portion of the prosthetic valve is recaptured within the lumen of the delivery rod 124. Further details of the delivery and deployment of a prosthetic heart valve using the delivery device are provided below with reference to specific embodiments.

The valve holding tube 125 can contain or hold a prosthetic mitral valve (not shown in FIG. 2) in a compressed configuration within an interior lumen of the valve holding tube 125. As discussed with respect to FIG. 3, in some embodiments, a valve loading device 160 can be used to load the prosthetic valve into the valve holding tube 125 such that the prosthetic valve is compressed in a controlled manner to a desired compressed size and shape. Such a valve loading device is also described in more detail below with reference to a specific embodiment (see, e.g., FIGS. 18-24). The valve holding tube 125 (with the prosthetic mitral valve therein) can be coupled to a distal end portion of the handle assembly 120. For example, the valve holding tube 125 can be coupled to the handle assembly 120 such that a portion of the distal end portion of the delivery rod 124 of the handle assembly 120 can be received within an interior region of the valve holding tube 125. In some embodiments, the valve holding tube 125 and the handle assembly 120 can include mating quick connect couplers to releasably couple the valve holding tube 125 to the handle assembly 120. Prior to coupling the valve holding tube 125 to the delivery device 220, a tether (not shown) coupled to the prosthetic valve (within the valve holding tube 125) can be threaded through a lumen defined by the delivery rod 124 and extend proximally out of the handle assembly 120.

The valve holding tube 125 can have various lengths to accommodate various different procedures to deliver the prosthetic heart valve to the heart. For example, in some embodiments, the valve holding tube 125 can have a length of between about 2 cm and 15 cm. In some embodiments, the sheath 136 can have a length of about 12 cm to about 38 cm. In some embodiments, the sheath 136 can have a length of about 50 cm to about 150 cm.

In some embodiments, the prosthetic heart valve (e.g., mitral valve) can be delivered apically, i.e. delivered through the apex of the left ventricle of the heart, using the delivery device 100 described herein. With such apical delivery, the delivery device 100 can access the heart and pericardial space by intercostal delivery. In this case, the sheath 136 can have a length of, for example, 12-38 cm.

In another delivery approach, the delivery device 100 can deliver the prosthetic heart valve using either an antegrade or retrograde delivery approach without requiring the use of a rigid tube system that is commonly used in such procedures. In another embodiment, the delivery device 100 can access the heart via a trans-septal approach. In either case, where a long distance must be travelled, the valve holding tube 125 can have a length of, for example, 60-150 cm.

The tether retention mechanism 127 can be coupled to a proximal end portion of the housing 122 and can be used to couple a tether(s) extending from a prosthetic valve to the handle assembly 120. One or more tethers coupled to the prosthetic valve can extend through the handle assembly 120 and can also be inserted or threaded through the retention mechanism 127. In some embodiments, the retention mechanism 127 includes a spring mechanism that can be used to secure the tether to the tether retention mechanism 127 and thus to the handle assembly 122. The spring mechanism can be actuated to deflect the tether (e.g., bend Nitinol wire of tether) and apply a constant or substantially constant force (e.g., tension) on the tether during deployment. The spring mechanism can also allow for adjustment of the force applied to the prosthetic valve during removal of the delivery device after deployment of a prosthetic valve. The tension on the tether can be released to allow movement of the prosthetic valve, and then re-tensioned to secure the tether and prosthetic valve in the new position. In some embodiments, the tether retention mechanism 127 includes a tether pinning mechanism. In such an embodiment, a pinning member can be used to pierce the tether to secure the tether to the retention mechanism 127.

The tether retention mechanism 127 can provide additional safety during a deployment procedure in that, with a compressed valve under great pressure, release from a catheter can launch the prosthetic valve, for example, a distance of many feet. However, with the retention mechanism 127 provided herein and the ability to provide a slow calibrated deployment, the user can control the deployment to prevent the valve from inadvertently being projected from the sheath 136.

In one example use to deliver and deploy the prosthetic mitral valve within a heart, the sheath 136 of the catheter assembly 130 can be inserted through the epicardial surface of the patient's heart and extended through the left ventricle and to the left atrium of the heart such that the hub 132 is disposed on the outside of the heart near or in contact with the epicardial surface. In some embodiments, prior to introducing the sheath 136 into the heart, a guidewire (not shown) is extended into the heart and to the left atrium. The sheath 136 can then be threaded over the guidewire to be inserted into the heart. For example, the guidewire can be extended through the sheath 136 and out a port disposed on the hub 132. In some embodiments, prior to inserting the sheath 136 into the heart, a dilator device (not shown in FIG. 2) can be inserted through the port of the hub 132 and through the lumen of the sheath 136, such that a tapered distal end portion of the dilator device extends outside a distal end of the sheath 136. The tapered distal end of the dilator device can provide a lead-in for the sheath 136 and help open or enlarge the entry opening at the epicardial surface and through the mitral annulus. An example dilator device is described in U.S. patent application Ser. No. 14/527,382, filed Oct. 29, 2014 ("the '382 application"), the entire disclosure of which is incorporated herein by reference. Other embodiments of a dilator device are described herein with reference to FIGS. 13 and 28-43. When the sheath 136 is placed at the desired position within the heart, the dilator device can be removed leaving the sheath 136 within the heart. Further details of a dilator device are described below.

As described above, the valve holding tube 125 (with a prosthetic valve disposed therein) can be coupled to a distal end portion of the handle assembly 120. The tether extending from the valve can be threaded through the delivery rod 124 and extend out a proximal end of the handle assembly 120. With the valve holding tube 125 coupled to the distal end portion of the handle assembly 120, and the distal end portion of the delivery rod 124 disposed within the valve holding tube 125, the valve holding tube 125 can be inserted into the hub 132 of the catheter assembly 130 and coupled to the hub 132. In some embodiments, O-rings (not shown in FIG. 1) on the valve holding tube 125 can maintain the position of the valve holding tube 125 within the hub 132. For example, in some embodiments, the valve holding tube 125 and the hub 132 can include mating quick connect couplers that include O-rings, to releasably couple the valve holding tube 125 to the hub 132.

With the valve holding tube 125 coupled to the catheter assembly, the proximal actuator knob 126 can then be actuated (e.g., rotated) to move the delivery rod 124 distally such that a distal end of the delivery rod 124 pushes the prosthetic valve out of the valve holding tube 125 and into a distal end portion of the delivery sheath 136. As the delivery rod 124 moves distally, the delivery rod 124 moves relative to the housing 122 of the handle assembly 120, and the valve holding tube 125 remains stationary relative to the housing 122, allowing the delivery rod 124 to push the prosthetic valve out of the valve holding tube 125 and into the delivery sheath 136. The tether can then be secured to the retention mechanism 127, securing the valve to the housing 122. The distal actuator knob 128 can then be actuated to retract or move proximally the delivery sheath 136 (and the valve holding tube 125 coupled thereto via the hub 132) relative to the housing 122 such that the prosthetic valve is left disposed outside of the delivery sheath 136 and within the left atrium of the heart or within the annulus of the native mitral valve. After the prosthetic valve has been deployed, the prosthetic valve can be maneuvered and repositioned as needed and then the tether can be released from the retention mechanism 127. The tether can then be secured to an epicardial surface of the heart with, for example, an epicardial pad (e.g., EAD in FIG. 1) as described above.

In an alternative example procedure, rather than first inserting the catheter assembly 130 into the heart, and then coupling the valve holding tube 125 and handle assembly 120 thereto, the valve holding tube 125 can be coupled to both the handle assembly 120 and to the catheter assembly 130 prior to the catheter assembly 130 being inserted into the heart. In such a procedure, the same steps described above can be employed for inserting the catheter assembly 130 into the heart, such as, for example, inserting the catheter assembly 130 over a guidewire and/or using a dilator device as described above. The delivery device 100 can then be actuated in the same manner as described above to first move the prosthetic valve distally within the delivery sheath 136 and then move the delivery sheath 136 proximally to dispose the prosthetic valve in the heart.

Figure 3:
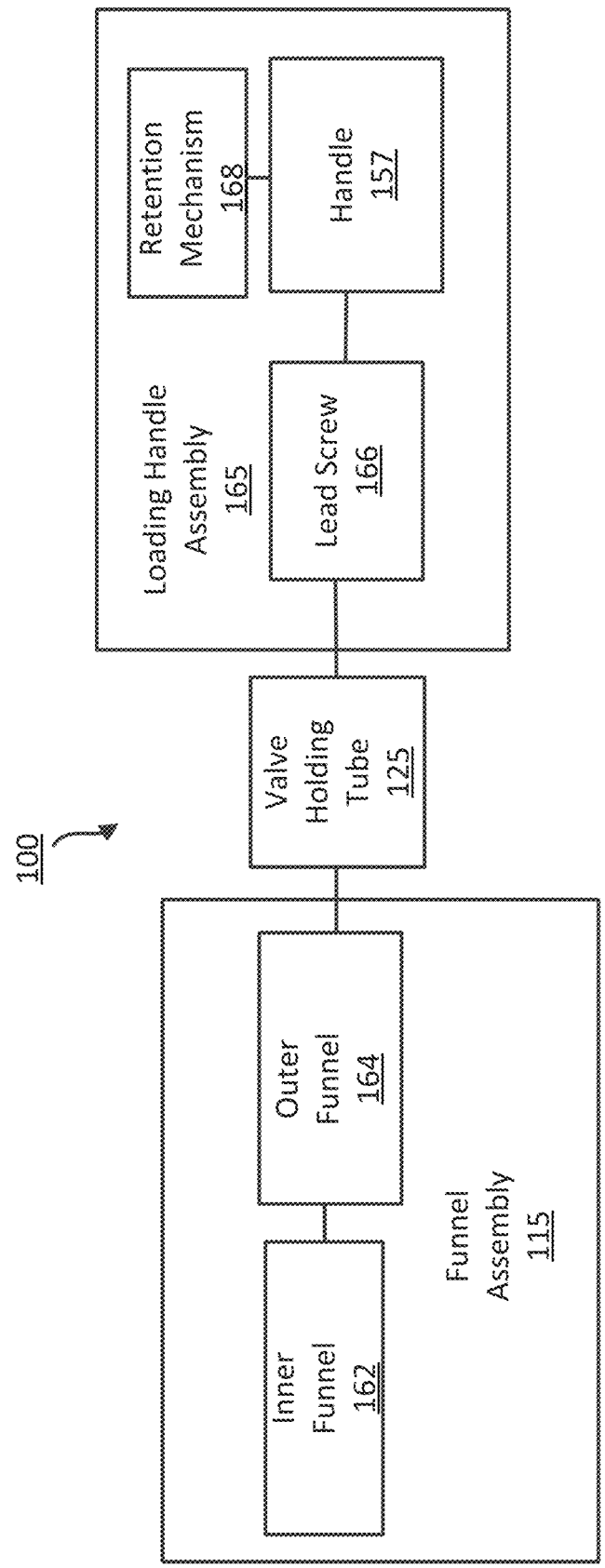
FIG. 3 is a schematic illustration of a valve loading device, according to an embodiment.

FIG. 3 is a schematic illustration of a valve loading device 160. The valve loading device 160 includes a funnel assembly 115, a loading handle assembly 165 and the valve holding tube 125 described above. Prior to coupling the valve holding tube 125 to the handle assembly 120 and catheter assembly 130, a prosthetic valve (also referred to herein as "valve") is loaded into the valve holding tube 125 using the valve loading device 160. The valve is first placed within the funnel assembly 115 to move the valve from a biased expanded configuration to a collapsed configuration. The funnel assembly 115 includes an outer funnel 164 and an inner funnel or centering cone 162. The valve is placed within the outer funnel 164 and then the inner funnel is coupled to the outer funnel 164 sandwiching the valve therebetween and collapsing the valve to a desired shape and configuration in a controlled manner. The valve holding tube 125 can be releasably coupled to the funnel assembly 115 and to the loading handle assembly 165 via quick connect couplers in a similar manner as how the valve holding tube 125 is coupled to the handle assembly 120 and catheter assembly 130 described above.

The loading handle assembly 165 includes a handle 157 (also referred to as "main loading knob" or "actuator"), a retention mechanism 168 for securing a tether coupled to the valve, and a loading leadscrew 166 operatively coupled to the handle 157. With the valve holding tube 125 coupled to the funnel assembly 115 and to the loading handle assembly 165, and with the tether extending from the valve secured to the retention mechanism 168, the valve loading device 160 can be actuated to move the valve from a first position in which it is disposed within the funnel assembly to a second position in which the valve is disposed within the valve holding tube 125. More specifically, the handle 167 can be rotated, which in turn moves the leadscrew relative to the handle 167, which in turn moves the valve holding tube 125 and funnel assembly 115 away from the handle 167. Because the valve is in a fixed position (i.e., is stationary) relative to the handle 167 during actuation (through the securement of the tether to the retention mechanism 168), the funnel assembly 115 is moved away from the handle, and the valve holding tube 125 is moved over the valve, disposing the valve within an interior region of the valve holding tube 125. Details regarding the various components and operation of the valve loading device 160 are described below with respect to FIGS. 18-25 and valve loading device 560.

FIGS. 4-12 illustrate a delivery device according to one embodiment. A delivery device 200 includes a catheter assembly 230, a handle assembly 220 removably couplable to the catheter assembly 230 and a valve holding tube 225 removably couplable to the handle assembly 220 and the catheter assembly 230. The delivery device 200 can include the same or similar components and features, and can function the same as or similar to the delivery device 100 described above. The delivery device 200 can be used to deliver and deploy a prosthetic heart valve within the heart, such as, for example, a prosthetic mitral valve (not shown) as described above for the previous embodiment.

The catheter assembly 230 includes a hub 232 and a delivery sheath 236. The delivery sheath 236 defines a lumen 221 (FIG. 9) into which a prosthetic valve (not shown) pre-disposed within an interior region of the valve holding tube 225 can be moved during delivery of the prosthetic valve. The hub 232 is disposed at a proximal end of the sheath 236 and defines an interior region through which the prosthetic valve is first introduced prior to insertion into the lumen of the sheath 236. In use, the hub 232 remains outside the heart and can provide access to the lumen of the sheath 236 when it is inserted into the heart. The hub 232 also includes a port 237 through which, various devices, such as for example, a dilator device (not shown) can be inserted and used during the delivery of a prosthetic heart valve as described in more detail with respect to the embodiment of FIG. 13. Other embodiments of a dilator device are described below with respect to FIGS. 28-43, which can be used with the delivery device 200. The port 237 can also be used to receive a guidewire therethrough. For example, a guidewire can be threaded through a distal end of the delivery sheath 236, into the interior of the hub 232, and out through the port 237.

The handle assembly 220 includes a housing 222, a tether retention mechanism 227 coupled to the housing 222, a delivery rod 224 coupled to the housing 222, a proximal actuator knob 226 (also referred to as "first actuator" or "proximal actuator") coupled to the housing 222, and a distal actuator knob 228 (also referred to as "second actuator" or "distal actuator") coupled to the housing 222. A deployment travel window 223 is disposed on the housing 222 and can be used to view the progress of the delivery of the prosthetic valve. For example, the delivery rod 224 can include markings that are visible through the deployment travel window. The markings can be, for example, labeled with numbers or letters, or can be color coded. The markings can indicate the progress or distance the valve has traveled distally during deployment of the valve. Markings can also be included that indicate the movement proximally of the delivery sheath during deployment of the valve.

The proximal actuator knob 226 can be used to move or push distally within the delivery sheath 236, a prosthetic heart valve (not shown) that is pre-loaded into the valve holding tube 225 and coupled to the handle assembly 220. For example, the proximal actuator knob 226 can be operatively coupled to the delivery rod 224 and can be used to move the delivery rod 224 distally within the delivery sheath 236 relative to the housing 222 such that the delivery rod 224 engages the prosthetic heart valve and moves (e.g., pushes) the prosthetic heart valve distally within the delivery sheath 236 until the prosthetic heart valve is disposed within a distal end portion of the delivery sheath 236. In this embodiment, the proximal actuator 226 is rotated, which in turn causes the rod 224 to move relative to the housing 222. When deploying a valve, the valve holding tube 225 is secured in a fixed relation to the housing 222, and thus, does not move relative to the housing 222 when the rod 224 is actuated. This allows the rod 224 to push the valve distally out of the valve holding tube 225 and into the hub 232 and then within a distal end portion of the delivery sheath 236. With the valve disposed within a distal end of the delivery sheath 236, the tether can be secured to the housing 222 via the retention mechanism 227.

Figure 7:
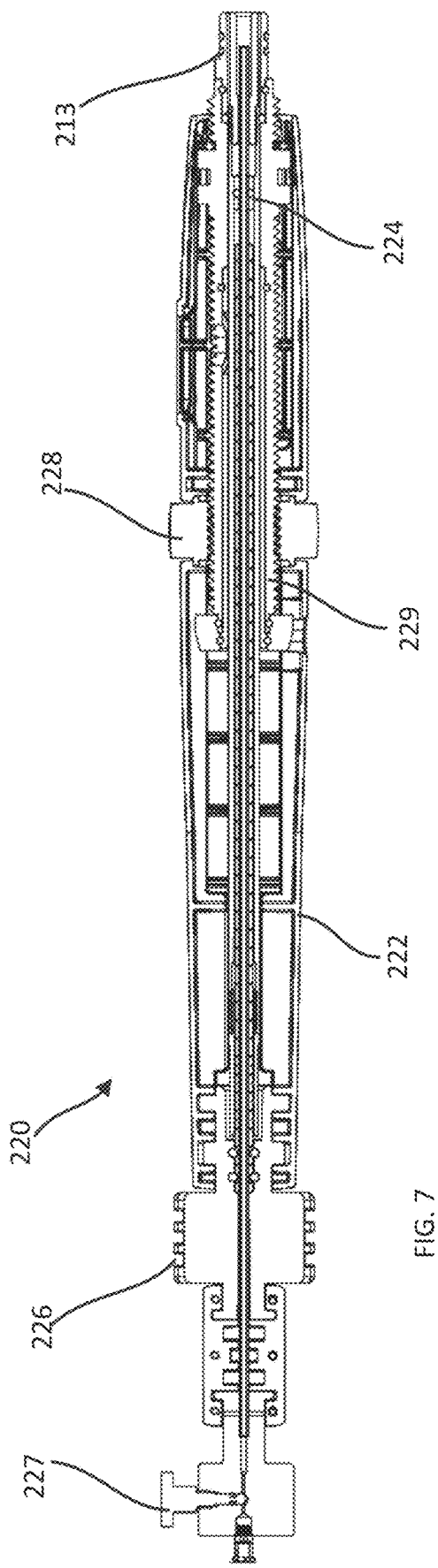
FIG. 7 is a side cross-sectional view of the handle assembly of FIG. 6.
Figure 8:
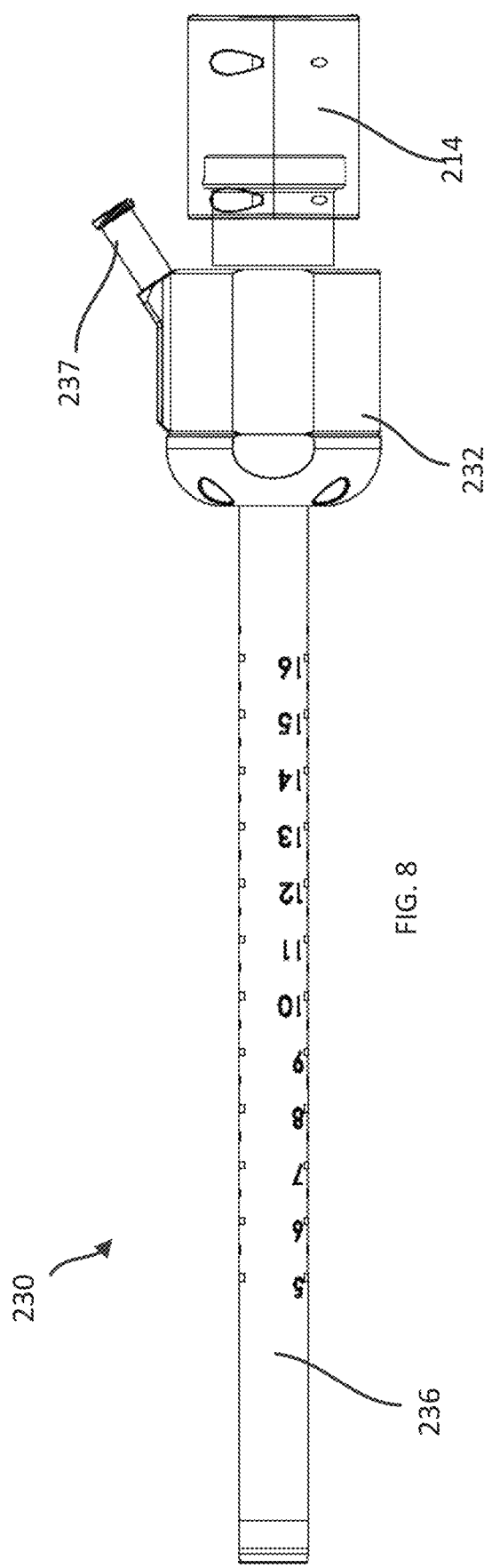
FIG. 8 is a side view of a catheter assembly of the delivery device of FIG. 4.
Figure 9:
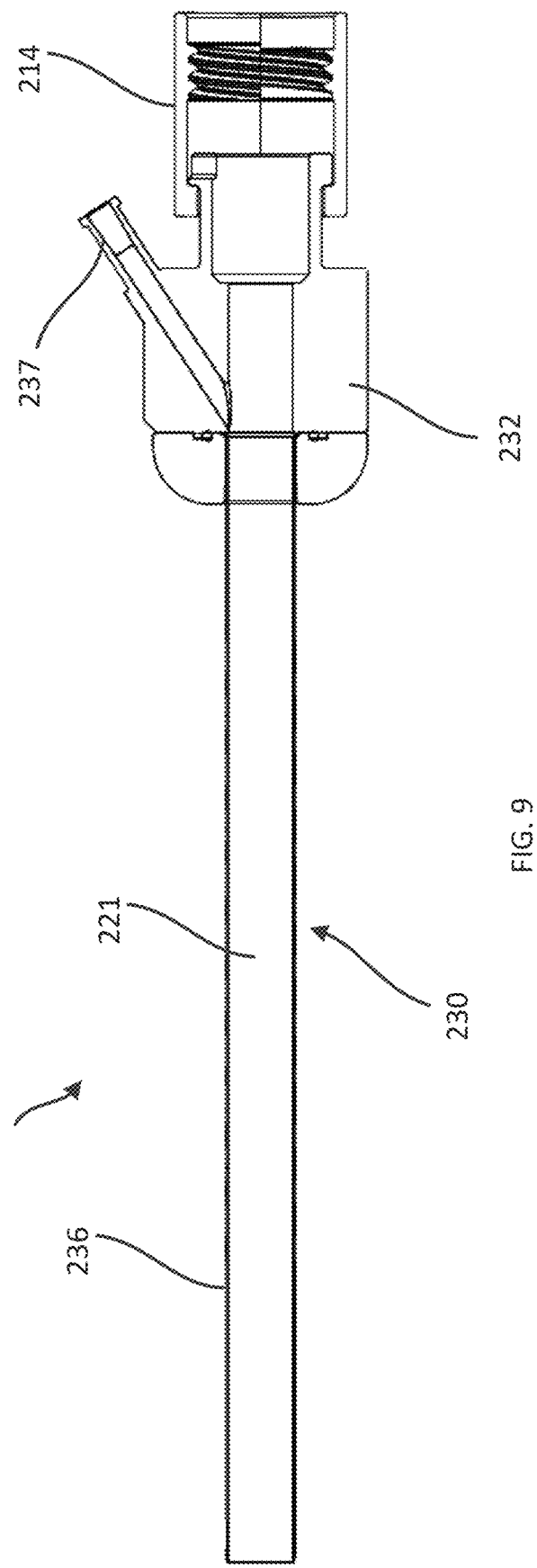
FIG. 9 is a side cross-sectional view of the catheter assembly of FIG. 8.
Figure 10:
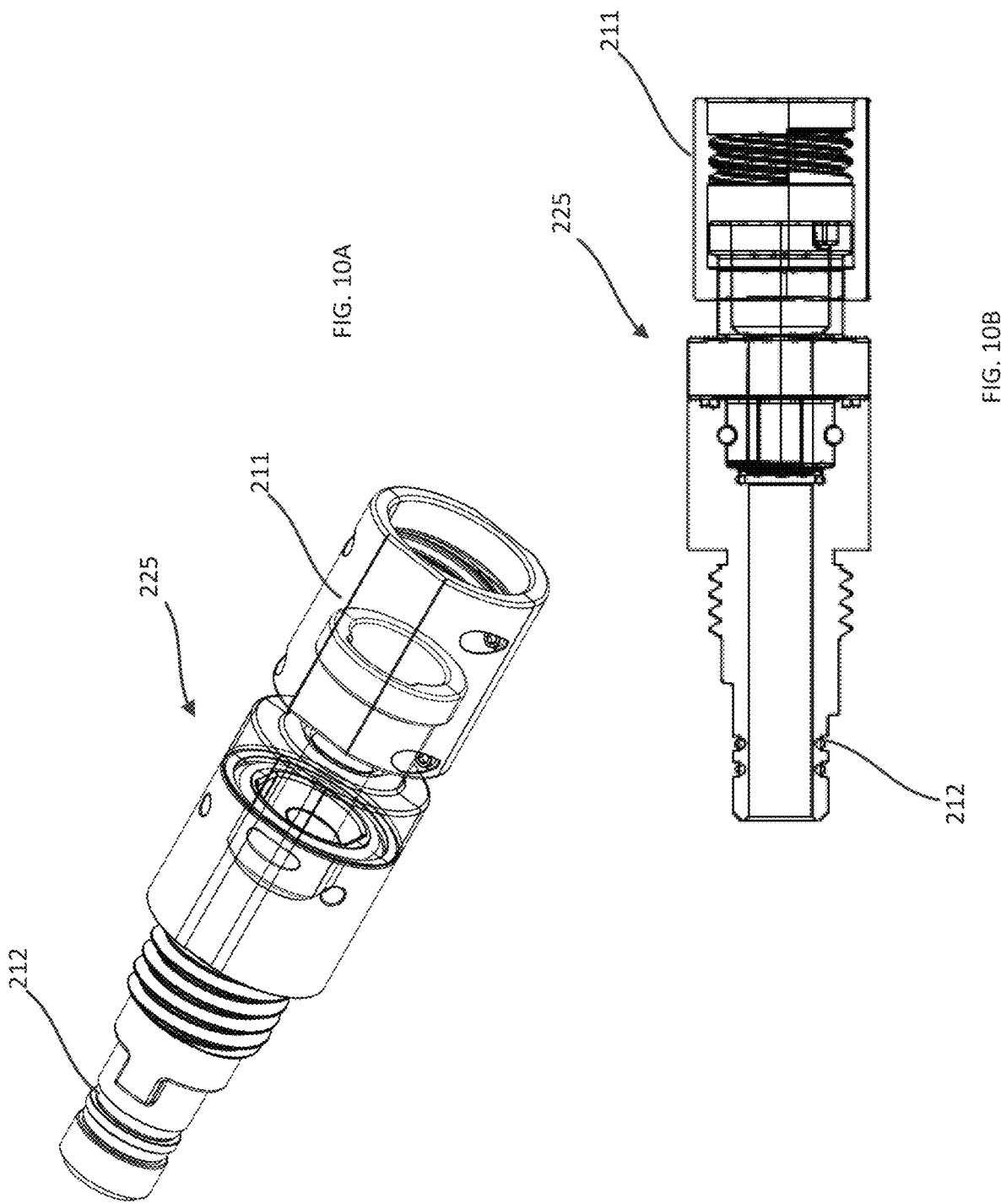
FIG. 10A is a perspective view of a valve holding tube of the delivery device of FIG. 4.
FIG. 10B is a side cross-sectional view of the valve holding tube of FIG. 10A.

The distal actuator knob 228 can be operatively coupled to the delivery sheath 236 and used to actuate or move the delivery sheath 236 during deployment of the prosthetic valve into the heart. In this embodiment, as shown in FIG. 7, the distal actuator knob 228 is coupled to a leadscrew 229, which in turn is coupled to the valve holding tube 225. Thus, when the valve holding tube 225 is coupled to the hub 232, the leadscrew 229 can be actuated to move the valve holding tube 225 and the catheter assembly 230 relative to the housing. For example, as described above, with the prosthetic valve disposed within the delivery sheath 236, to deploy the prosthetic valve into the heart, the delivery sheath 236 is moved proximally relative to the housing 222 (by actuating the distal actuator knob 228) disposing the prosthetic valve outside of the delivery sheath 236 and within the heart.

The delivery sheath 236 can also be actuated to partially recapture a prosthetic heart valve that has already been deployed within a heart such that the prosthetic valve can be repositioned. For example, after the prosthetic valve has been deployed as described above, if it is determined that the prosthetic valve should be repositioned, the actuator knob 228 can be actuated in an opposite direction to move the leadscrew 229 distally, causing the delivery sheath 236 to move distally back over a proximal portion of the prosthetic valve. The delivery device 200 can then be maneuvered to position the prosthetic valve in a desired location, and then the actuator knob 228 can be actuated to move the delivery sheath 236 proximally, again releasing the prosthetic valve from the delivery sheath 236. Further, as described previously, the delivery rod 224 can be actuated by the actuator knob 226 to move distally to recapture a portion of the prosthetic valve within the lumen of the delivery rod 224.

As described above for the previous embodiment, the valve holding tube 225 (see, e.g., FIGS. 10A and 10B) can contain or hold a prosthetic mitral valve (not shown) in a compressed configuration within an interior lumen of the valve holding tube 225. As described above for FIG. 3, and described below with respect to FIGS. 18-25, a valve loading device can be used to pre-load the prosthetic valve into the valve holding tube 225 such that the prosthetic valve is compressed in a controlled manner to a desired compressed size and shape. The valve holding tube 225 (with the prosthetic mitral valve therein) can be removably coupled to a distal end portion of the handle assembly 220 and removably coupled to the hub 232 of the catheter assembly 230.

Figure 5:
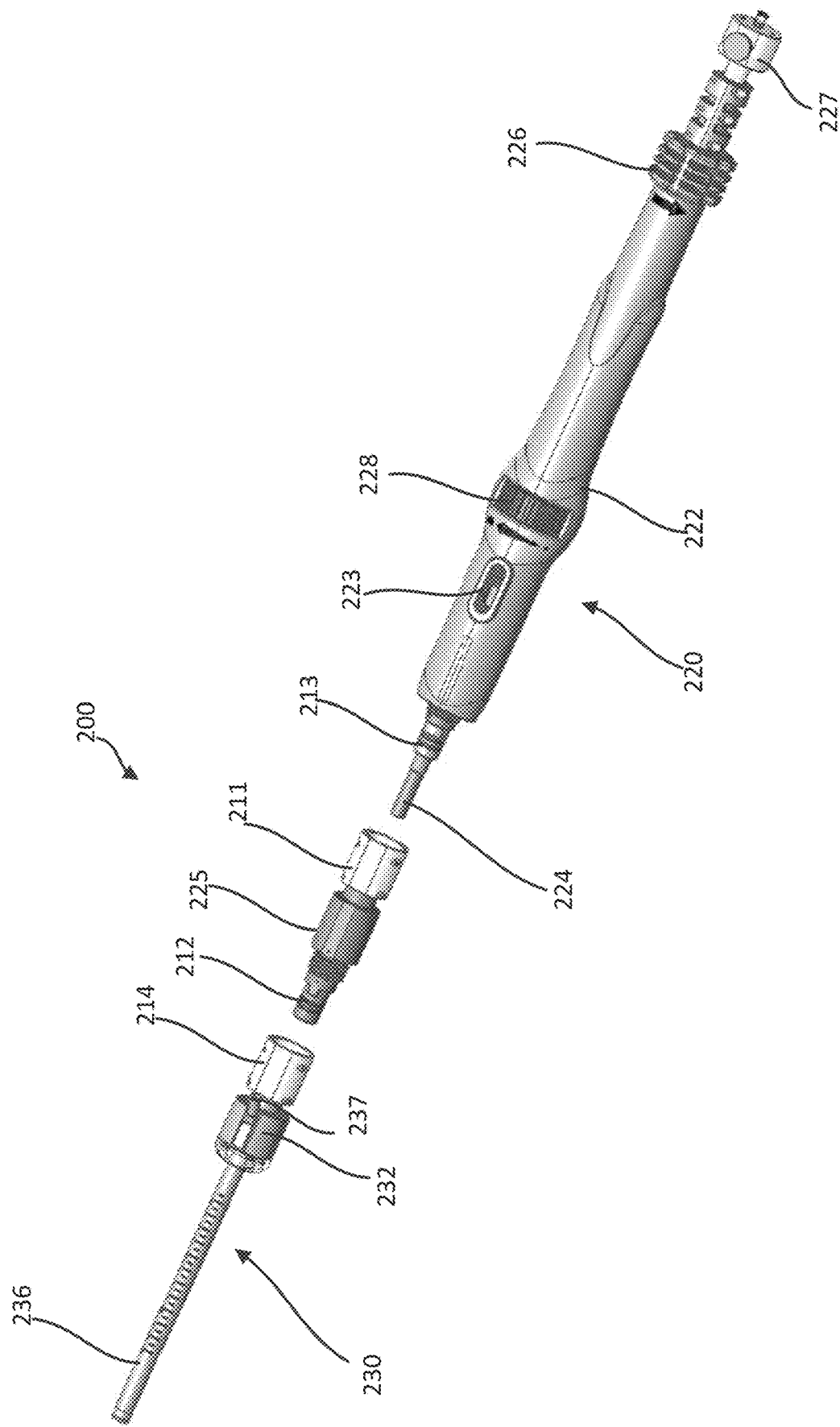
FIG. 5 is an exploded view of the delivery device of FIG. 4.
Figure 6:
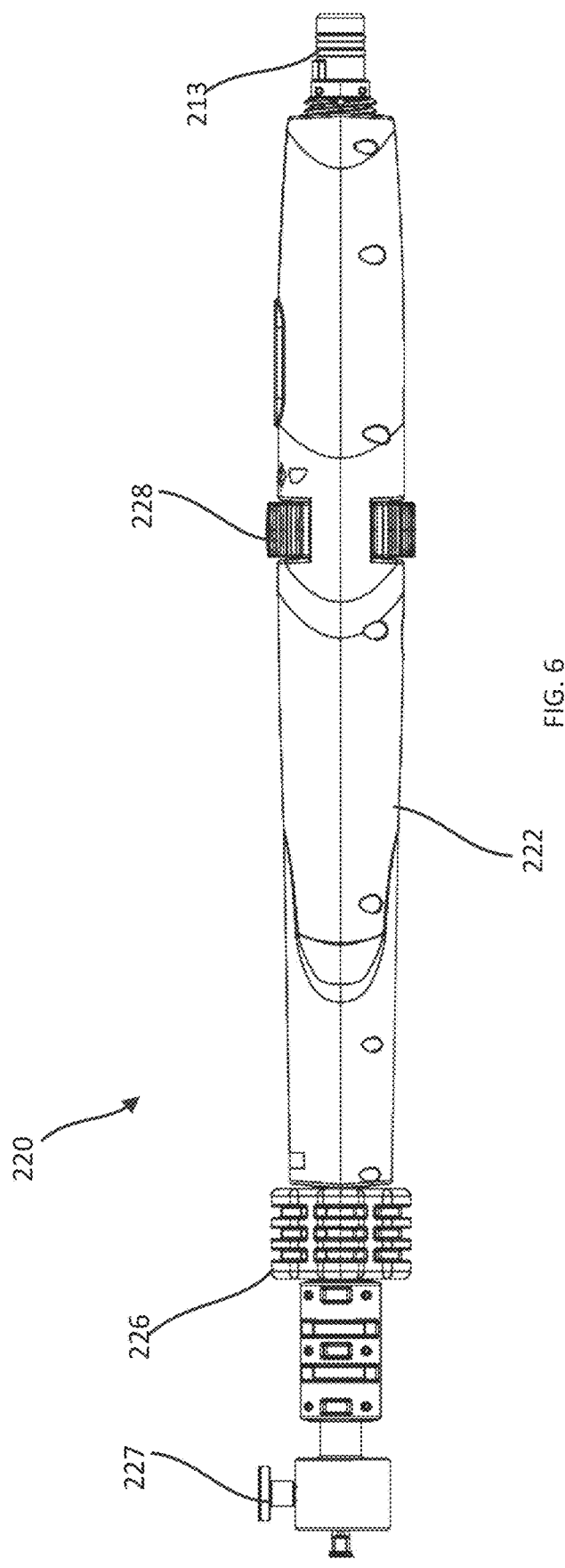
FIG. 6 is a side view of a handle assembly of the delivery device of FIG. 4.

For example, as shown, for example, in FIG. 5, the valve holding tube 225 can include a first quick connect coupler 211 (a female connector in this embodiment) and a second quick connect coupler 212 (a male connector in this embodiment). The first quick connector 211 can be matingly coupled to a quick connect coupler 213 (a male connector in this embodiment) disposed at the distal end portion of the handle assembly 220. Similarly, the second quick connect coupler 212 of the valve holding tube 225 can be matingly coupled to a quick connect coupler 214 (a female connector in this embodiment) disposed on the hub 232 of the catheter assembly 230. The quick connect couplers can include O-rings to maintain the position of the valve holding tube 225 to the handle assembly 220 and to the catheter assembly 230. The quick connect couplers can be a variety of different types of suitable couplers/connectors. For example, the quick connect couplers can be a bayonet connector or ¼ turn connector. It should be understood that in alternative embodiments, the male and female couplers can be reversed (e.g., coupler 211 of valve holding tube 225 can be a male coupler that can be matingly coupled to a female coupler 213 of the handle assembly). With the valve holding tube 225 coupled to the handle assembly, a distal end portion of the delivery rod 224 of the handle assembly 220 can be received within an interior region of the valve holding tube 225. Prior to coupling the valve holding tube 225 to the delivery rod 224, a tether (not shown) coupled to the prosthetic valve (within the valve holding tube 225) can be threaded through a lumen defined by the delivery rod 224 and extend proximally out of the handle assembly 220.

The valve holding tube 225 can be configured the same as or similar to, and function the same as or similar to the valve holding tube 125 described above. For example, the valve holding tube 225 can have various lengths to accommodate various different procedures to deliver the prosthetic heart valve to the heart. The retention mechanism 227 can be coupled to a proximal end portion of the housing 222. In this embodiment, the retention mechanism 227 includes a tether pinning member that can be configured to pierce through the tether and secure the tether to the retention mechanism 227.

In use to deliver and deploy a prosthetic mitral valve within a heart, the valve holding tube 225 can be coupled to the handle assembly 220 and to the catheter assembly 230 via the quick connect couplers described above. For example, the valve holding tube 225 can be inserted into the hub 232 of the catheter assembly 230 and the quick connect couplers 212 and 214 can maintain the position of the valve holding tube 225 within the hub 232. Similarly, the quick connect couplers 211 and 213 can maintain the position of the valve holding tube 225 relative to the handle assembly 220. The delivery sheath 236 of the catheter assembly 230 can be inserted through the epicardial surface of the patient's heart and extended through the left ventricle and to the left atrium of the heart such that the hub 232 is disposed on the outside of the heart near or in contact with the epicardial surface. As described above, in some embodiments, prior to introducing the sheath 236 into the heart, a guidewire is extended into the heart and to the left atrium. The sheath 236 can then be threaded over the guidewire to be inserted into the heart. In some embodiments, prior to inserting the sheath 236 into the heart, a dilator device (not shown) (see, e.g., dilator device 354 in FIG. 13, and dilator devices 834 and 934 described below) can be used as described above to provide a tapered distal insertion tip for insertion of the delivery device 200 into the heart of a patient. As described above for delivery device 100, in an alternative procedure, the catheter assembly 230 can first be inserted into the heart, prior to the valve holding tube 225 being coupled thereto.

Figure 4:
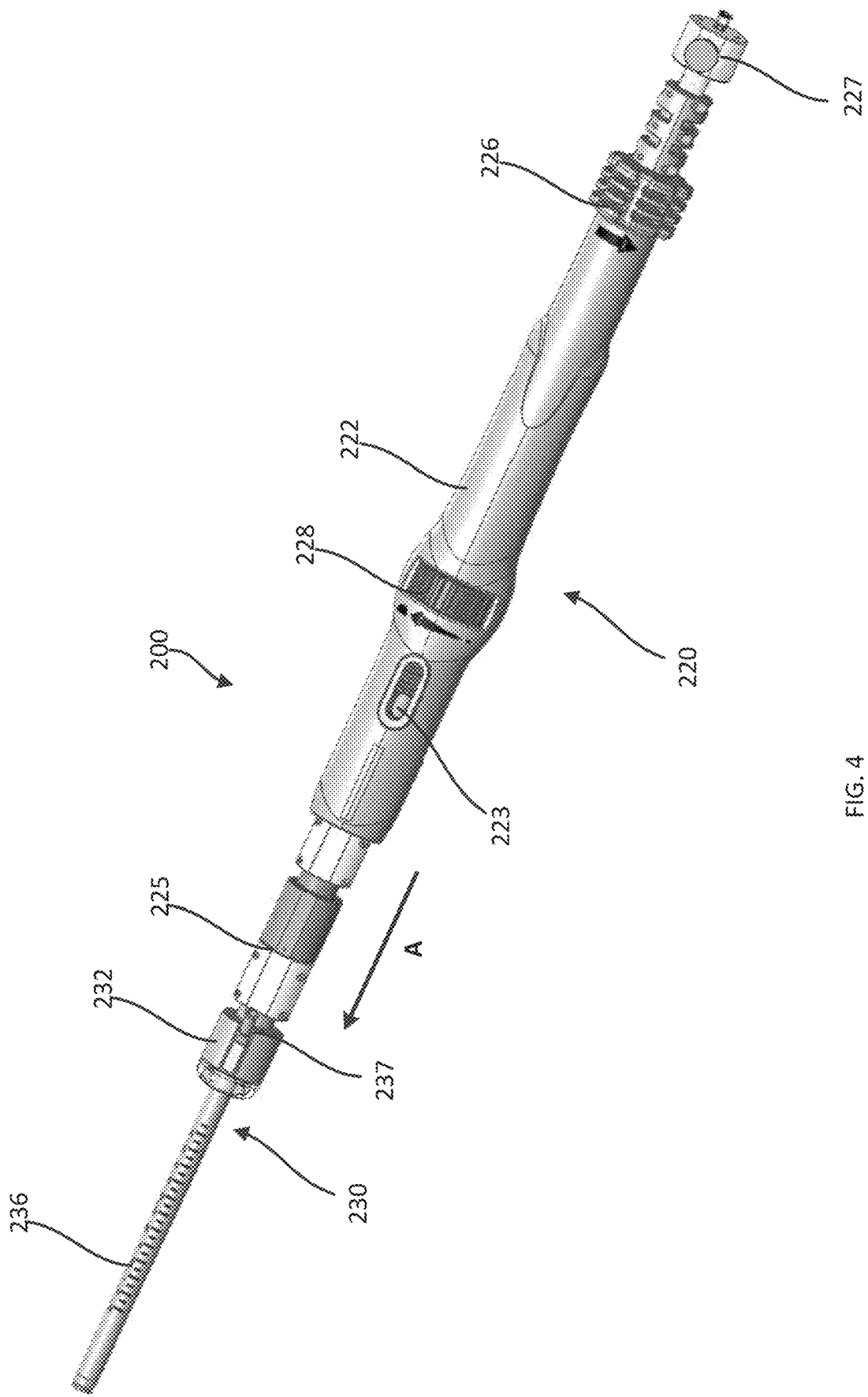
FIG. 4 is a top view of a delivery device, according to an embodiment.
Figure 11:
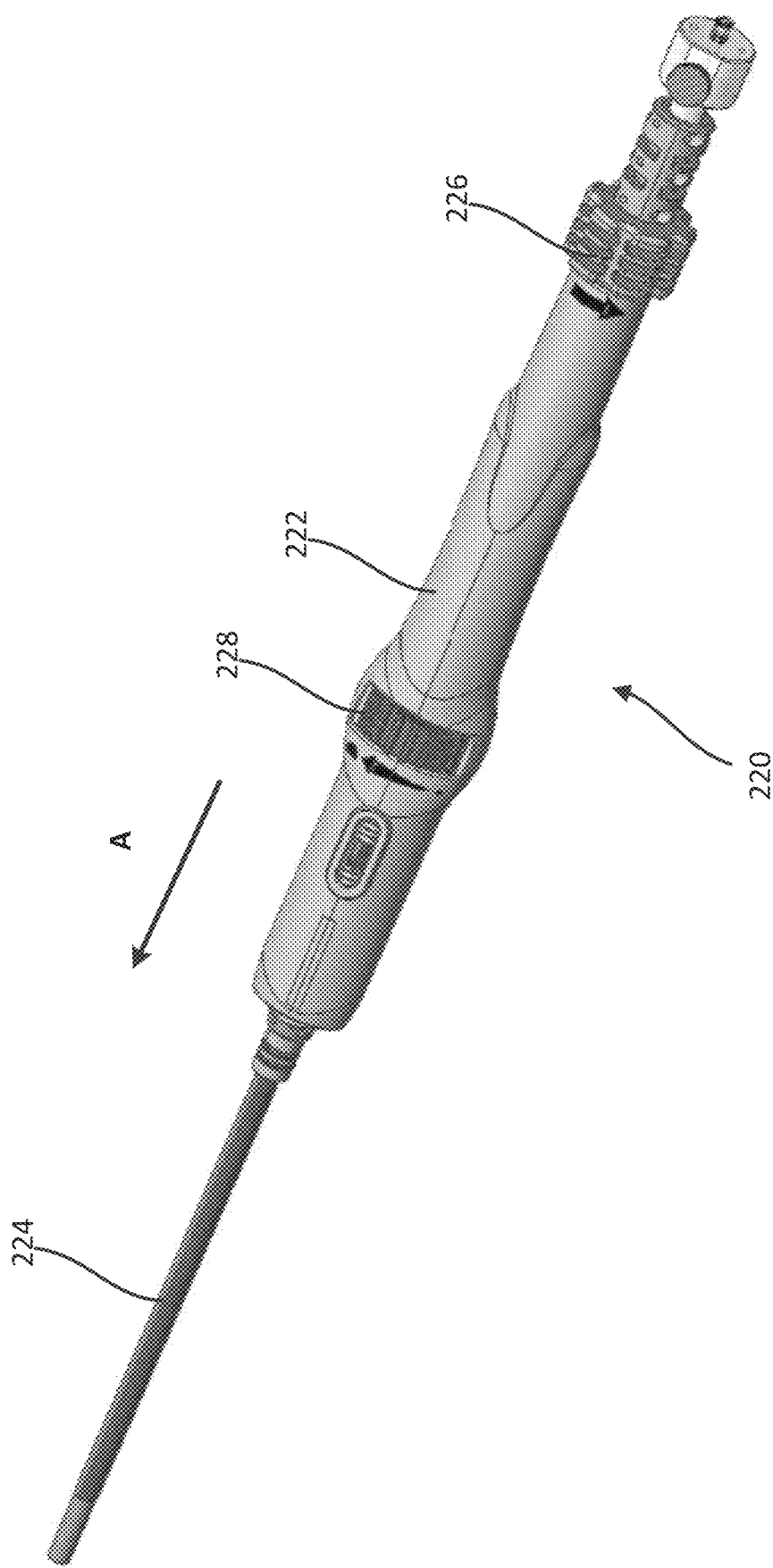
FIG. 11 is a top view of the handle assembly of the delivery device of FIG. 4 illustrating the delivery rod actuated distally.
Figure 12A:
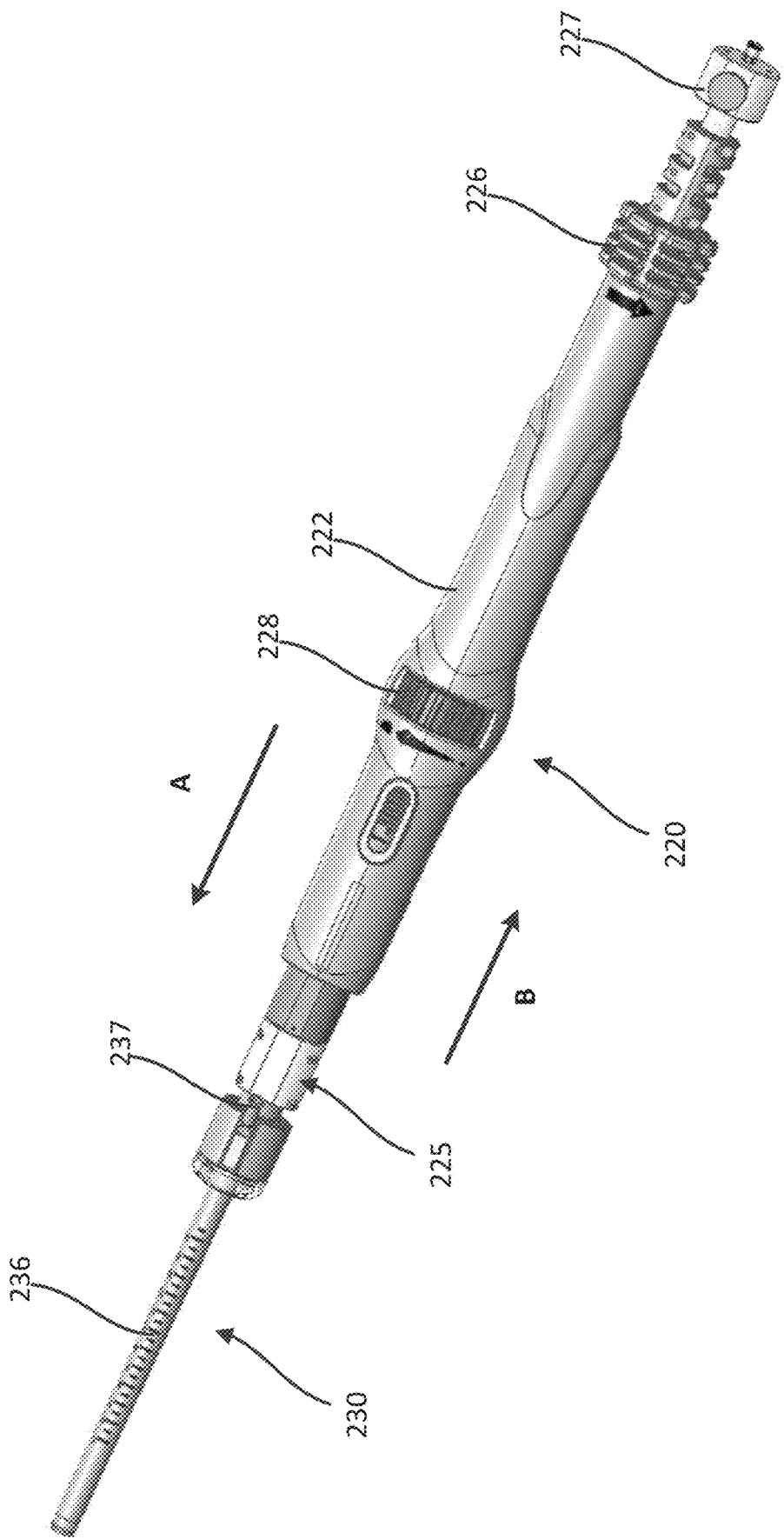
FIG. 12A is a top view of the delivery device of FIG. 4 shown with the delivery sheath in a first partially actuated position.
Figure 12B:
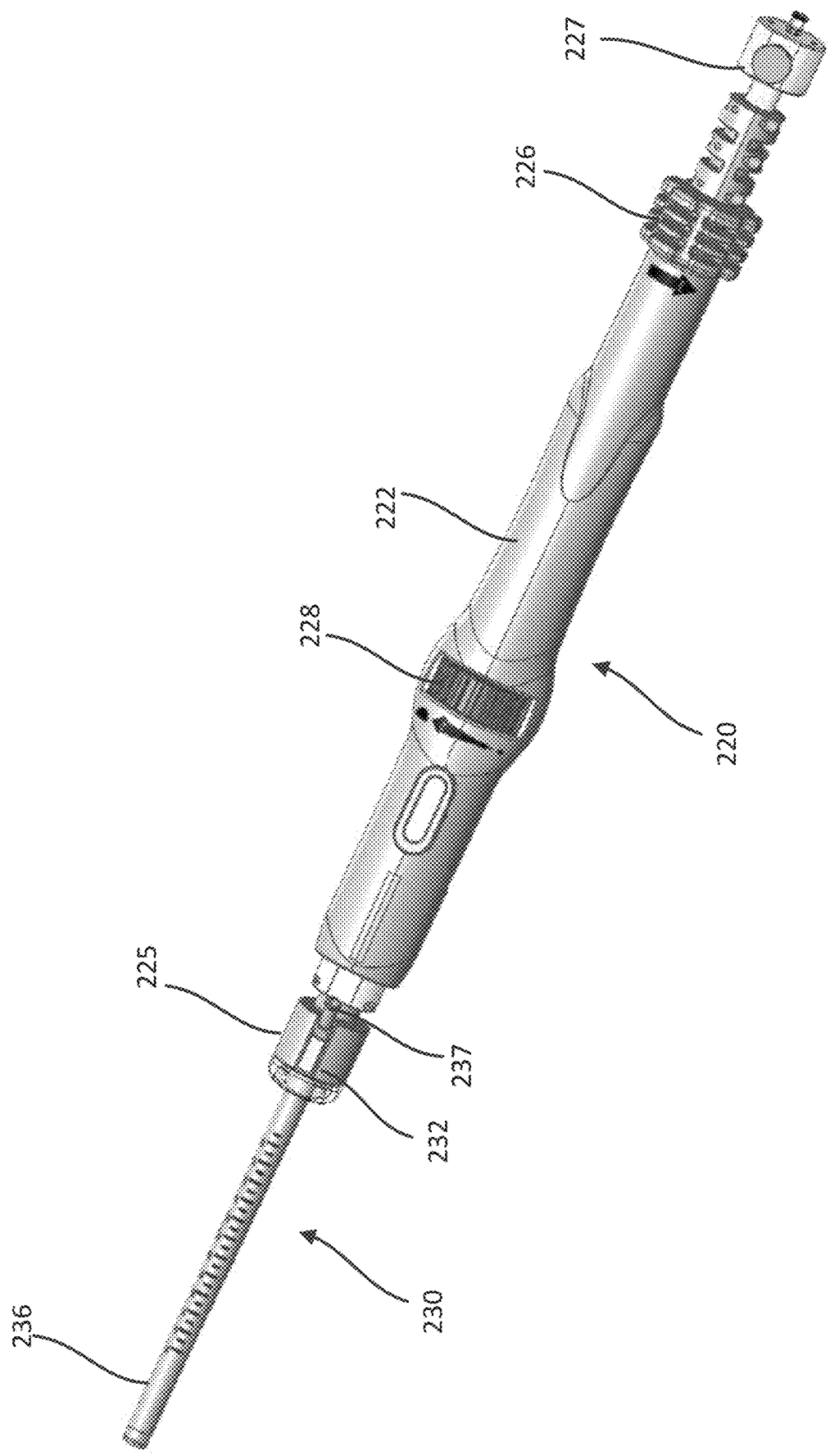
FIG. 12B is a top view of the delivery device of FIG. 4 shown with the delivery sheath in a second fully actuated position.

FIG. 4 illustrates the assembled delivery device 200 in a ready to use position (e.g., the valve holding tube 225 is coupled to the housing 222 and catheter assembly 230 with a prosthetic valve loaded therein). The proximal actuator knob 226 can then be actuated (e.g., rotated) to move the delivery rod 224 distally (in the direction of Arrow A in FIGS. 4 and 11) and push the prosthetic valve out of the valve holding tube 225 and into a distal end portion of the delivery sheath 236, as described above. FIG. 11 illustrates the delivery handle 220 without the catheter assembly 230 and valve holding tube 225 for illustrative purposes to show the delivery rod 224 actuated distally to push the prosthetic valve out of the valve holding tube 225. As the delivery rod 224 moves distally, the valve holding tube 225 remains stationary or fixed relative to the housing 222, allowing the delivery rod 224 to push the prosthetic valve out of the valve holding tube 225 and into the delivery sheath 236 until the valve holding tube 225 is disposed at a distal end portion of the delivery sheath 236. The tether can be secured to the retention mechanism 227, and the distal actuator knob 228 can then be actuated to retract or move proximally the delivery sheath 236 relative to the housing 222 such that the prosthetic valve is left disposed outside of the delivery sheath 236 and within the left atrium of the heart. More specifically, as described above, the distal actuator 228 is operatively coupled to the leadscrew 229, which is coupled to the valve holding tube 225. Thus, because the valve holding tube 225 is also coupled to the delivery sheath 236, the delivery sheath 236 is also moved proximally (the direction of arrow B in FIGS. 12A and 12B) relative to the housing 222. FIG. 12A illustrates the delivery sheath 236 partially retracted (moved proximally), and the valve holding tube 225 coupled thereto is shown partially disposed within the housing 222. FIG. 12B illustrates the delivery sheath 236 fully retracted, the hub 232 partially disposed within the housing 222, and the valve holding tube 225 disposed entirely within the housing 222. After the prosthetic valve has been deployed, with the tether coupled to the retention mechanism 227, the prosthetic valve can be maneuvered and repositioned as needed and then the tether can be released from the retention mechanism 227. The tether can then be secured to an epicardial surface of the heart with, for example, an epicardial pad (e.g., EAD in FIG. 1) as described above.

Further, prior to securing the tether, as described above, if upon initial deployment of the prosthetic valve it is determined that the valve should be repositioned, the delivery device 200 can be actuated to partially recapture a proximal portion of the valve to make adjustments to its position. For example, the delivery sheath 236 can be actuated to move distally to recapture a portion of the valve, then after the valve has been repositioned, the sheath 236 can be actuated to move proximally again to release the valve. Alternatively, the delivery rod 224 can also be used to recapture a portion of the prosthetic valve. For example, the delivery rod 224 can be actuated to move distally such that a portion of the prosthetic valve is recaptured within the lumen of the delivery rod 224. The valve can then be repositioned and then the delivery rod 224 can be actuated to move proximally to release the valve.

Figure 13:
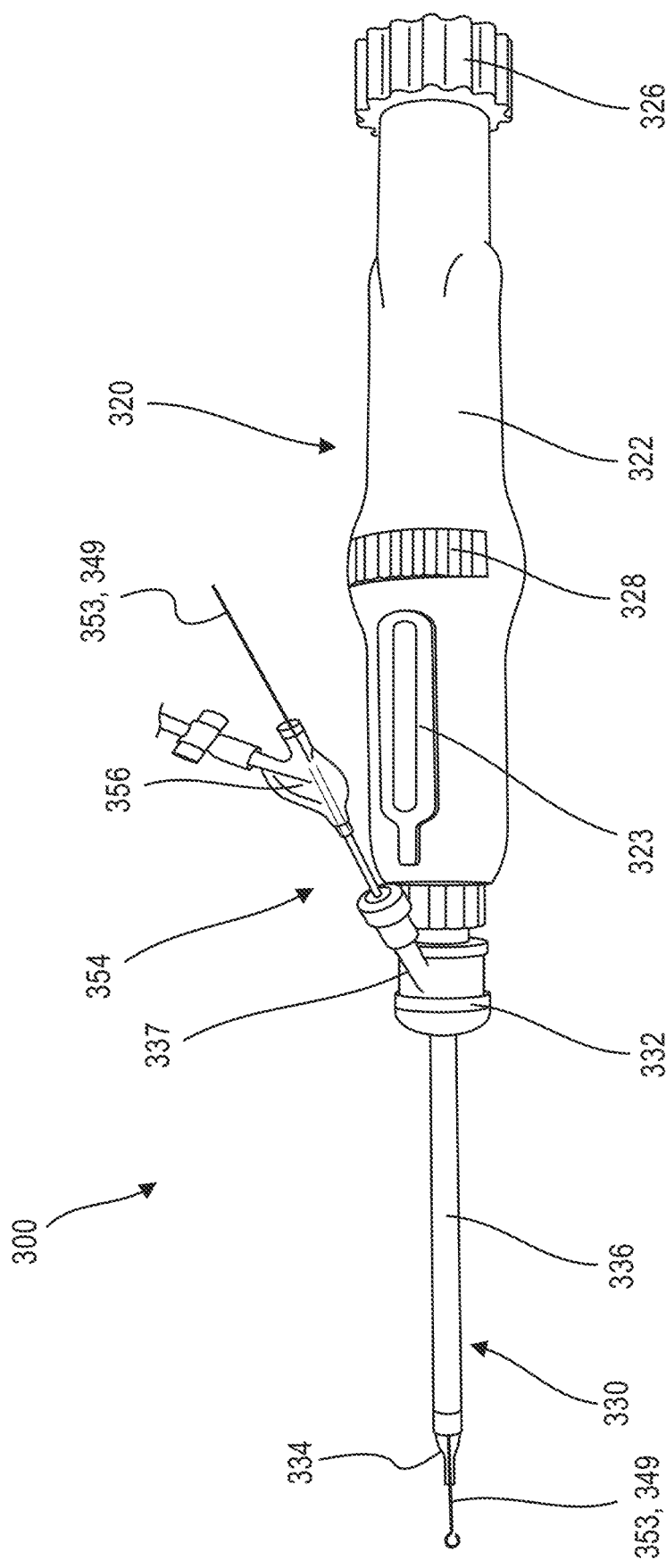
FIG. 13 is a perspective view of a delivery device, according to another embodiment.

FIG. 13 illustrates a delivery device according to another embodiment. A delivery device 300 includes a catheter assembly 330, a handle assembly 320 removably couplable to the catheter assembly 330 and a valve holding tube (not shown) removably couplable to the handle assembly 320 and the catheter assembly 330. In this embodiment, the valve holding tube is disposed within an interior of a housing 322 of the handle assembly 320 and the catheter assembly 330. The delivery device 300 can include the same or similar components and features, and can function the same as or similar to the delivery device 100 and/or the delivery device 200 described above. The delivery device 300 can be used to deliver and deploy a prosthetic heart valve within the heart, such as, for example, a prosthetic mitral valve (not shown) as described above for the previous embodiment.

The catheter assembly 330 includes a hub 332 and a delivery sheath 336. The delivery sheath 336 defines a lumen (not shown) into which a prosthetic valve disposed within the valve holding tube can be moved during delivery of the prosthetic valve as described above for previous embodiments.

The handle assembly 320 includes the housing 322, a delivery rod (not shown) coupled to the housing 322, a proximal actuator knob 326 coupled to the housing 322, and a distal actuator knob 328 coupled to the housing 322. A deployment travel window 323 is disposed on the housing 322 and can be used to view the progress of the delivery of a prosthetic heart valve visible through the deployment travel window 323. The proximal actuator knob 326 can be used to move or push distally the prosthetic heart valve (not shown) that is loaded into the handle assembly 320 via the valve holding tube (not shown). The distal actuator knob 328 can be used to actuate or move the delivery sheath 336 during deployment of the prosthetic valve into the heart. For example, the prosthetic valve can be moved distally until it is positioned within a distal end portion of the lumen of the delivery sheath 336. To deploy the prosthetic valve, the delivery sheath 336 is moved proximally disposing the prosthetic valve outside of the delivery sheath 336 and within the heart. The delivery sheath 336 can also be actuated to recapture a prosthetic heart valve that has been deployed within a heart such that the prosthetic valve can be repositioned as described above for delivery devices 100 and 200. Although not shown in FIGS. 7 and 8, the housing 322 can also include a spring tether retention and mechanical retention coupler (also referred to herein as "retention mechanism") coupled to the housing 322 as described above for previous embodiments.

As described above, the valve holding tube can contain or hold a prosthetic mitral valve in a compressed configuration within an interior lumen of the valve holding tube. The valve holding tube (with the prosthetic mitral valve therein) can be coupled to a distal end portion of the handle assembly 320 and coupled to the hub 332 of the catheter assembly 330. As described above for previous embodiments, when coupled to the handle assembly 320, a portion of the distal end portion of the delivery rod can be received within an interior region of the valve holding tube. Prior to coupling the valve holding tube to the delivery rod, a tether (not shown) coupled to the prosthetic valve (within the valve holding tube) can be threaded through a lumen defined by the delivery rod and extend proximally out of the handle assembly 320.

In this embodiment, a dilator device 354 is illustrated that can be used with the delivery device 300 during deployment of a prosthetic valve. The dilator device 354 can include a tapered distal end that can provide a lead-in for the sheath 336 and help open or enlarge the entry opening at the epicardial surface and through the mitral annulus. The dilator device 354 includes an expandable dilator balloon member 334 (also referred to herein as "balloon member"). The balloon member 334 is coupled to a balloon manifold 356 via an elongate inflation tube that extends through the delivery sheath 336 and out through a port 337 defined by the hub 332. The balloon member 334 has a tapered distal tip portion to provide a lead-in during insertion of the catheter assembly 330 into the heart. The balloon manifold 356 can be coupled to an inflation medium and used to inflate and deflate the balloon member 334. The port 337 is disposed on the hub 332 distally of the prosthetic valve. In other words, when the valve holding tube (containing the prosthetic valve) is coupled to the catheter assembly 330, the prosthetic valve is disposed proximally of where the balloon shaft exits the port 337. FIG. 13 also illustrates a shipping mandrel 353 that can be inserted through a lumen of the dilator device 354 and includes an elongate member 349. The elongate member 349 can be inserted through the balloon manifold 356, through a lumen defined by the dilator device 354, until a distal end is disposed outside a distal end of the balloon member 334. The shipping mandrel 353 can be used to maintain the alignment of the various components of the dilator device 354 and reduce or eliminate the possibility of components collapsing prior to use of the dilator device 354. The shipping mandrel 353 can be removed prior to insertion of the delivery device 300 into a patient's body.

In use to deliver and deploy a prosthetic mitral valve within a heart, with the dilator device 354, catheter assembly 330, handle assembly 320 and valve holding tube (not shown) coupled together, and with the balloon member 334 inflated, the delivery sheath 336 can be inserted through the epicardial surface of the patient's heart and extended through the left ventricle and into the left atrium of the heart such that the hub 332 is disposed on the outside of the heart near or in contact with the epicardial surface. When the delivery sheath 336 is positioned in a desired location, the balloon member 334 can be deflated and removed through the port 337.

The proximal actuator knob 326 can then be actuated (e.g., rotated) to move the delivery rod distally and push the prosthetic valve out of the valve holding tube and into a distal end portion of the delivery sheath 336 in a similar manner as described above for previous embodiments. The distal actuator knob 328 can then be actuated to retract or move proximally the delivery sheath 336 such that the prosthetic valve is left disposed outside of the delivery sheath 336 and within the left atrium of the heart.

FIGS. 14-17 illustrate a recapture device according to an embodiment. A recapture device 410 can be used to capture a prosthetic valve that is deployed within a heart such that the prosthetic valve can be repositioned and/or retrieved/removed. The recapture device 410 includes an outer sheath 444 operatively coupled to a handle assembly 420, an outer dilator 442 disposed within a lumen of the outer sheath 444, and an inner dilator 446 movably disposed within a lumen of the outer dilator 442 and operatively coupled to the handle assembly 420. The recapture device 410 also includes a tether retention mechanism 427 coupled to a proximal end portion of the handle assembly 420. The tether retention mechanism 427 can be configured the same as or similar to the retention mechanisms described herein and/or described in the '382 application incorporated herein by reference above, and can be used to secure the tether to the recapture device 410. The inner dilator 446 defines a lumen that can receive at least a portion of a prosthetic valve 440 and includes a distal tip configured to engage a prosthetic valve implanted within a heart as described in more detail below.

The handle assembly 420 includes a housing 422, a proximal actuator knob 426 coupled to the housing 422 and operatively coupled to the sheath 444, and a distal actuator knob 428 coupled to the housing 422 and operatively coupled to the dilator member 446. A deployment travel window 423 is disposed on the housing 422 and can be used to view the progress of the removal or recapture of a prosthetic heart valve. The proximal actuator knob 426 (also referred to herein as "proximal actuator" or "first actuator") can be used to move the inner dilator 446 distally and proximally within the lumen of the outer dilator 442. The distal actuator knob 428 (also referred to herein as "distal actuator" or "second actuator") can be used to actuate or move the outer sheath 444 distally and proximally.

Figure 14:
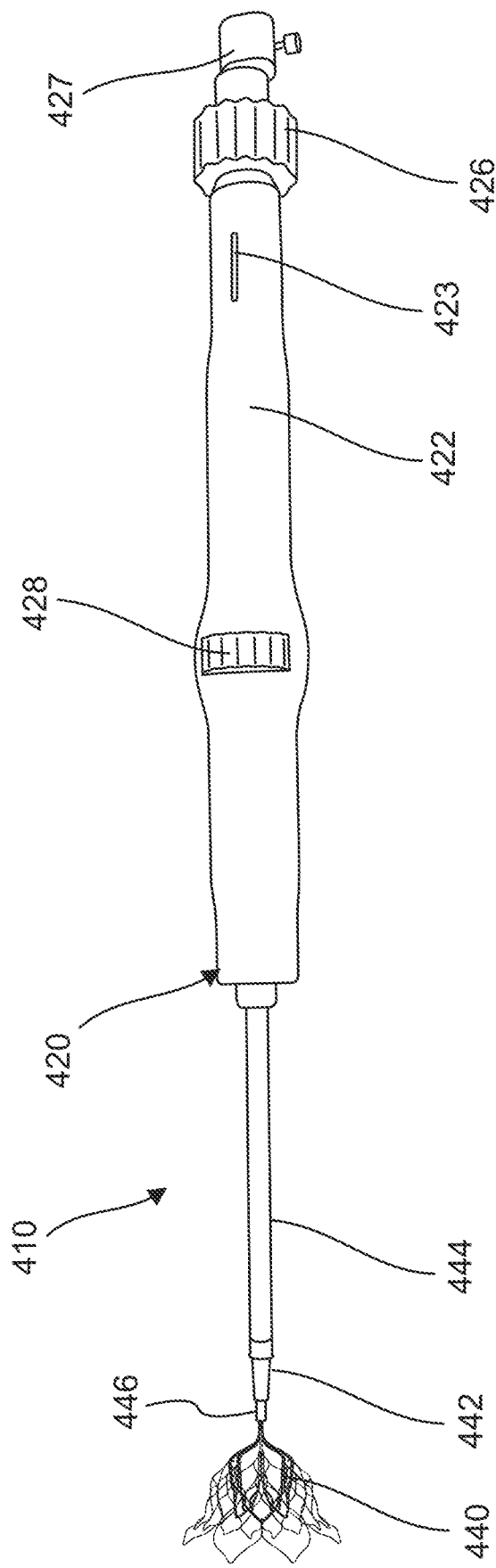
FIG. 14 is a side view of a recapture device, according to an embodiment, and shown coupled to a frame of a prosthetic valve.
Figure 15:
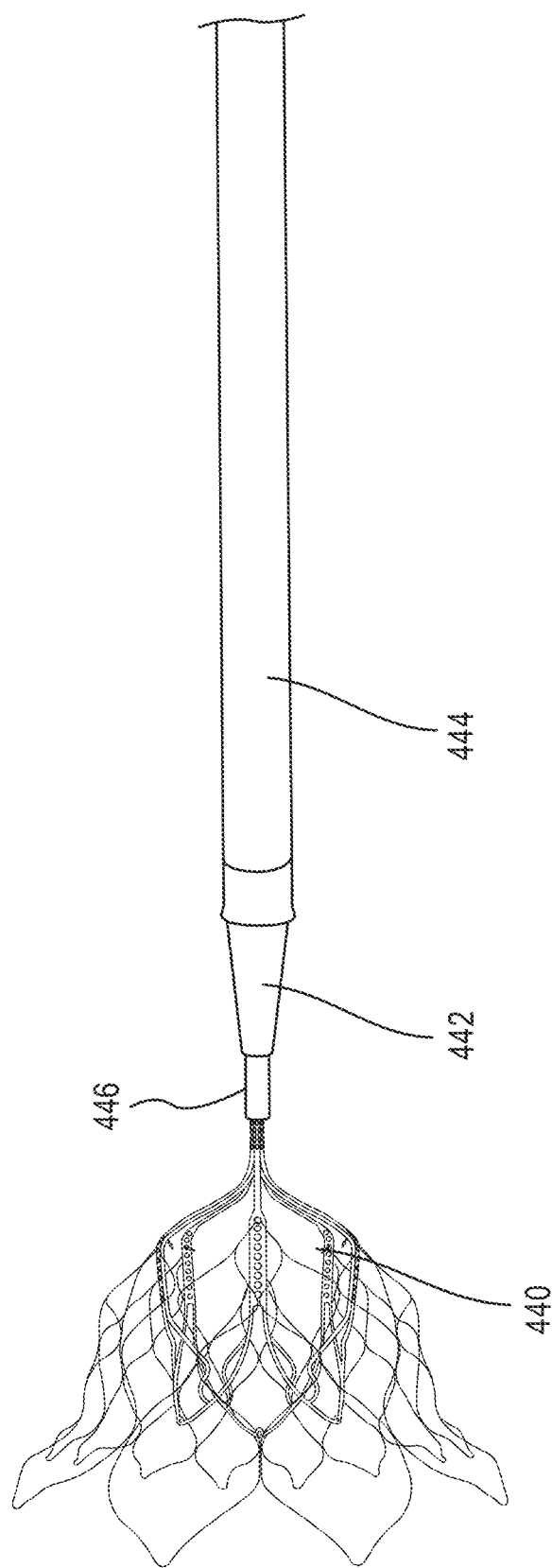
FIG. 15 is an enlarged view of a portion of the recapture device and prosthetic valve frame of FIG. 14 shown with the inner dilator member in a first position engaged with the prosthetic valve frame.
Figure 16:
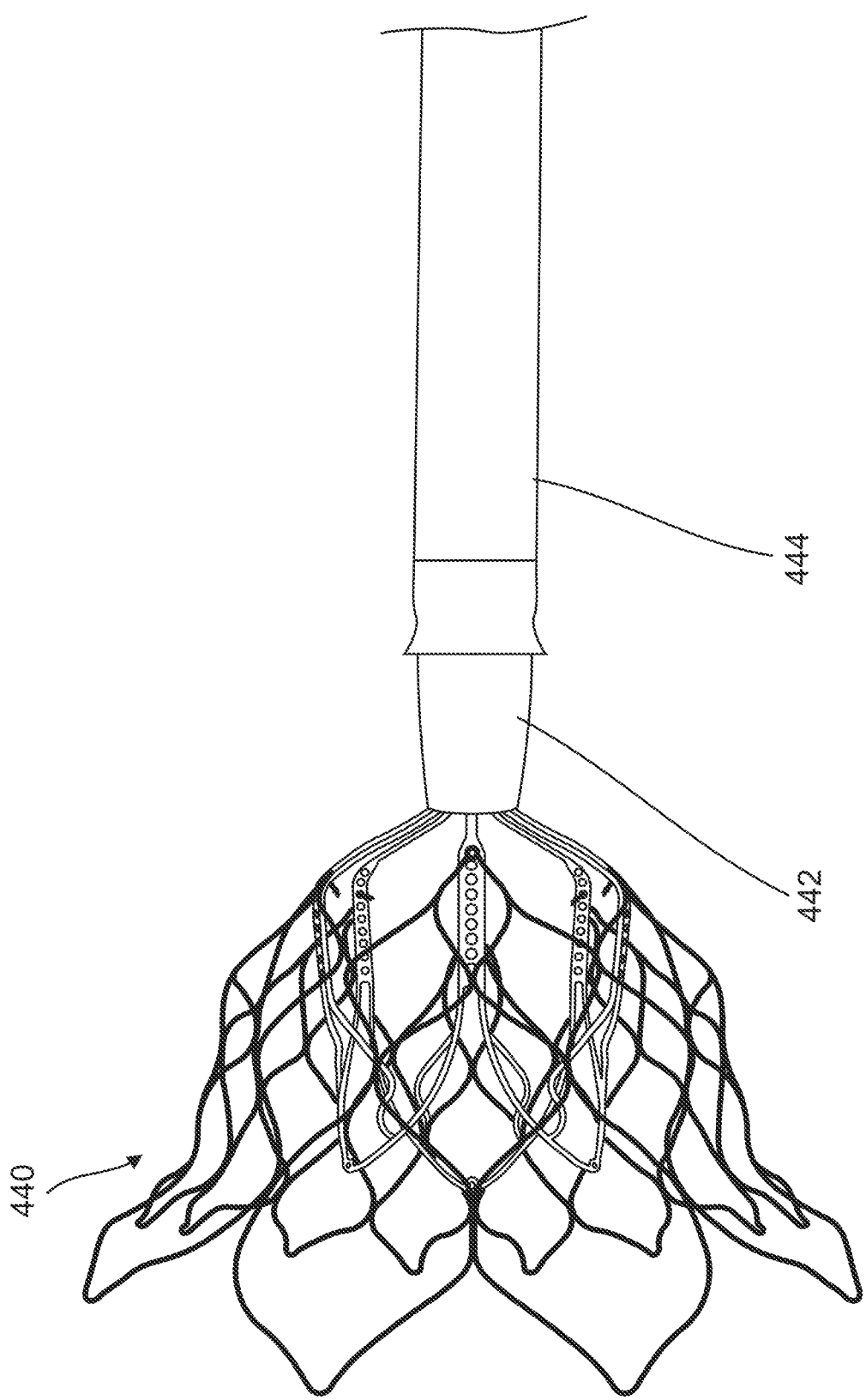
FIG. 16 is an enlarged view of a portion of the recapture device and prosthetic valve frame of FIG. 14 shown with the inner dilator (not visible) in a second position disposed within the outer dilator, and the outer sheath extended over a portion of the outer dilator and a portion of the valve captured within the outer sheath.

As shown in FIGS. 14 and 15, to capture a prosthetic valve 440 that has been deployed within a heart, the tether coupled to the prosthetic valve 440 can be threaded or inserted through the lumen of the inner dilator 446 and the distal tip of the inner dilator 446 can engage a proximal portion of the valve 440 by actuating the proximal actuator 426 to move the inner dilator 446 distally into contact with the valve 440. Thus, as the inner dilator 446 is moved distally, a portion of the valve 440 can be received and collapsed within the lumen of the inner dilator 446, as shown in FIGS. 14 and 15. As shown in FIG. 16, the inner dilator 446 can be actuated (e.g., turning or rotating the proximal actuator knob 426) to move the inner dilator 446 proximally such that the distal tip of the dilator member 442 and a first portion of the valve 440 are pulled into the lumen of the outer dilator 442. For example, with the portion of the valve 440 collapsed within the lumen of the inner dilator, the valve 440 will move distally with the inner dilator 446. With the valve 440 captured as shown in FIG. 16, the tether can be secured to the retention mechanism 427, and the valve 440 can be moved/repositioned within the heart.

Figure 17:
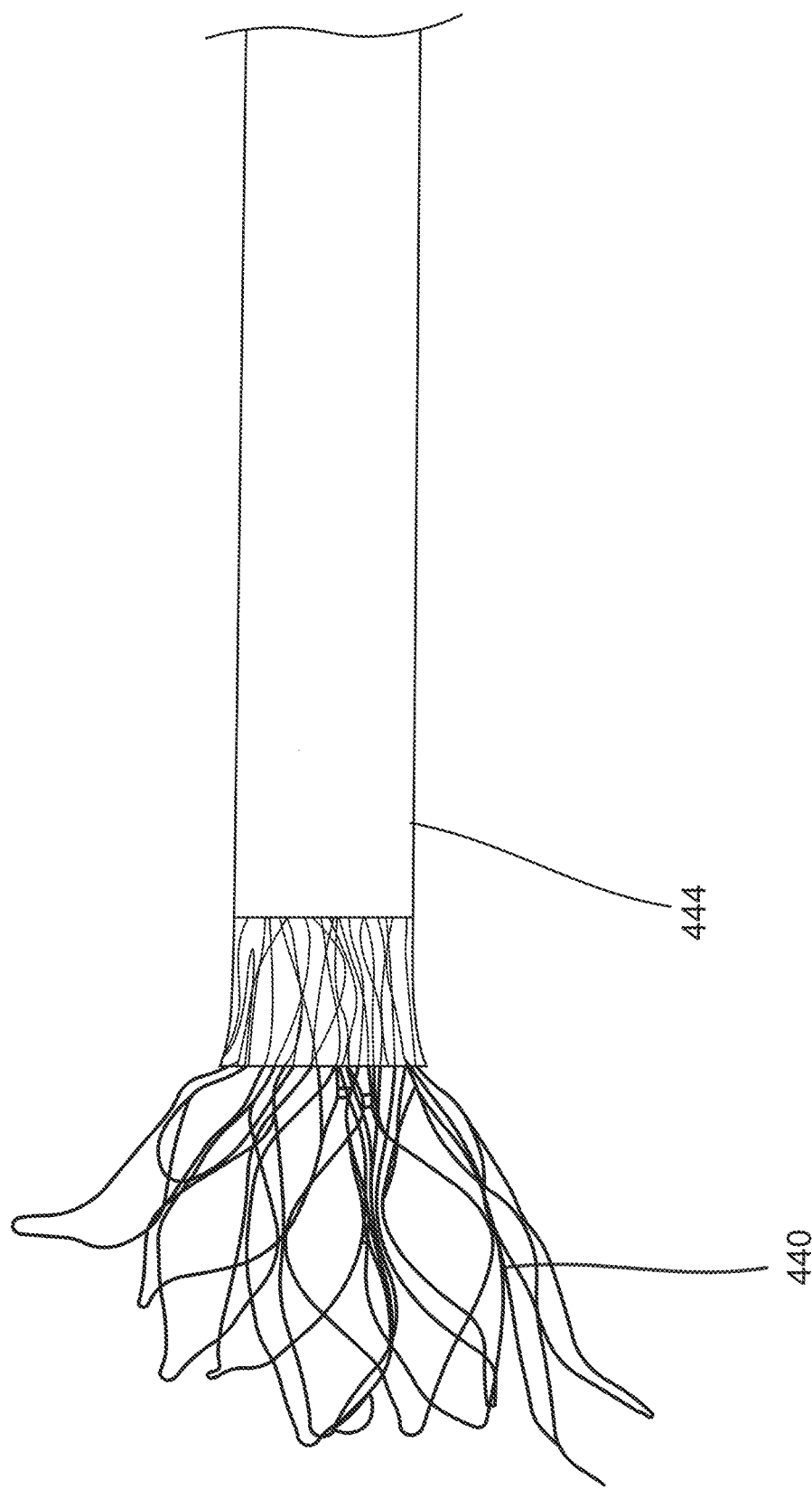
FIG. 17 is an enlarged view of a portion of the recapture device and prosthetic valve frame of FIG. 14 shown with the outer dilator (not visible) disposed within the outer sheath and a portion of the valve frame captured within the outer sheath.
Figure 18:
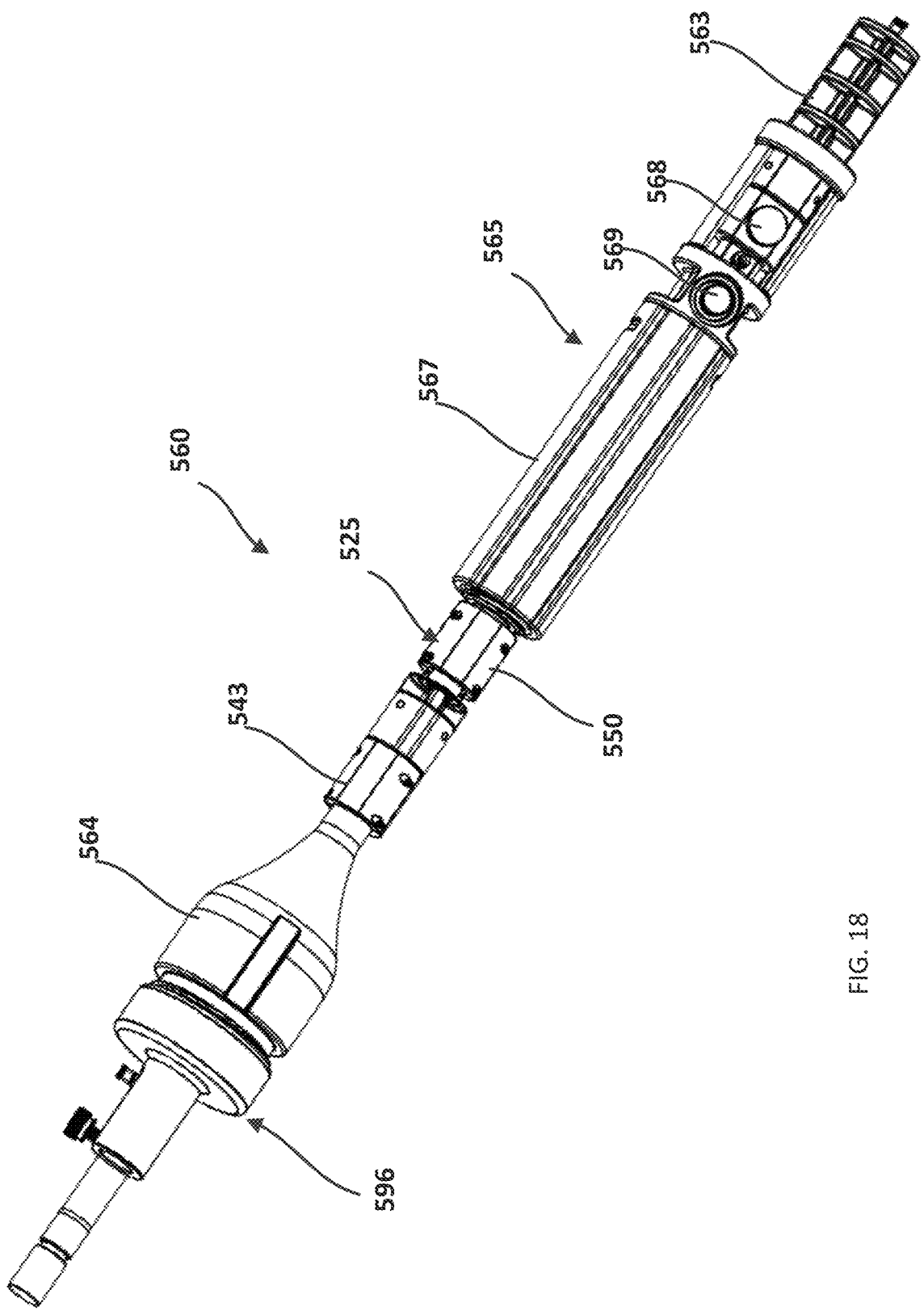
FIG. 18 is a perspective view of a valve loading device, according to an embodiment.
Figure 19:
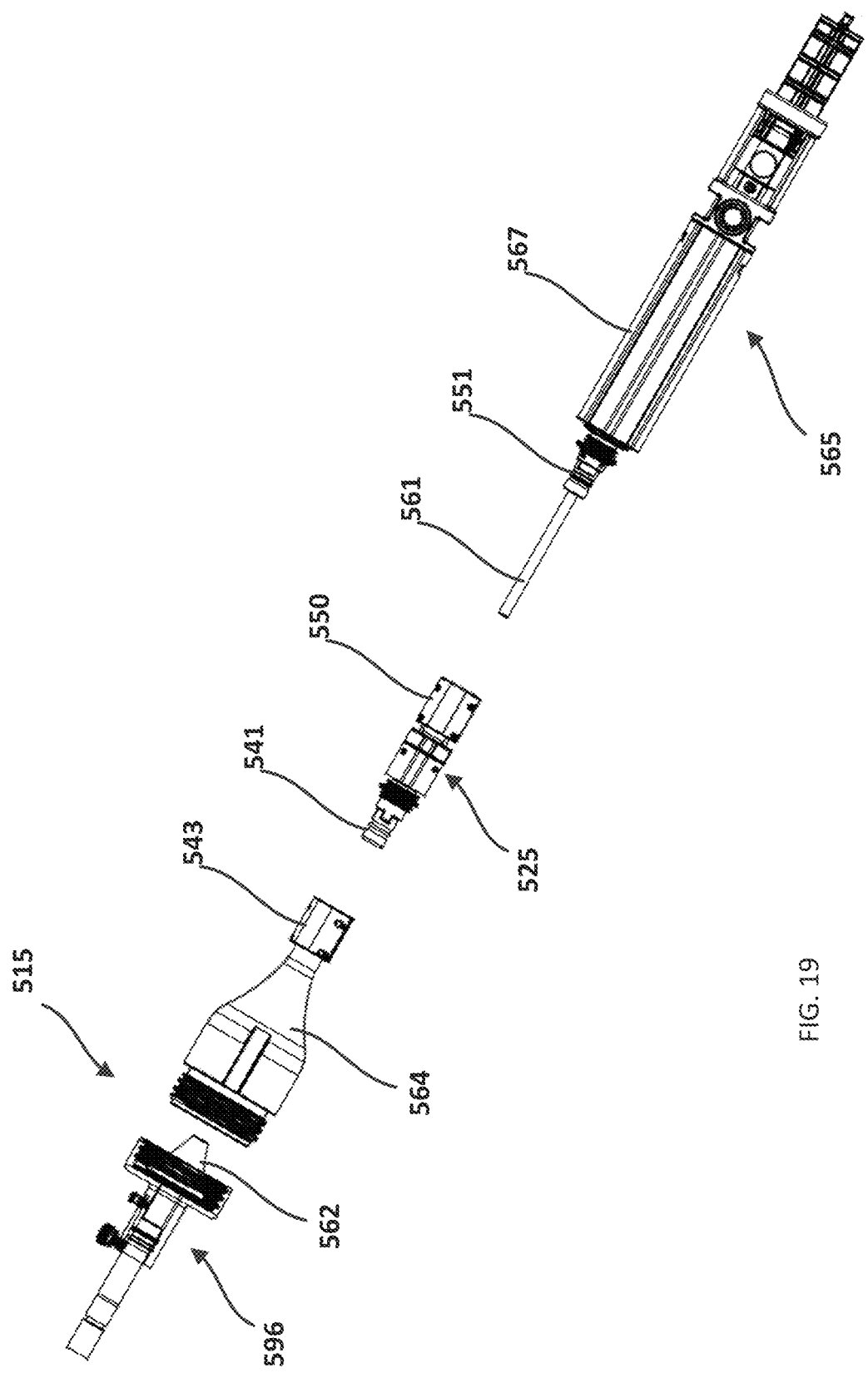
FIG. 19 is an exploded view of the valve loading device of FIG. 18.
Figure 20A:
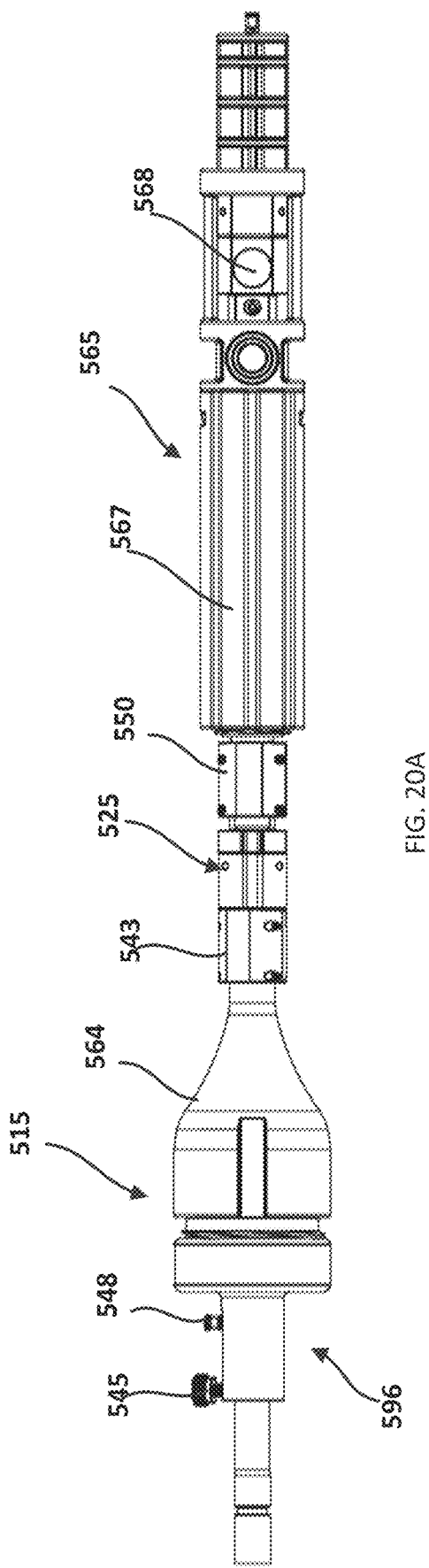
FIG. 20A is a top view of the valve loading device of FIG. 18.
Figure 20B:
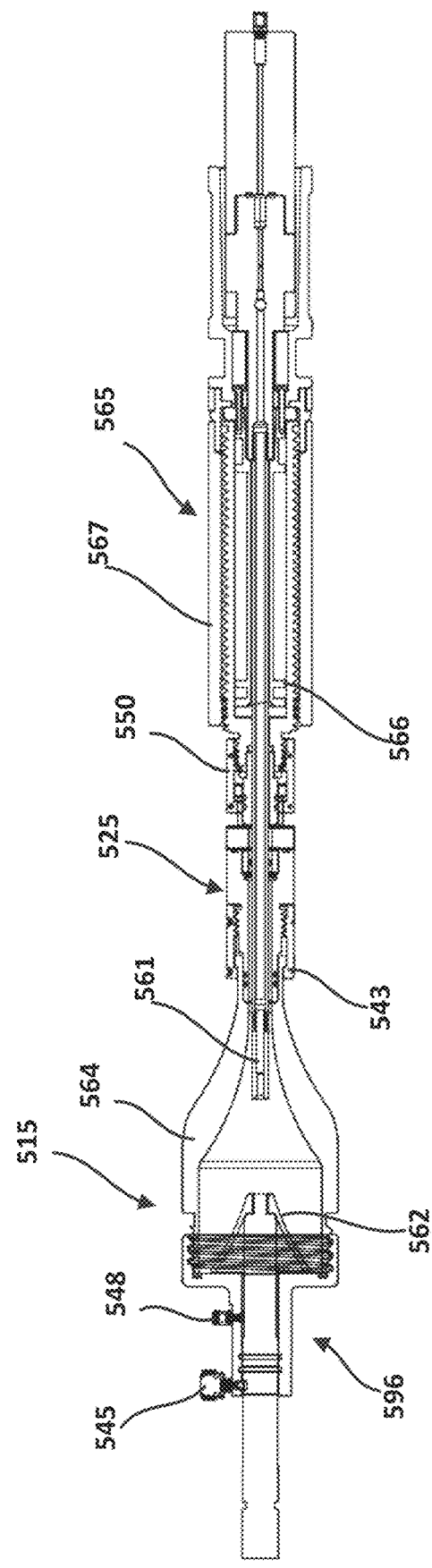
FIG. 20B is a cross-sectional view of the valve loading device of FIG. 20A.

To fully remove/retrieve the valve 440, the sheath 444 can be moved distally as shown in FIG. 17, to further capture the valve 440 within the lumen of the sheath 444 until the valve 440 is fully captured within the lumen of the outer sheath 444. For example, the distal actuator knob 428 can be actuated (e.g., rotated or turned) to move the outer sheath 444 distally relative to the inner dilator 446 and to the outer dilator 442. The outer sheath 444 also moves relative to the handle assembly 422. Thus, with the tether secured to the handle assembly 422 via the retention mechanism 427, the outer sheath 444 moves distally relative to the valve 440 to capture the valve 440 within the lumen of the outer sheath 444. With the valve 440 captured within the lumen of the sheath 444, the valve 440 can be removed from the heart by removing the recapture device 410 from the heart and the patient's body.

The two-stage actuation of the recapture device 410 allows for a controlled capture of a prosthetic valve implanted within a heart to reposition and/or remove/retrieve the prosthetic valve. The proximal portion of the frame of the valve 440 can first be collapsed sufficiently for a portion of the frame to be disposed within the lumen of the outer dilator 442, and then can transition into a more fully collapsed configuration as it is moved into the lumen of the outer sheath 444. Further embodiments of a recapture device are described below with reference to FIGS. 44-53.

FIGS. 18-25 illustrate a valve loading device 560 according to an embodiment. The valve loading device 560 can be used to load a prosthetic valve (not shown) into a valve holding tube 525 which can be similar to or the same as the valve holding tubes described herein (e.g., 125, 225). The valve loading device 560 can be used to compress the prosthetic valve to a desired size and shape prior to loading the valve into the valve holding tube. Another embodiment of a valve loading device is described in the '382 application incorporated herein by reference above. The valve loading device 560 includes a handle assembly 565 and a funnel assembly 515 that includes a top cap assembly 596 and an outer funnel 564. The top cap assembly 596 includes an inner funnel or centering cone 562. As best shown in FIGS. 20B and 21B, the handle assembly 565 includes a centering rod 561 operatively coupled to a centering rod locator 563, a loading leadscrew 566 and a main loading knob or handle 567. A tether piercing member 568 can be used to secure a tether extending from the prosthetic valve within the valve loading device 560. The loading leadscrew 566 can be actuated to move the valve holding tube 525 and capture the prosthetic valve as described in more detail below.

The valve holding tube 525 can be removably coupled to the handle assembly 565 via a quick connect coupler 550 (a female connector in this embodiment) that can matingly couple to a quick connect coupler 551 (a male connector in this embodiment) on the loading leadscrew 566 of the handle assembly 565. The valve holding tube 525 can also be coupled to the outer funnel 564 via a quick connect coupler 541 (a male connector in this embodiment) that can matingly couple to a quick connect coupler 543 (a female connector in this embodiment) on the outer funnel 564. The quick connect couplers 550, 551, 541 and 543 can be, for example, bayonet connectors or ¼ turn connectors. The quick connect couplers can also include O-rings to maintain the position of the valve holding tube 525 to the handle assembly 565 and to the outer funnel 564. The centering rod 561 can be used to center the prosthetic valve and hold the valve in position when the valve is loaded within the outer funnel 564. A centering rod securement knob 569 secures the centering rod 561 in position. The centering rod securement knob 569 can be, for example, a thumb screw or set screw.

In some embodiments, prior to loading the prosthetic valve into the valve loading device 560, the handle assembly 565 can be placed within a fixture such that the handle assembly 565 is positioned in a vertical orientation with the quick connect coupler 551 at the top. The valve holding tube 525 can be coupled to the handle assembly 565 as described above by coupling the quick connect coupler 550 of the valve holding tube 525 to the quick connect coupler 551 of the handle assembly 565. The outer funnel 564 can be coupled to the valve holding tube 525 by coupling the quick connect coupler 543 of the outer funnel 564 to the quick connect coupler 541 of the valve holding tube 525. Thus, the handle assembly 565, valve holding tube 525 and outer funnel 564 will be coupled together in a vertical orientation within the fixture. The prosthetic heart valve can be placed within the interior region defined by the outer funnel 564 of the funnel assembly 515. The tether of the valve is threaded through the outer funnel 564, through the valve holding tube 525, and through the centering rod 561 of the handle assembly 565. The tether piercing member 568 can be turned to pierce the tether and secure the tether to the loading device 560. In some embodiments, with an asymmetric prosthetic mitral valve, the valve is loaded into the loading device 560 so that the A2 section of the valve (see PCT application '58826) is loaded upwards. This can ensure that the A2 segment of the valve is compressed in the same way it is delivered to the A2 region of the anterior native leaflet to reduce or prevent LVOT obstruction. The inner funnel or centering cone 562 can then be threadably attached to the outer funnel 564 with mating threaded portions 597 and 598, respectively (see, e.g., FIGS. 22A and 22B) and secured to the outer funnel 564 with a quick connector 545 (e.g., a thumb screw or set screw) that locks the inner funnel/centering cone 562 to the outer funnel 564 as shown, for example, in FIG. 20B.

A syringe can be coupled to a port 548 of the top cap assembly 596 to provide a saline flush to remove all trapped air bubbles within the loading device 560. The valve can also be checked for air, shaken, tapped to remove trapped air, etc. while within the loading device 560. If any bubbles are seen, they can be removed by flushing a saline through the loading device 560 (e.g., with a syringe coupled to the port 548), especially out of any top pockets of the valve. In some cases, the process of loading the prosthetic valve into the valve loading device 560 can be performed with the valve and loading device 560 submerged in a saline/water bath with care being taken to remove all trapped air bubbles within the loading device 560.

In an alternative procedure, the valve can be placed in the outer funnel 564 prior to the outer funnel being coupled to the valve holding tube 525. The outer funnel 564 and centering cone 562 can be coupled together as described above, and the outer funnel 564 can be coupled to the valve holding tube 525 via the quick connect couplers 541 and 543. In some cases, the valve holding tube 525 can be coupled to the handle assembly 565 via the quick connect couplers 550 and 551 prior to the funnel assembly 515 (outer funnel and top cap assembly 596) being coupled to the valve holding tube 525. In other cases, the valve holding tube 525 can be coupled to the handle assembly 565 prior to the funnel assembly 515 being coupled thereto.

Figure 23:
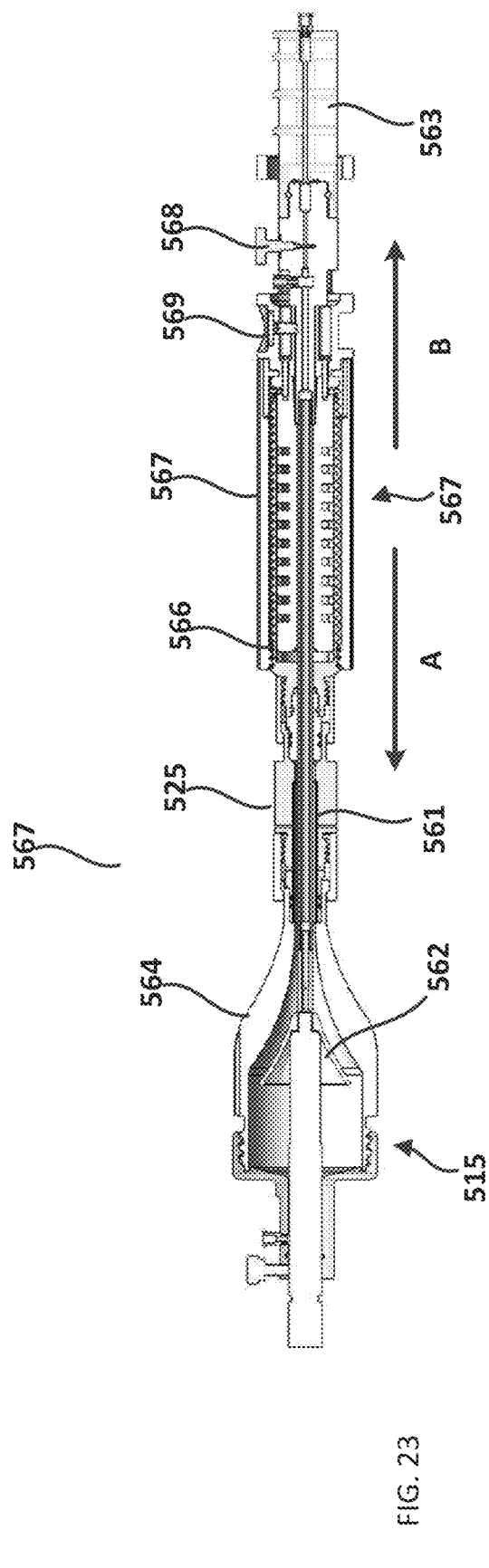
FIG. 23 is a cross-sectional view of the valve loading device of FIG. 18, shown in a first position prior to actuation of the loading device.
Figure 24:
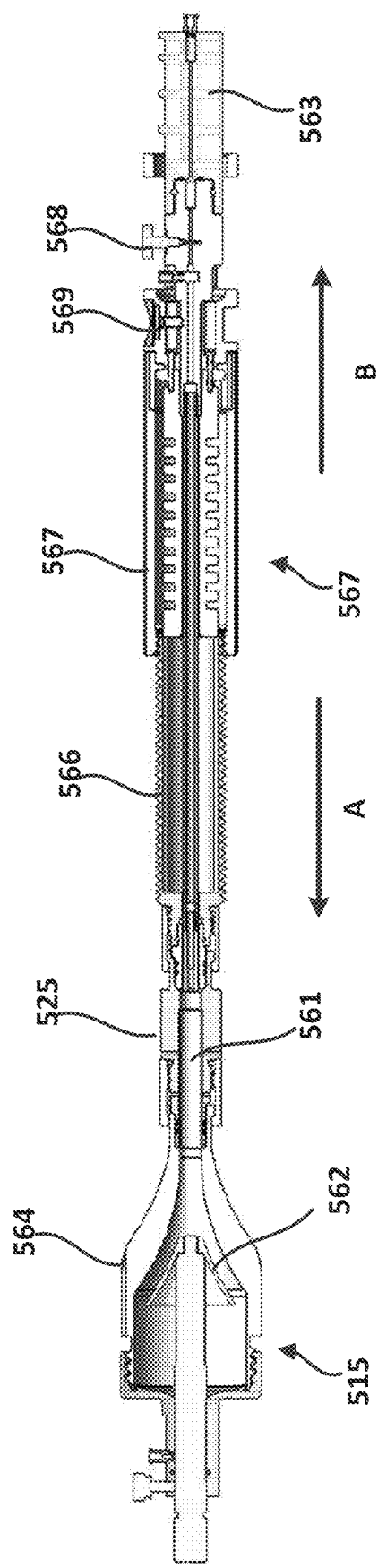
FIG. 24 is a cross-sectional view of the valve loading device of FIG. 18, shown in a second position after actuation of the loading device with the leadscrew extended from the handle assembly.

With the funnel assembly 515 (with prosthetic valve loaded therein) coupled to the valve holding tube 525 and handle assembly 565, the entire assembly can be removed from the fixture, flipped upside down, and placed back in the fixture in a vertical orientation, now with the distal end of the handle assembly 565 at the top and the funnel assembly 515 at the bottom. A saline flush can continue to be used (e.g., introduced through port 548) during the procedure to move the valve from the funnel assembly 515 to the valve holding tube 525. To move the prosthetic valve from the funnel assembly 515 (i.e., outer funnel 564/centering cone 562) into an interior region of the valve holding tube 525, the main loading knob or handle 567 is actuated (e.g., rotated) which in turn moves the loading leadscrew 566 in the direction of arrow A relative to the handle 567, as shown in FIG. 23. As the loading leadscrew 566 is moved in the direction of arrow A, because the valve holding 525 is coupled to the loading leadscrew 566 via the quick connect couplers 550, 551 and to the funnel assembly 515 via the quick connect couplers 541, 543, the valve holding tube 525 and the funnel assembly 515 also move with the loading leadscrew 566 in the direction of arrow A, as shown in FIG. 24. FIG. 23 illustrates the valve holding tube 525 and funnel assembly 515 and loading leadscrew 566 prior to being moved proximally, and FIG. 24 illustrates the valve holding tube 525 and funnel assembly 515 and loading leadscrew 566 after being moved proximally in the direction of arrow A, relative to the handle assembly 565.

The prosthetic valve (not shown) (disposed within the funnel assembly 515) remains in a fixed position relative to the handle 567 due to the tether (attached to the valve) being secured to the handle assembly 565 (and handle 567) via the tether piercing member 568. Similarly, the centering rod 561 remains in a fixed position due to being held by the centering rod securement knob 569, which remains fixed axially relative to the handle 567. Thus, as the valve holding tube 525 and the funnel assembly 515 move in the direction of arrow A, the prosthetic valve (and centering rod 561) do not move, and the funnel assembly 515 and the valve holding tube 525 move over the prosthetic valve until the prosthetic valve is captured within an interior region of the valve holding tube 525. With the prosthetic valve within the valve holding tube 525, the valve holding tube 525 can be disconnected from the outer funnel 564 and the handle assembly 565. The valve holding tube 525 can then be coupled to a valve delivery device (e.g., 100, 200) as described herein to be delivered to a heart.

Although the above method of moving a prosthetic valve from being disposed within the funnel assembly 515 to being disposed within the valve holding tube 525 included moving the loading leadscrew 566 in the direction of arrow A to then move the funnel assembly 515 and valve holding tube 525 in the direction of arrow A, in an alternative method, the loading leadscrew 566 can be actuated to move in the opposite direction (i.e., in the direction of arrow B in FIGS. 23 and 24). In such a method, because the tether is coupled/secured to the tether retention mechanism 568, and the retention mechanism is in a fixed relation to the actuator/handle 567, if the actuator/handle 567 is moved in the direction of arrow B, the tether will be moved in the same direction along with the actuator/handle 567. Thus, the tether (coupled to the valve) can pull the prosthetic valve out of the funnel assembly 515 and within the valve holding tube 525.

Figure 25:
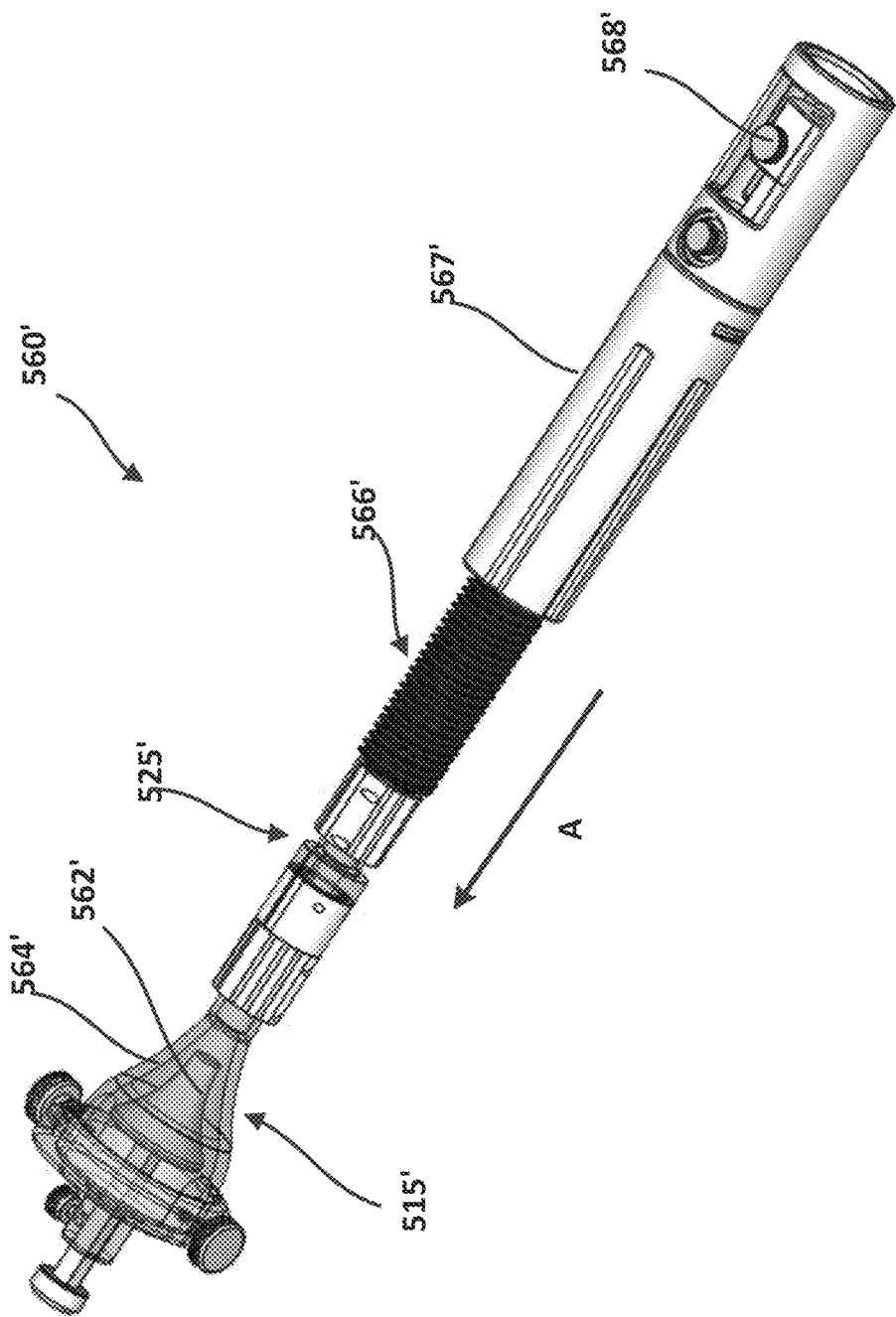
FIG. 25 is a perspective view of a valve loading device, according to another embodiment, shown with the loading leadscrew in an actuated position.

FIG. 25 illustrates an alternative embodiment of a valve loading device 560' which can include the same or similar features and can function the same as or similar to the valve loading device 560. For example, the valve loading device 565' includes a funnel assembly 515' having an outer funnel 564' and an inner funnel 562, a valve holding tube 525' and a handle assembly 565' with a loading leadscrew 566'. FIG. 25 illustrates the valve loading device after being actuated to move the valve holding tube 525' and funnel assembly 515' in the direction of arrow A. More details regarding the valve loading device 560' are described in provisional application Nos. 62/148,579 and 62/312,136, incorporated by reference above.

Figure 26:
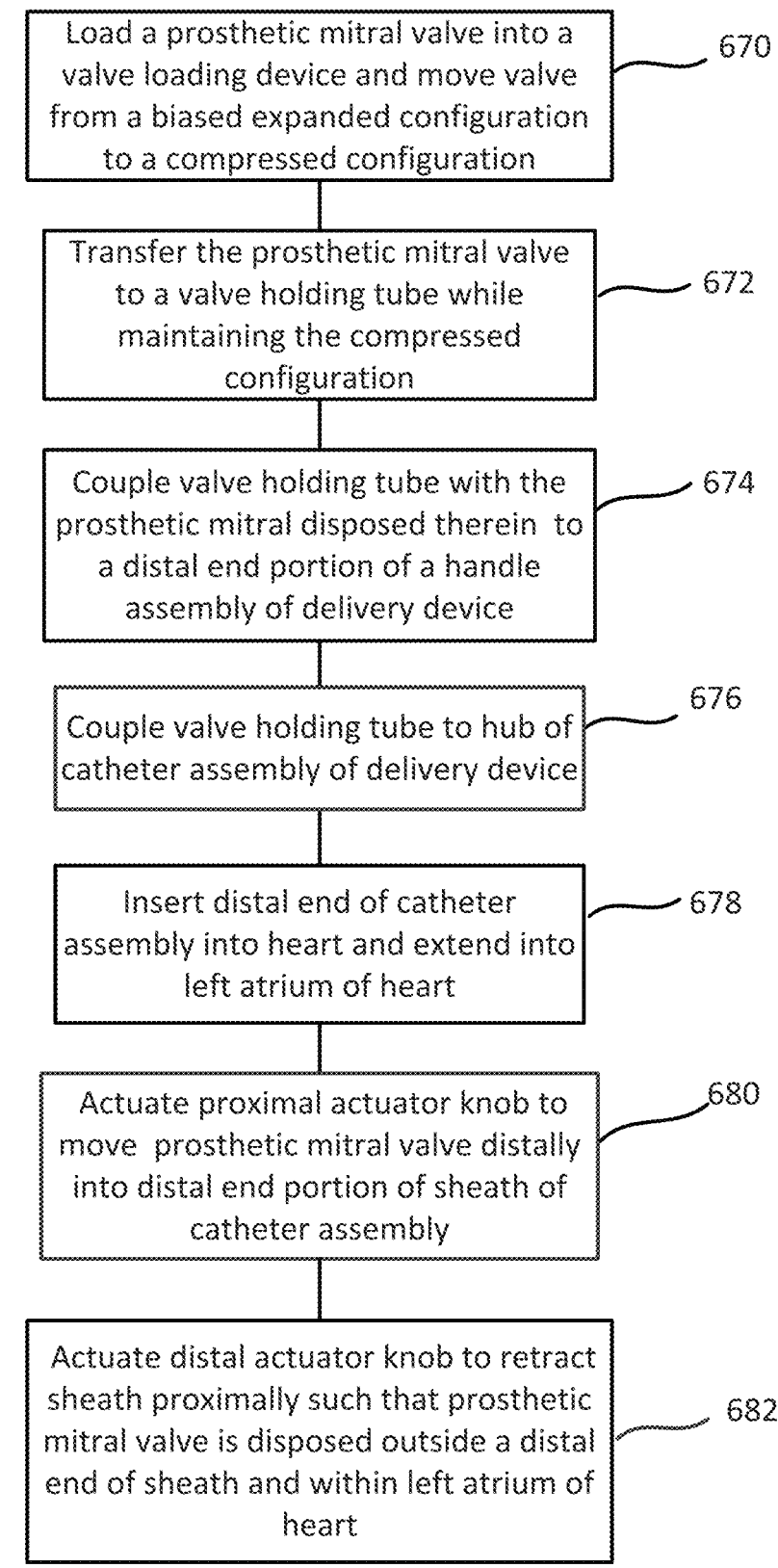
FIG. 26 is a flowchart illustrating a method of delivering a prosthetic heart valve according to an embodiment.

FIG. 26 is a flowchart illustrating a method of deploying a prosthetic mitral valve into a heart, according to an embodiment. At 670, a prosthetic mitral valve is loaded into a valve loading device (e.g., 160, 560) and moved from a biased expanded configuration to a compressed configuration within the valve loading device. At 672, the prosthetic mitral valve is transferred to a valve holding tube (e.g., 125, 225, 525) while maintaining the compressed configuration. At 674, the valve holding tube with the prosthetic mitral valve disposed therein in a compressed configuration is coupled to a distal end portion of a handle assembly of a valve delivery device (e.g., 100, 200). Prior to coupling the valve holding tube to the distal end of the handle assembly, a tether coupled to the prosthetic mitral valve can be threaded through a lumen of the handle assembly and through a lumen of a tether retention mechanism (e.g., 127, 227) of the handle assembly. At 676, the valve holding tube can be coupled to a hub of a catheter assembly (e.g., 130, 230) of the valve delivery device. Thus, the proximal end of the valve holding tube is coupled to the handle assembly and the distal end of the valve holding tube is coupled to the catheter assembly. At 678, the distal end of the catheter assembly is inserted into a heart and extended to the left atrium of the heart. For example, with the valve holding tube coupled to the catheter assembly and to the handle assembly, the distal end of the sheath of the catheter assembly can be inserted into the heart. At 680, a proximal actuator knob is actuated such that the prosthetic mitral valve is moved distally out of the valve holding tube and into a distal end portion of the delivery sheath. At 682, a distal actuator knob is actuated to move the delivery sheath proximally such that the prosthetic mitral valve is disposed outside a distal end of the delivery sheath and within the left atrium of the heart. The prosthetic mitral valve is moved to a biased expanded configuration within the heart when uncompressed within the holding tube and delivery sheath.

Figure 27:
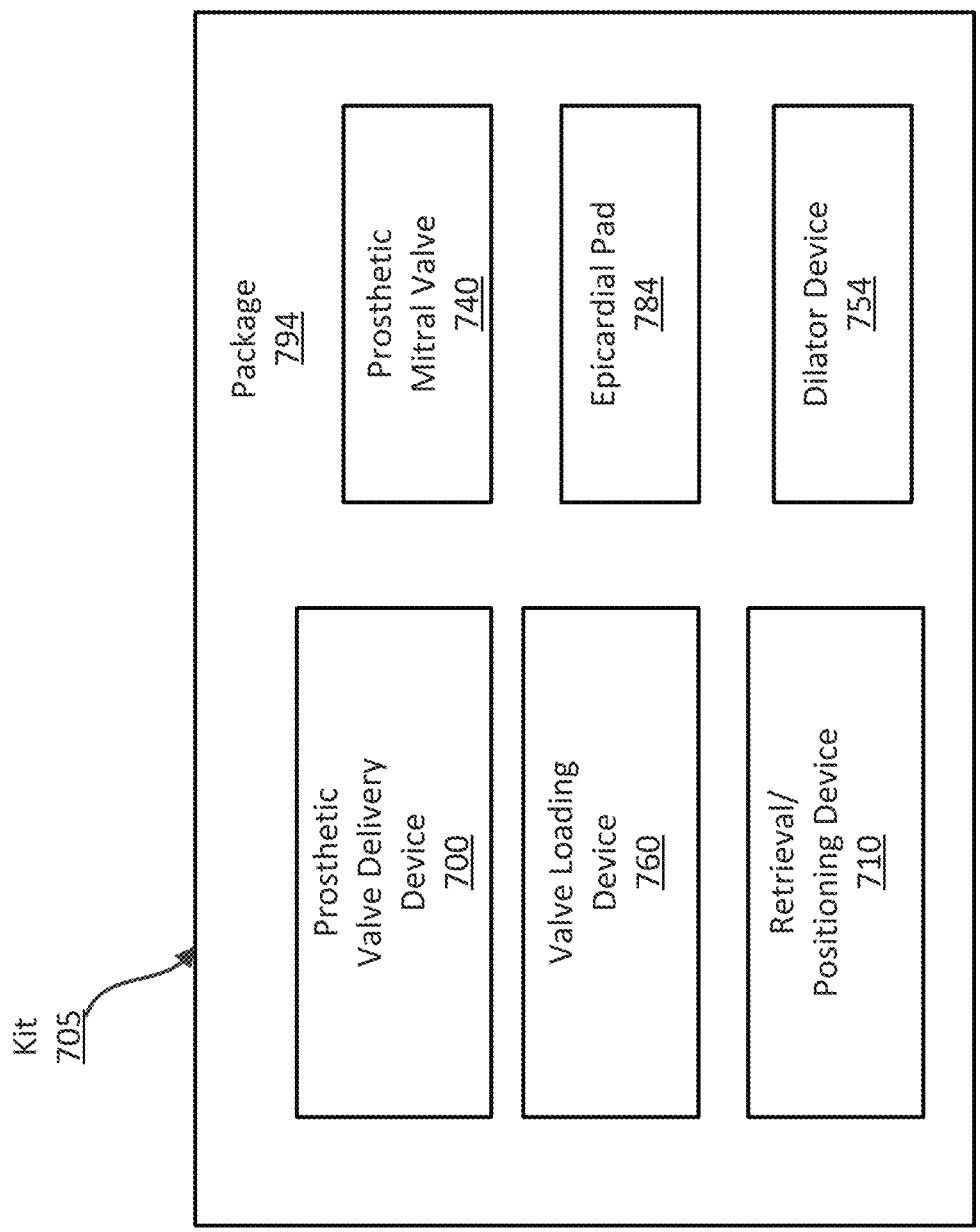
FIG. 27 is a schematic illustration of a kit according to an embodiment.

FIG. 27 is a schematic illustration of a kit according to an embodiment. In some embodiments, a surgical kit 705 can include a delivery device 700 which can be, for example, a delivery device as described herein (e.g., delivery device 100, 200, 300) and a valve loading device 760 (e.g., valve loading device 160, 560). A kit 705 can also optionally include a recapture device 710 (e.g., 410, 1010, 1110, 1210, 1310). A kit 705 can optionally include one or more of a transcatheter prosthetic valve 740 (e.g., a prosthetic mitral valve) and/or an epicardial pad 784 to secure the transcatheter valve 740 in position within the heart and/or a dilator device 754 (e.g., dilator device 354, 854, 954) as described herein and/or a guidewire (not shown in FIG. 23). A kit 705 can also include a sterile package 794 in which the components of the kit can be sealed for transport.

FIGS. 28-42 illustrate another embodiment of a dilator device that can be used with a delivery device (not shown with respect to FIGS. 28-42), such as, for example, the delivery devices 100, 200, 300 described above. A dilator device 854 can be inserted through a port of a catheter assembly, such as the port 237 of catheter 230 or the port 337 of catheter assembly 330 described above. A hemostasis valve (not shown) can be coupled to the side port such that the dilator device 854 is passed through the hemostasis valve when inserted through the side port 227, 337.

Figure 28:
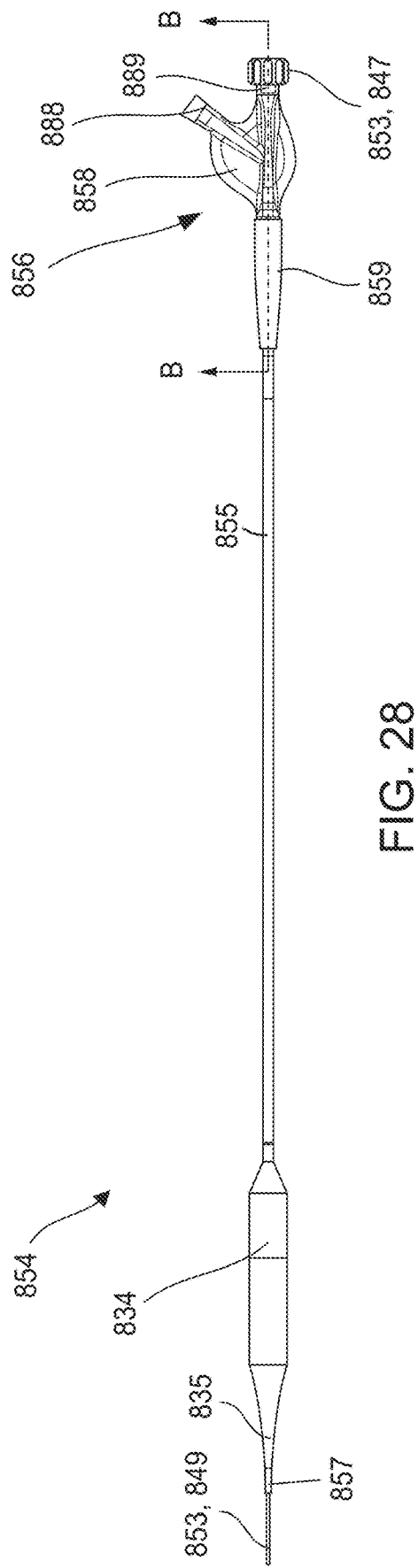
FIG. 28 is a side view of a dilator device according to an embodiment.

As shown in the side view of FIG. 28, the dilator device 854 includes an expandable dilator balloon member 834 (also referred to herein as "balloon member") that has a tapered distal end that can provide a lead-in for a delivery sheath (not shown) (such as the delivery sheath 336 described above), and used to help open or enlarge the entry opening at the epicardial surface of the heart and through the wall of the ventricle, e.g. at the apex. The balloon member 834 is shown in FIGS. 28, 30, and 34-42 in a partially inflated or almost fully inflated configuration.

The balloon member 834 is coupled to a balloon manifold 856 via an elongate inflation tube 855. The balloon manifold 856 can be the same as or similar to the balloon manifold 356 described above and includes an inflation port 888 and a guidewire port 889. The inflation port 888 can be coupled to a source of an inflation medium used to inflate and deflate the balloon member 834. The elongate inflation tube 855 (also referred to herein as "inflation tube") is coupled to the balloon manifold 856 and to the balloon member 834 as described in more detail below. The inflation tube 855 defines an inflation lumen in fluid communication with an interior region of the balloon member 834 such that the inflation medium can travel through the inflation port 888, through the inflation lumen, and into the balloon member 834. The dilator device 854 also includes an elongate guidewire tube 857 (also referred to herein as "guidewire tube") that is coupled to a distal neck portion 839 of the balloon member 834 (described in more detail below) and extends through the balloon member 834, the inflation lumen of the inflation tube 855 and out a proximal end of the inflation tube 855. The guidewire tube 857 defines a guidewire lumen through which a guidewire (not shown) can be inserted. The guidewire can be, for example, 0.035 inches in diameter.

Figure 29:
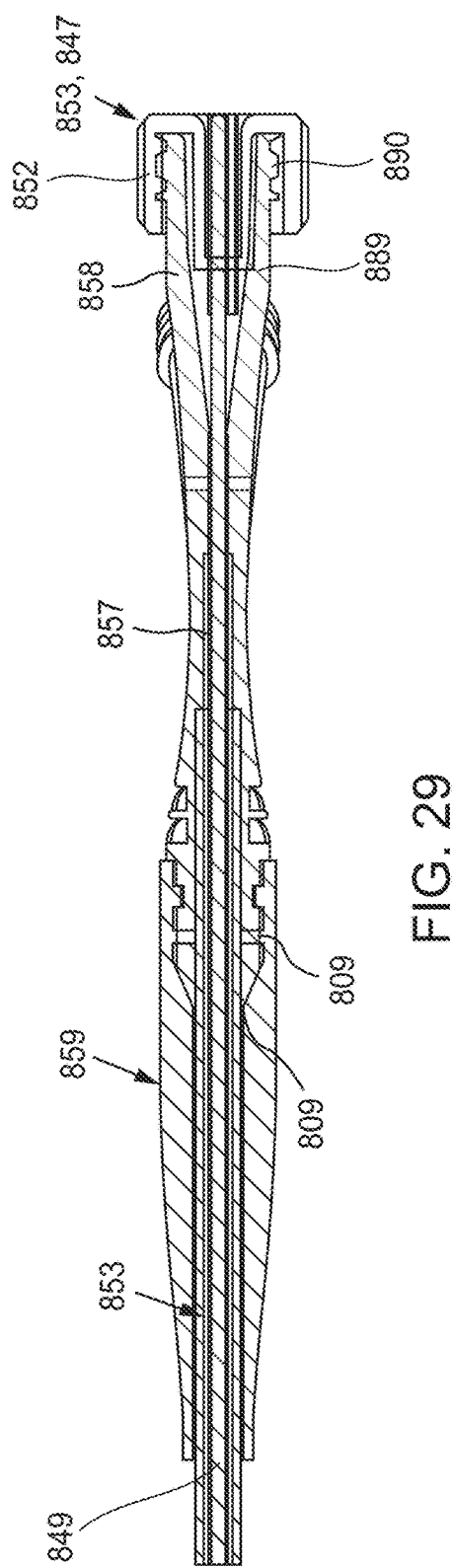
FIG. 29 is a cross-sectional view taken along line B-B in FIG. 28.

FIG. 29 is a cross-sectional view taken along line B-B in FIG. 28. As shown in FIGS. 28 and 29, the balloon manifold 856 includes a manifold hub 858 and a tapered strain relief portion 859 that relieves bending strain of inflation tube 855 relative to relatively rigid manifold hub 858. The manifold hub 858 and the strain relief portion 859 can be coupled together, for example, via adhesive, at, for example, locations 809.

As shown in FIGS. 28 and 29, a shipping mandrel 853 can be inserted through the guidewire lumen of the guidewire tube 857 and includes an elongate member 849 coupled to a proximal knob 847. The elongate member 849 can be inserted through the balloon manifold 856 and the elongate guidewire tube 857 until a distal end is disposed outside a distal end of the inflation tube 857 as shown in FIG. 28. The shipping mandrel 853 can be used to maintain the alignment of the various components of the dilator device 854 and reduce or eliminate the possibility of the guidewire tube 857 collapsing prior to use of the dilator device 854. In this embodiment, the proximal knob 847 of the shipping mandrel 853 can be coupled to the balloon manifold 856 with a quick connect coupler, such as, for example, a Luer lock coupling mechanism. For example, the proximal knob 847 can include a Luer lock feature 852 that can be matingly coupled to a Luer lock feature 890 of the guidewire port 889 of the balloon manifold 856. Before use of the dilator device 854, the shipping mandrel 853 can be removed from the dilator device 854 by releasing the Luer lock feature 852 from the Luer lock feature 890 of the guidewire port 889 and pulling the shipping mandrel 853 proximally such that the shipping mandrel 853 is removed from the elongate guidewire tube 857 and the balloon manifold 856.

FIG. 30 is a side view of the balloon member 834 in the partially inflated/expanded configuration. The balloon member 834 includes a first body portion 831 and a second body portion 833 having a first outer diameter and a second outer diameter, respectively. The second outer diameter is larger than the first outer diameter. Distal end portion of the balloon member 834 includes a tapered concave distal portion 835 and a distal neck portion 839. Proximal end portion of the balloon member 834 includes a cone-shaped portion 838 and a proximal neck portion 881.

The balloon member 834, and the individual portions of the balloon member 834, can have any suitable length. For example, the concave distal portion 835, the first body portion 831, and the second body portion 833 can have a combined length $L_1$. In some embodiments, the length $L_1$ can be, for example, about 3.723 inches. The concave distal portion 835 can have a length $L_2$, the first body portion 831 can have a length $L_3$, and the second body portion 833 can have a length $L_4$. In some embodiments, the length $L_2$ can be, for example, about 1.350 inches, the length $L_3$ can be, for example, about 1.25 inches, and the length $L_4$ can be, for example, about 0.75 inches. Additionally, in some embodiments, the tapered concave distal portion 835 can include a hydrophilic coating.

Figure 31:
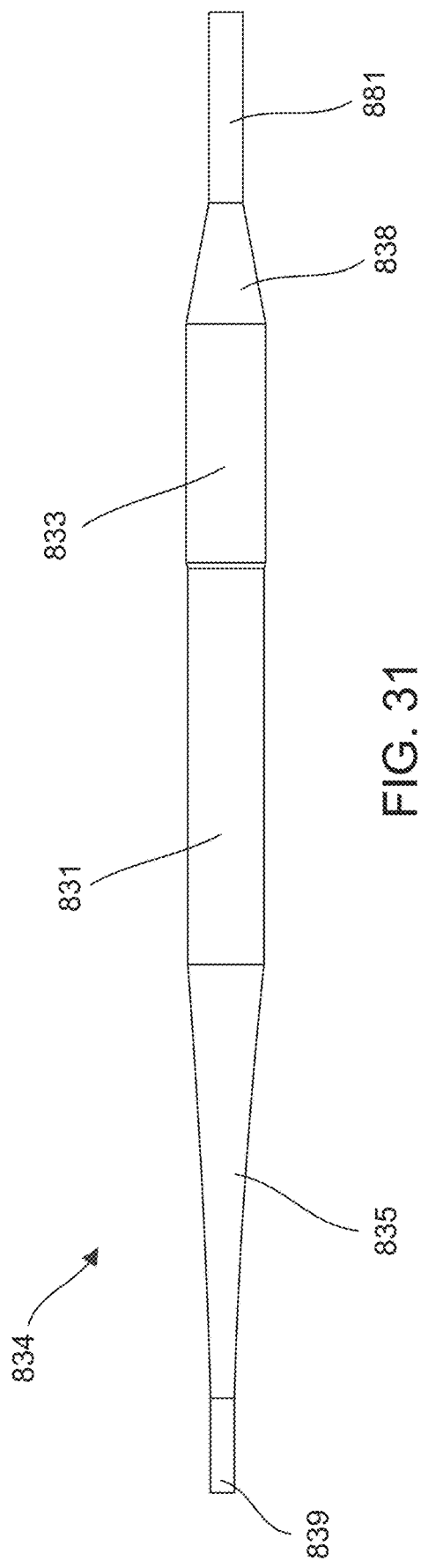
FIG. 31 is a side view of the balloon member of the dilator device of FIG. 28 in a collapsed configuration.

In some embodiments, the distal neck portion 839 can have a length $L_5$ that can be, for example, about 0.30 inches, and the proximal neck portion 881 can have a length $L_6$ that can be, for example, about 0.60 inches. The cone-shaped portion 838 can taper from the second body portion 833 to the proximal neck portion 881 at any suitable angle. For example, the taper of the cone-shaped portion 838 relative to the proximal neck portion 838 can be an angle $\theta_1$. In some embodiments, the angle $\theta_1$ can be, for example, 25°. When in an uninflated configuration, as shown in FIG. 31, the balloon member 834 can be folded or collapsed to a smaller size for insertion into a delivery sheath.

In some situations, depending on the inflation pressure of the balloon member 834, the concave distal portion 835 can expand to a non-concave shape when the balloon member 834 is expanded to an inflated configuration. In such a case, the distal portion 835 may be tapered, but not concave. In some embodiments, the balloon member 834 can be configured such that the target pressure in the balloon is 2-3 ATM in an inflated configuration for use. At 2-3 ATM, the concave distal portion 835 can be configured to maintain a concave shape or a slightly more straightened tapered shape.

FIG. 32 is an enlarged view of detail C in FIG. 30. As shown in FIG. 32, the balloon member 834 includes a first transition portion 831A and a second transition portion 833A between the first body portion 831 and the second body portion 833. The first transition portion 831A and the second transition portion 833A provide a smooth and radiused transition between the first body portion 831 and the second body portion 833.

FIG. 33 is a distal end view of the balloon member 834 shown in FIG. 30. As shown in FIG. 33, and described above, the outer diameter of the second body portion 833 is larger than the outer diameter of the first body portion 831. For example, in some embodiments, the second body portion 833 can have an outer diameter of about 0.455 inches and the first body portion 831 can have an outer diameter of about 0.445 inches. The first outer diameter can be selected such that, when the first body portion 831 is disposed within a sheath such as sheath 336 described above, there is a smooth transition between the concave distal portion 835 and the sheath 336. Additionally, the first body portion 831 can include a hydrophilic coating. The second outer diameter (of the second body portion 833) can be selected such that, in an expanded configuration, when disposed inside a delivery sheath (such as sheath 336 described above), the second body portion 833 can create a seal against the inner surface of the delivery sheath. Said another way, when unrestrained and in an expanded/inflated configuration, the second outer diameter of the second body portion 833 can be larger than the inner diameter of the sheath.

Figure 34:
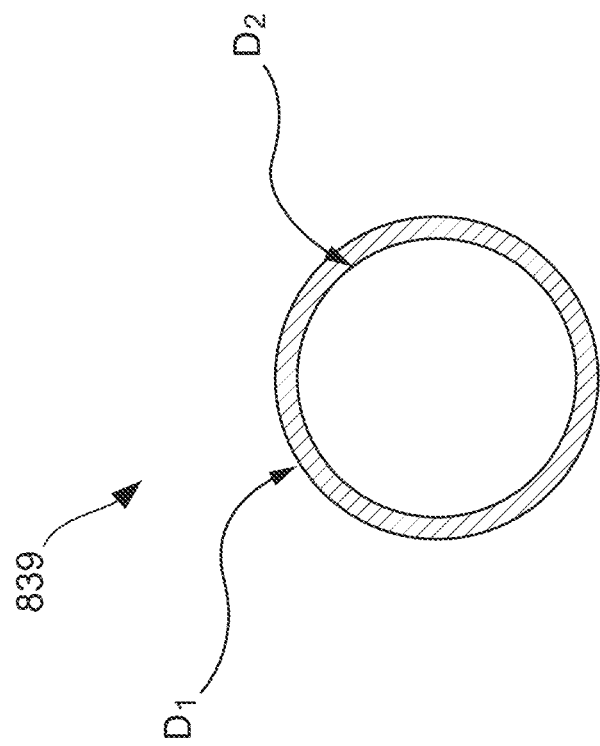
FIG. 34 is a cross-sectional view taken along the line D-D in FIG. 30.

FIG. 34 is a cross-sectional view taken along the line D-D shown in FIG. 30. As shown in FIG. 34, the distal neck portion 839 has an outer diameter $D_1$ and an inner diameter $D_2$. In some embodiments, the outer diameter $D_1$ can be, for example, about 0.064 inches and the inner diameter $D_2$ can be, for example, about 0.056 inches.

Figure 35:
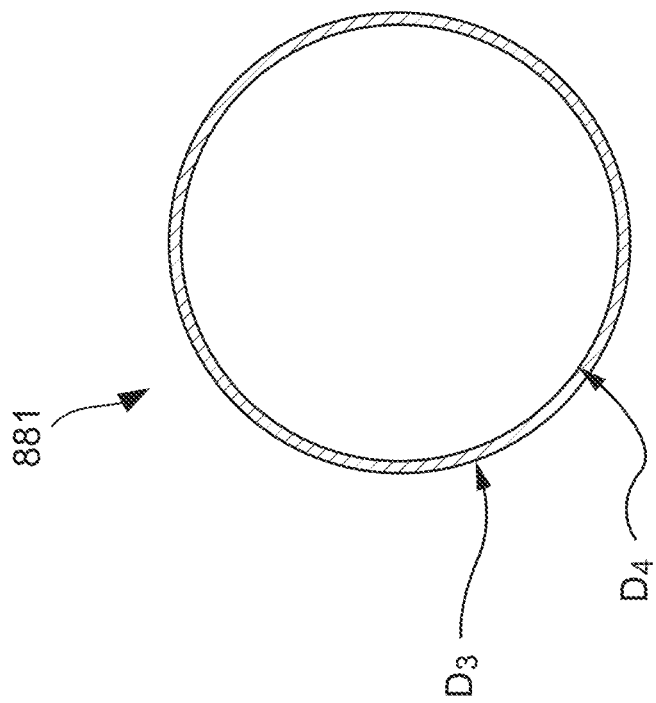
FIG. 35 is a cross-sectional view taken along the line E-E in FIG. 30.

FIG. 35 is a cross-sectional view taken along the line E-E shown in FIG. 30. As shown in FIG. 35, the proximal neck portion 881 has an outer diameter $D_3$ and an inner diameter $D_4$. In some embodiments, the outer diameter $D_3$ can be, for example, about 0.1075 inches and the inner diameter $D_4$ can be, for example, about 0.103 inches.

Figure 36:
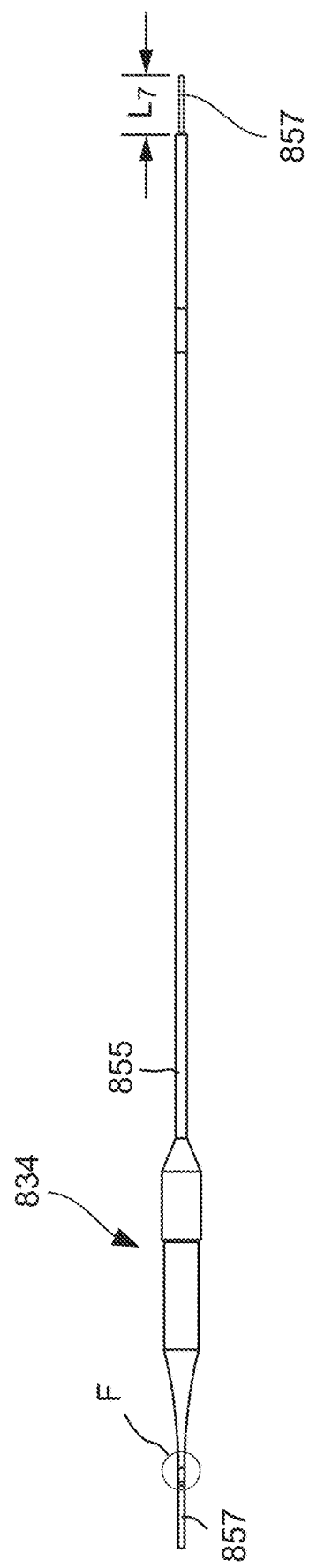
FIG. 36 is a side view of the balloon member, the elongate inflation tube, and the elongate guidewire tube of the dilator device of FIG. 28.

FIG. 36 is a side view of the balloon member 834, the elongate inflation tube 855, and the elongate guidewire tube 857. As described above, the elongate guidewire tube 857 is disposed through the balloon inflation tube 855. A distal portion of the elongate guidewire tube 857 extends distally of the balloon member 834 and a proximal portion of the elongate guidewire tube 857 extends proximally of the proximal end of the elongate inflation tube 855 by a length $L_7$. The length $L_7$ can be any suitable length that can engage with the balloon inflation manifold 856 (shown in FIGS. 28 and 29) such that the guidewire lumen defined by the elongate guidewire tube 857 is accessible via the guidewire port 889. For example, in some embodiments, the length $L_7$ can be about 0.668 inches.

Figure 37:
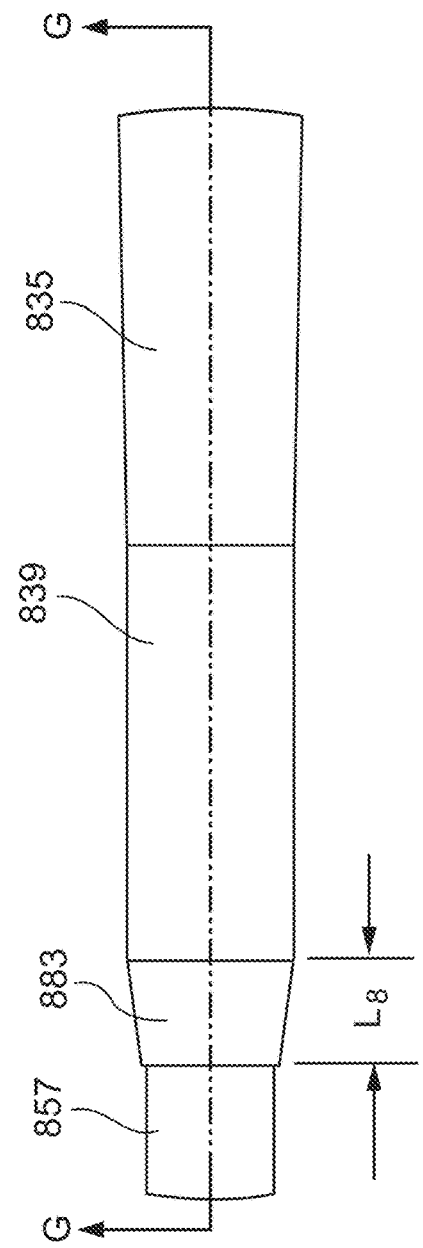
FIG. 37 is an enlarged view of detail F in FIG. 36.

FIG. 37 is an enlarged view of detail F identified in FIG. 36. As shown in FIG. 37, the distal neck portion 839 of the balloon member 834 can be coupled to the elongate guidewire tube 857 via an adhesive 883. The adhesive 883 can be applied such that it creates a smooth taper transition region between the outer surface of the elongate guidewire tube 857 and the outer surface of the distal neck portion 839. The taper of the adhesive 883 can be over a length $L_8$, which, in some embodiments can be, for example, about 0.04 inches.

Figure 38:
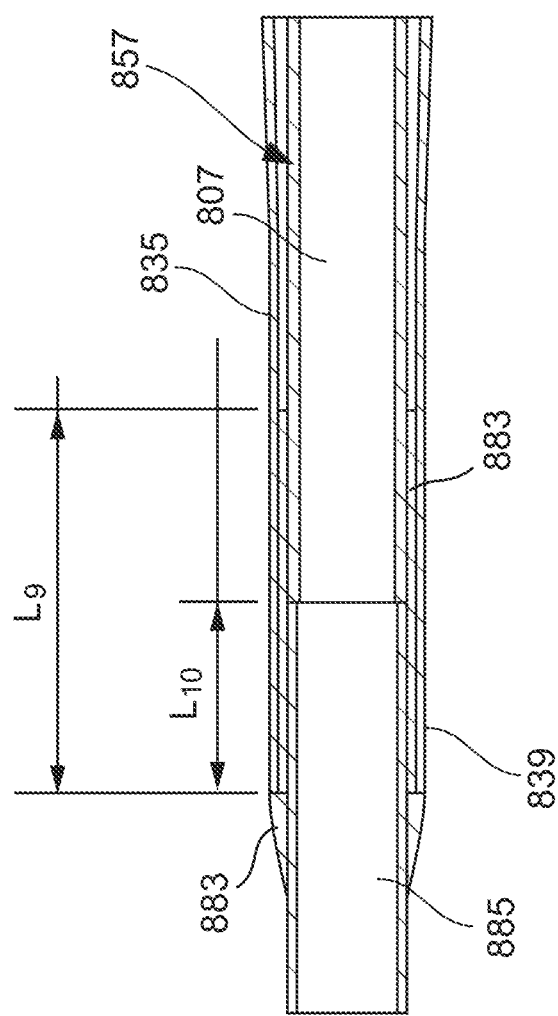
FIG. 38 is a cross-section view taken along the line G-G in FIG. 37.

FIG. 38 is a cross-sectional view of the enlarged detail of FIG. 37 taken along the line G-G in FIG. 32. As shown in FIG. 38, the adhesive 883 coupling the elongate inflation tube 855 to the distal neck portion 839 of the balloon member 834 can also be disposed over a length $L_9$ between an inner surface of the distal neck portion 839 and the outer surface of the elongate guidewire tube 857. In some embodiments, the length $L_9$ can be, for example, between about 0.160 inches and about 0.320 inches.

Additionally, as shown in FIG. 38, the elongate guidewire tube 857 can include a first portion 885 at a distal end (also referred to as distal end portion 885) that can be formed with a softer material than a remaining second portion 807 of the elongate guidewire tube 857 to provide an atraumatic distal end to reduce potential trauma to surrounding tissue when inserted into a patient's heart. For example, in some embodiments, the distal end portion 885 can be formed with a low durometer material, such as, Pebax®, cross-linked Pebax®, nylon, urethane, or the like. The elongate guidewire tube 857 can be disposed within the distal neck portion 839 such that the distal end portion 885 of the elongate guidewire tube 857 overlaps the distal neck portion 839 of the balloon member 834 by a length $L_{10}$. In some embodiments, the length $L_{10}$ can be, for example, about 0.080 inches. The remaining second portion 807 of the guidewire tube 857 can be formed with multiple layers to provide improved guidewire movement, kink resistance and bondability. For example, in some embodiments, the remaining second portion 807 of the guidewire tube 857 can be formed with a three layer construction including an inner layer of PTFE/PI composite material, a coil material formed with, for example, 304V Stainless steel, and an outer layer of material formed with Pebax® 7233 SA01 for medical use. The first or distal end portion 885 of the guidewire tube 857 can have a larger inner diameter than an outer diameter of the second portion 807 of the guidewire tube 857 such that a distal end of the second portion 807 can be received within the lumen of the distal end portion 885. The first or distal end portion 885 can also be coupled to the second portion of the guidewire tube 857 with an adhesive disposed between the outer surface of the remaining portion and the distal end portion 885.

Figure 39:
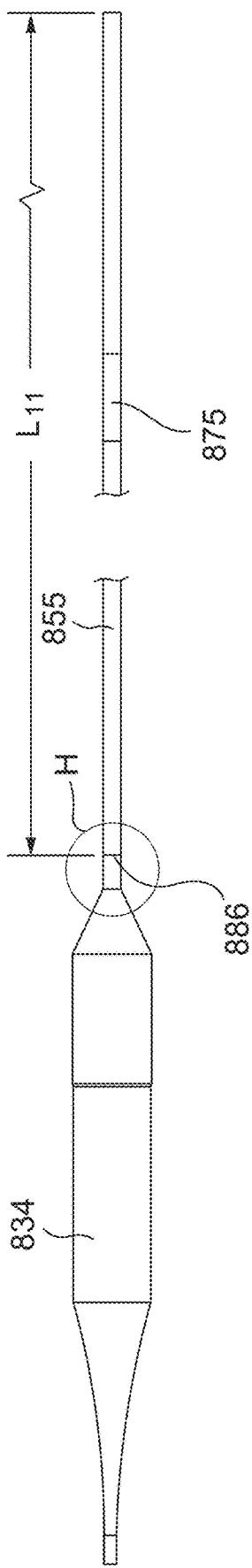
FIG. 39 is a side view of the balloon member and the elongate inflation tube of FIG. 28.

FIG. 39 is a side view of the balloon member 834 coupled to the elongate inflation tube 855. As shown in FIG. 39, the proximal neck portion 881 of the balloon member 834 can be coupled to the elongate inflation tube 855. Also as shown, the elongate inflation tube 855 can have a length $L_{11}$. In some embodiments, the length $L_{11}$ can be, for example, about 11.12 inches. The elongate inflation tube 855 can be coupled to the balloon member 834 via an adhesive 886.

Figure 40:
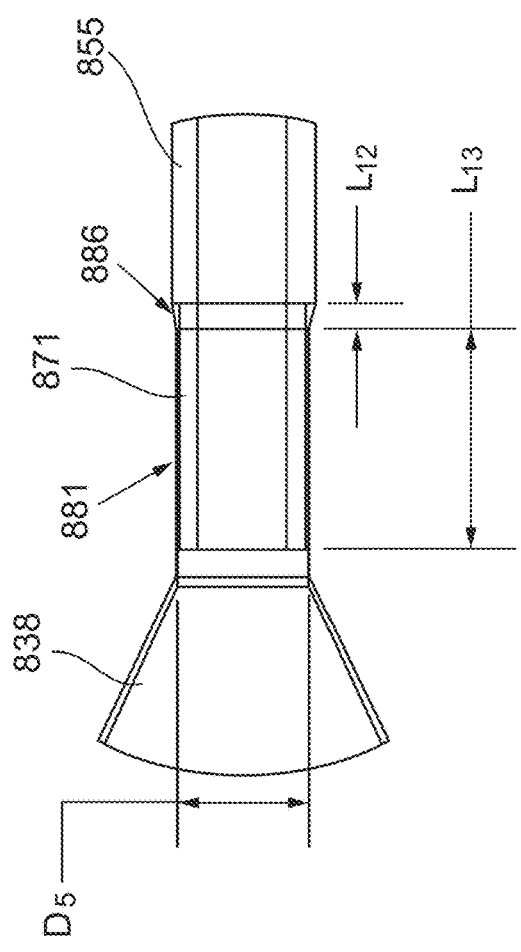
FIG. 40 is an enlarged view of detail H in FIG. 39.

FIG. 40 is an enlarged view of detail H in FIG. 39. As shown in FIG. 40, a distal end portion 871 of the elongate inflation tube 855 is disposed within the proximal neck portion 881 of the balloon member 834. The proximal neck portion 881 can have a diameter $D_5$, which in some embodiments can be, for example, about 0.116 inches or less. The distal end portion 871 of the elongate inflation tube 855 can have a smaller outer diameter $D_6$ than a diameter $D_7$ of the remaining portion 873 of the inflation tube 855 such that it can be inserted into the proximal neck portion 881 of the balloon member 834 (as shown in FIGS. 41 and 42). For example, in some embodiments, the diameter $D_6$ of the distal end portion 871 can be 0.099 inches, and the diameter $D_7$ of the remaining portion 873 of the inflation tube 855 can be, for example, 0.113 inches. In some embodiments, an inner diameter of the distal end portion 871 can be the same as inner diameter of the remaining portion 873 of the inflation tube 855 as shown in FIG. 41. In some embodiments, the distal end portion 871 and the remaining portion 873 of the inflation tube 855 can be formed as an integral or monolithically formed component. In some embodiments, the distal end portion 871 and the remaining portion 873 of the inflation tube 855 can be separate components that are coupled together.

As shown in FIG. 40, in some embodiments, the distal end portion 871 of the inflation tube 855 can be disposed a length $L_{13}$ into the proximal neck portion 881 of the balloon member 834. In some embodiments, the length $L_{13}$ can be, for example, at least about 0.125 inches. An adhesive 886 can be disposed between the proximal neck portion 881 of the balloon member 834 and the distal end portion 871 of the elongate inflation tube 855 to securely couple the proximal neck portion 881 to the elongate inflation tube 855. In some embodiments, the distal end portion 871 is inserted into the proximal neck portion 881 such that there is a small gap between the proximal end of the neck portion 881 and the larger diameter portion 873 of the inflation tube 885 and the adhesive 886 can be disposed within this gap and smoothed along the outer surface of the two components. The adhesive 886 can provide a smooth, tapered transition between the outer surface of the proximal neck portion 881 and the outer surface of elongate inflation tube 855. In some embodiments, the adhesive 886 can be disposed over a length $L_{12}$, which can be, for example, about 0.02 inches.

In use, as described above, the dilator device 854 can be used in conjunction with a delivery device such as the delivery devices 100, 200, 300, described above, to deliver and deploy a prosthetic mitral valve within a heart. When in an uninflated configuration (not shown), the dilator device 854 can be folded or collapsed and inserted through the hemostasis valve (not shown) coupled to a port of a hub of a catheter assembly (e.g., a port 237, 337 of a hub 232, 332 of a catheter assembly 230, 330). The dilator device 854 can be pushed or moved distally within the lumen of the delivery sheath 236, 336 until the concave distal portion 835 of the balloon member 834 extends distally of the distal end of the delivery sheath 236, 336 and the first body portion 831 and the second body portion 833 are disposed within the delivery sheath 236, 336. In some embodiments, the dilator device 854 can include a marker 875 (see FIG. 39) on an exterior of the inflation tube 855 to assist in the positioning of the dilator device 854 within the delivery sheath 236, 336. For example, the marker 875 can be disposed on the inflation tube 855 at a location such that as the dilator device 854 is inserted into the delivery sheath, when the marker 875 reaches the hemostasis valve coupled to the side port of the delivery sheath, the balloon 834 will be positioned at the correct location within the delivery sheath.

With the dilator device 854 coupled to the catheter assembly (e.g., disposed within the delivery sheath 236, 336 of the catheter assembly 230, 330), the catheter assembly can be coupled to or docked with the handle assembly of the delivery device (e.g., handle assembly 220, 320 of delivery device 200, 300). The shipping mandrel 853 can be decoupled from the guidewire port 889 and removed from the elongate guidewire tube 857 before or after the catheter assembly (e.g., 230, 330) is docked/coupled to the handle assembly (e.g., 220, 320) of the delivery device (e.g., 200, 300). After coupling the catheter assembly (with the dilator device coupled thereto) to the handle assembly, the delivery sheath can be purged of air and the balloon member 834 can be expanded from the uninflated configuration (e.g., folded or collapsed) to an inflated configuration such that the second body portion 833 creates a seal against the inner surface of the delivery sheath 236, 336. The entire assembly can be loaded over a guidewire (not shown) via the distal end of the lumen of the elongate guidewire tube 857. For example, a guidewire can be inserted into the patient's heart and extend outside the patient's body and a proximal end of the guidewire can be inserted into the distal end of the guidewire tube 857 and extended out the proximal end of the guidewire tube 857. With the guidewire inserted therethrough, the distal end portion of the dilator device 854 and delivery sheath 236, 336 can be inserted through the epicardial surface of the patient's heart (e.g. at the apex) and extended through the wall of the left ventricle and into the left atrium of the heart. The tapered distal end of the balloon member 834 helps to open or enlarge the entry opening at the epicardial surface. When the delivery sheath 236, 336 is in a desired location, the balloon member 834 can be deflated and the dilator device 854 can be removed from the delivery device 200, 300 via the port 237, 337. Then delivery device 200, 300 can be actuated to deliver the prosthetic mitral valve as described above with reference to previous embodiments.

Figure 43:
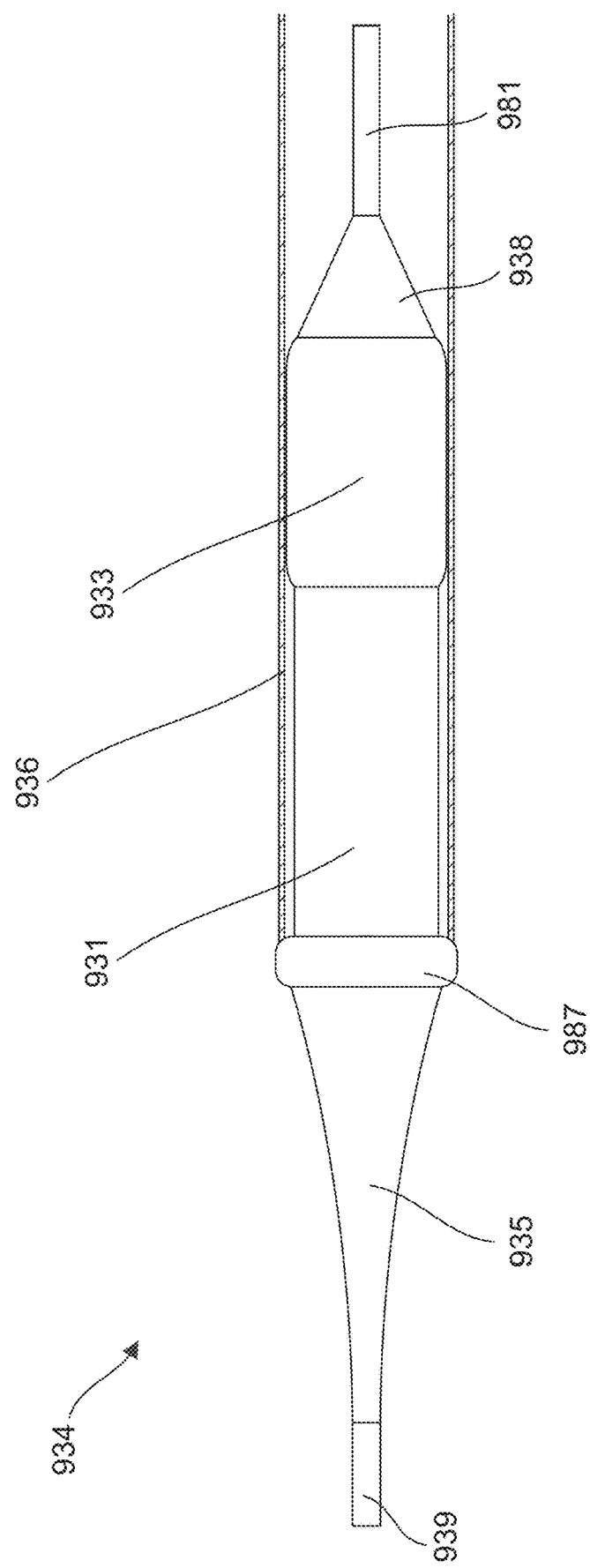
FIG. 43 is a side view of a balloon member of a dilator device, according to another embodiment shown disposed partially within a delivery sheath.

FIG. 43 is side view of a balloon member 934 engaged with a sheath 936 shown in cross-section. The balloon member 934 can be similar to the balloon member 934. For example, the dilation device 934 includes a first body portion 931 and a second body portion 933 having a first outer diameter and a second outer diameter, respectively. The second outer diameter is larger than the first outer diameter. The balloon member 934 also includes a tapered concave distal portion 935 and a distal neck portion 939. On the proximal side, the balloon member 934 includes a cone-shaped proximal portion 938 and a proximal neck portion 981.

In this embodiment, the balloon member 934 also includes an enlarged portion 987. The enlarged portion 987 can be shaped as a ring and has an increased outer diameter relative to the first body portion 931 when inflated (as shown in FIG. 43). The sheath 936 can be the same as or similar to the delivery sheaths 236 or 336 described above. As shown in FIG. 43, the sheath 936 can abut the proximal side of the enlarged portion 987. As a result of the abutment of the sheath 936 with the enlarged portion 987, the transition between the balloon 934 and the sheath 936 is smooth. Said another way, as the balloon member 934 and sheath 936 are moved through the epicardial surface, tissue will not catch on the distal end of the sheath 936. Additionally, the enlarged portion 987 can act as a limit or stop for the sheath 936 such that when the balloon member 934 is in the inflated configuration, the sheath 936 cannot translate distally beyond the enlarged portion 987.

Figure 44:
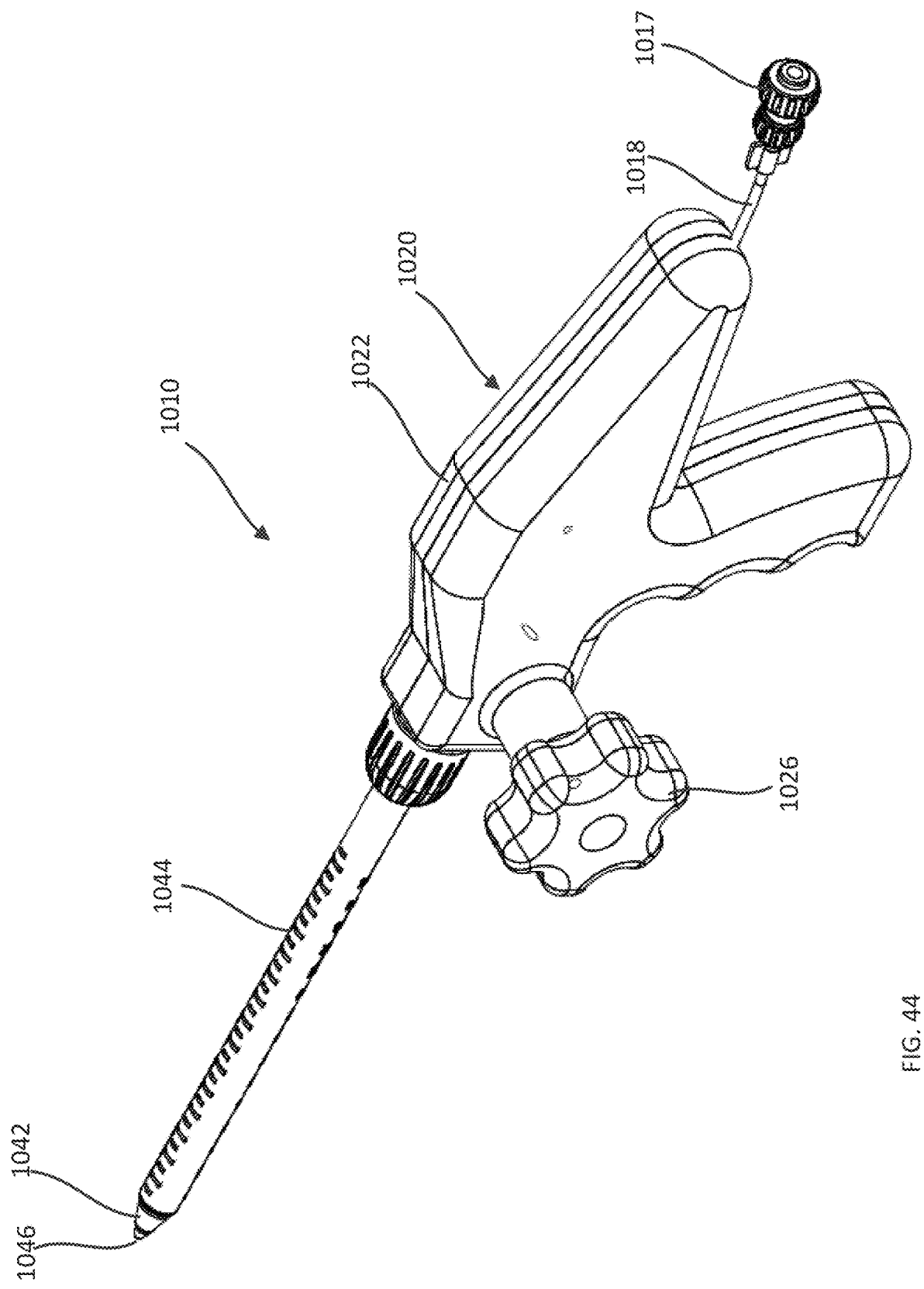
FIG. 44 is a perspective view of a recapture device, according to another embodiment.
Figure 45:
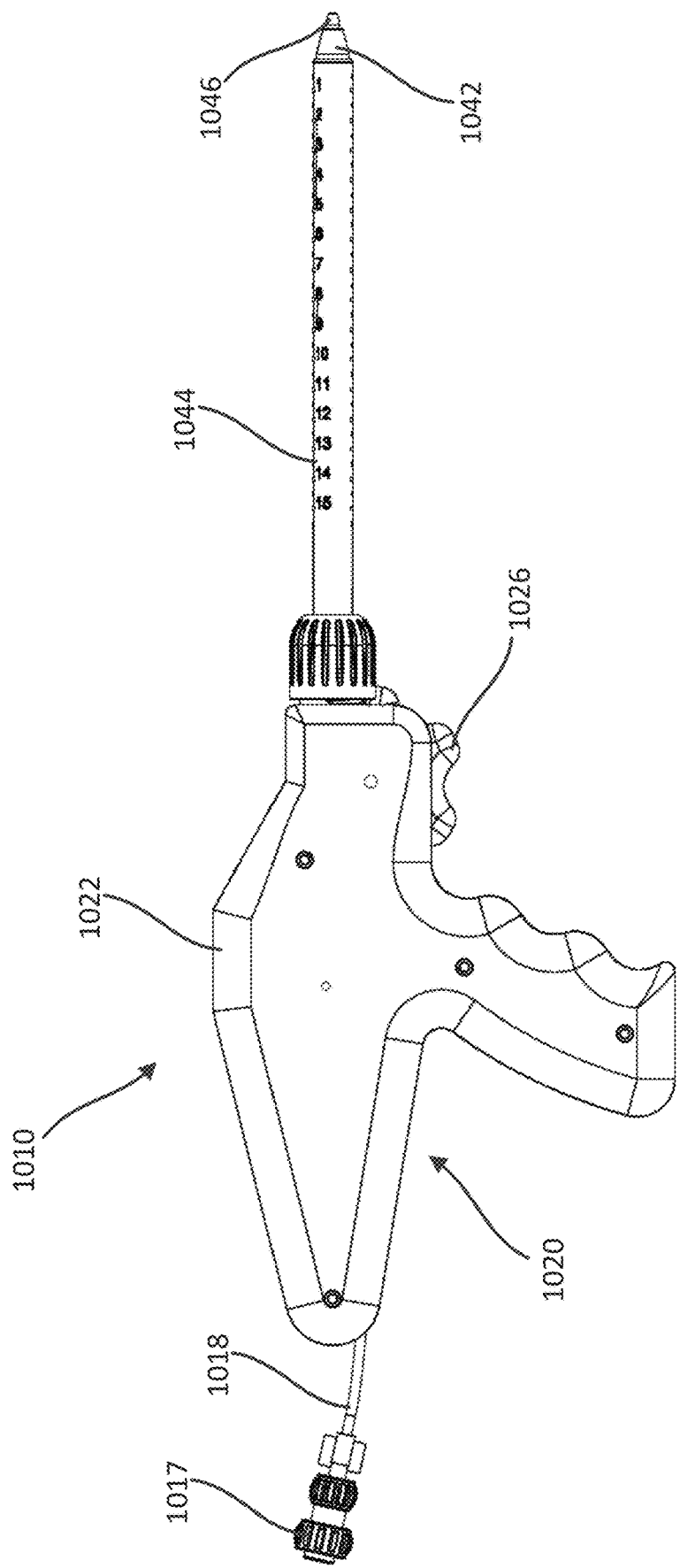
FIG. 45 is a side view of the recapture device of FIG. 44.
Figure 46:
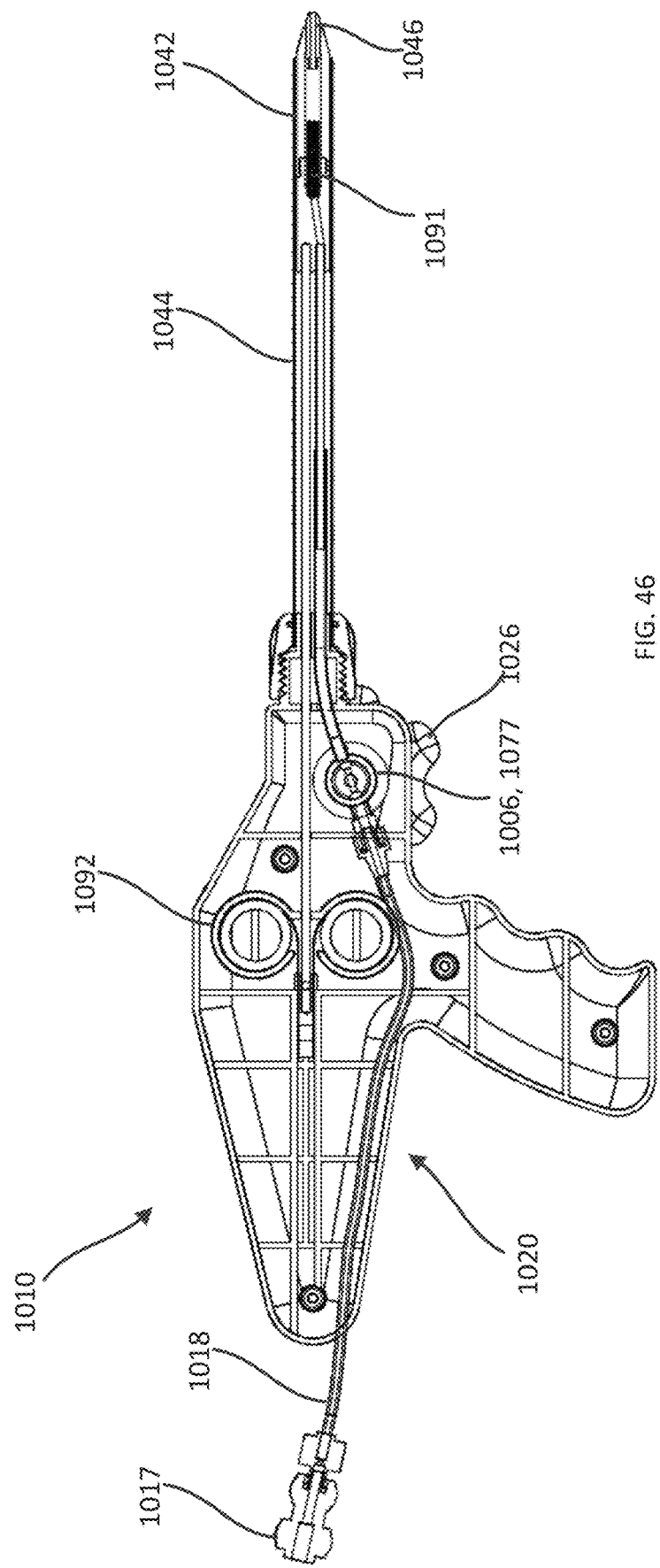
FIG. 46 is a side cross-sectional view of the recapture device of FIGS. 44 and 45.

FIGS. 44-46 illustrate another embodiment of a recapture device that can be used to recapture a deployed/implanted prosthetic heart valve (e.g., prosthetic mitral valve) to reposition and/or retrieve/remove the prosthetic heart valve. A recapture device 1010 includes an outer sheath 1044 coupled to a handle assembly 1020, an outer dilator 1042 operatively coupled to the handle assembly 1020 and movably disposed within a lumen of the outer sheath 1044, and an inner dilator 1046 movably disposed within a lumen of the outer dilator 1042 and operatively coupled to the handle assembly 1020. In this embodiment, the recapture device 1010 includes a tether retention mechanism that is incorporated into the actuator assembly as described in more detail below. The inner dilator 1046 defines a lumen that can receive a tether extending from a prosthetic valve (not shown) and can receive a portion of the prosthetic valve during a recapture procedure. The inner dilator 1046 also includes a distal tip configured to engage the prosthetic valve implanted within a heart as described in more detail below.

As shown in FIG. 46, the handle assembly 1020 includes a housing 1022, an actuator knob 1026 coupled to the housing 1022 and operatively coupled to a drive shaft mechanism 1006. The drive shaft mechanism 1006 is operatively coupled to the inner dilator 1046 and includes a winding housing 1077 that winds the tether (extending from the prosthetic valve) during the recapture procedure as described in more detail below. A first spring 1091 is coupled to an elongate tube 1079 and to the inner dilator 1046. The first spring 1091 can be, for example a coil spring. The outer dilator 1042 is coupled to an elongate rod 1093 which is coupled to a pair of tape springs 1092, which can be, for example, constant force springs, or variable force springs.

To capture a prosthetic heart valve with the recapture device 1010, the tether extending from the prosthetic valve can be inserted through a distal end of the inner dilator 1046, extend through the lumen of the inner dilator 1046, through the elongate tube 1079, through the winding housing 1077, through a hypotube 1018 and out a proximal end of the recapture device 1010. A Touhy valve 1017 is coupled to the hypotube 1018 and is configured to clamp the tether thereto and provide resistance as the tether is wound during a recapture procedure as described below. The valve 1017 can also provide a seal to allow for a saline flush of the system.

With the tether threaded through the recapture device 1010, the distal tip of the inner dilator 1046 can be moved distally along the tether to engage a proximal portion of the prosthetic valve. The actuator 1026 can then be actuated (e.g., rotate or turn the knob) to move the inner dilator 1046 proximally relative to the outer dilator 1042. As the inner dilator 1046 is moved proximally, the tether is wound within the winding housing 1077, and the valve will in turn be pulled proximally. For example, the tether can be wound from both directions into the winding housing 1077. One direction coming from the tether extending into the hypotube 1018 and the other direction being the tether entering the housing 1077 from the elongate tube 1079. The inner dilator 1046 can continue to be actuated to move proximally relative to the outer dilator 1042 pulling the prosthetic valve partially within the lumen of the outer dilator 1042 until the spring 1091 collapses fully and bottoms out against the outer dilator 1042 and the force on the spring 1091 increases. At this point, the valve has been partially captured and can be repositioned within the heart if desired.

To fully capture and retrieve/remove the valve, the actuator 1026 can continue to be actuated (e.g., rotated/turned), and due to the force of the spring 1091 against the outer dilator 1042, the outer dilator 1042 will begin to move proximally with the inner dilator 1046 and the valve coupled thereto. In other words, the inner dilator 1046 pulls the outer dilator 1042 proximally relative to the outer sheath 1044. The outer sheath 1044 remains fixed relative to the handle assembly 1020. As the outer dilator 1042 is moved proximally, the elongate rod 1093 engages with the tape springs 1092 and slides within a slot 1094. The springs 1092 coupled to the outer dilator 1042 via the elongate rod 1093 can control the force used to move the outer dilator 1042 proximally. In some embodiments, the springs 1092 can provide a constant force of, for example, 8-10 lbs. In some embodiments, the springs 1092 can provide a variable force. For example, it may be desirable to provide a greater spring force at the start of the actuation of the outer dilator 1042. As the outer dilator 1042 is moved proximally, the valve is pulled fully into the lumen of the outer sheath 1044 and moved to a collapsed configuration. The valve can then be removed/retrieved from the heart by removing the recapture device 1010 from the patient's body with the valve therein.

Figure 47:
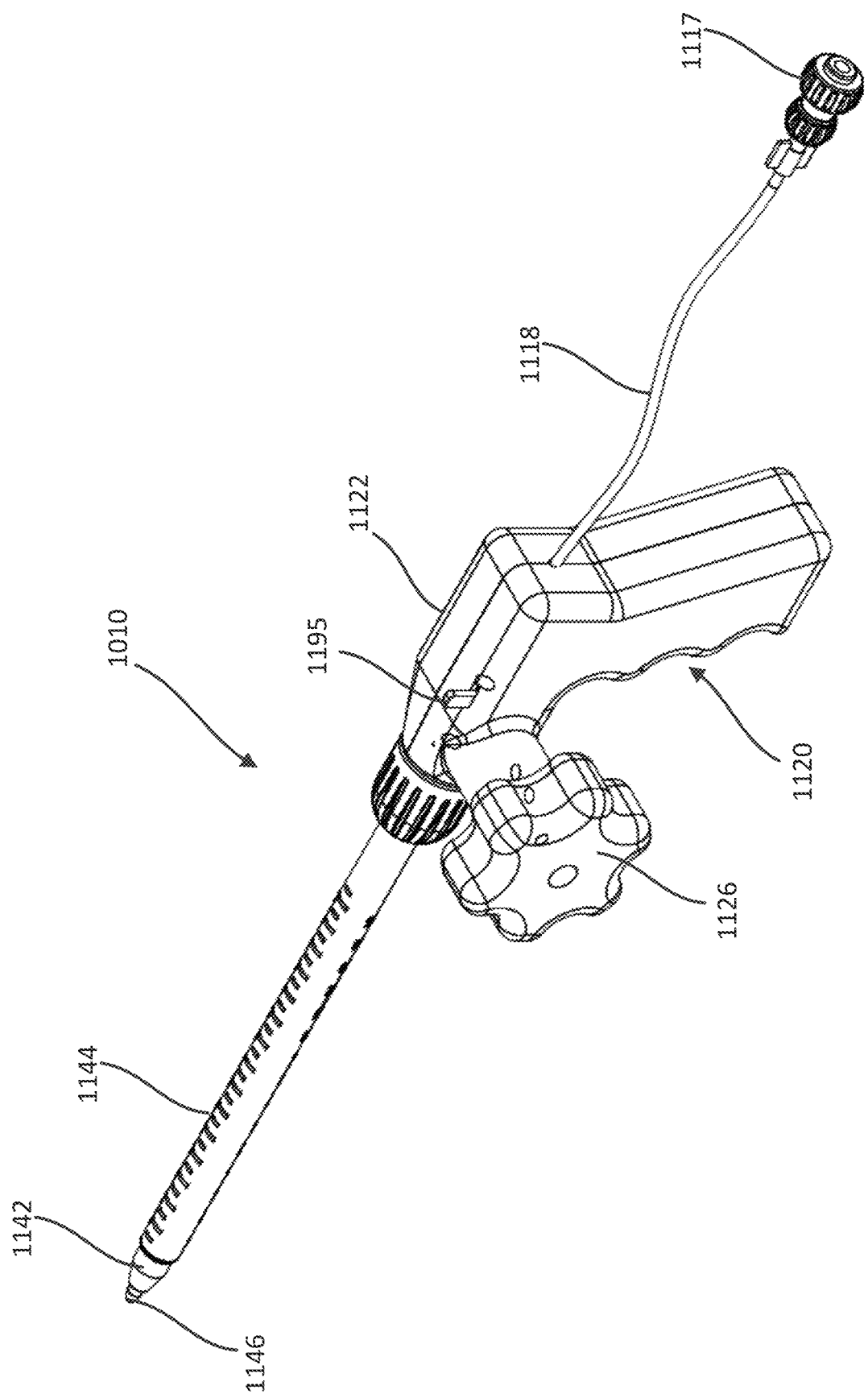
FIG. 47 is a perspective view of a recapture device, according to another embodiment.
Figure 48:
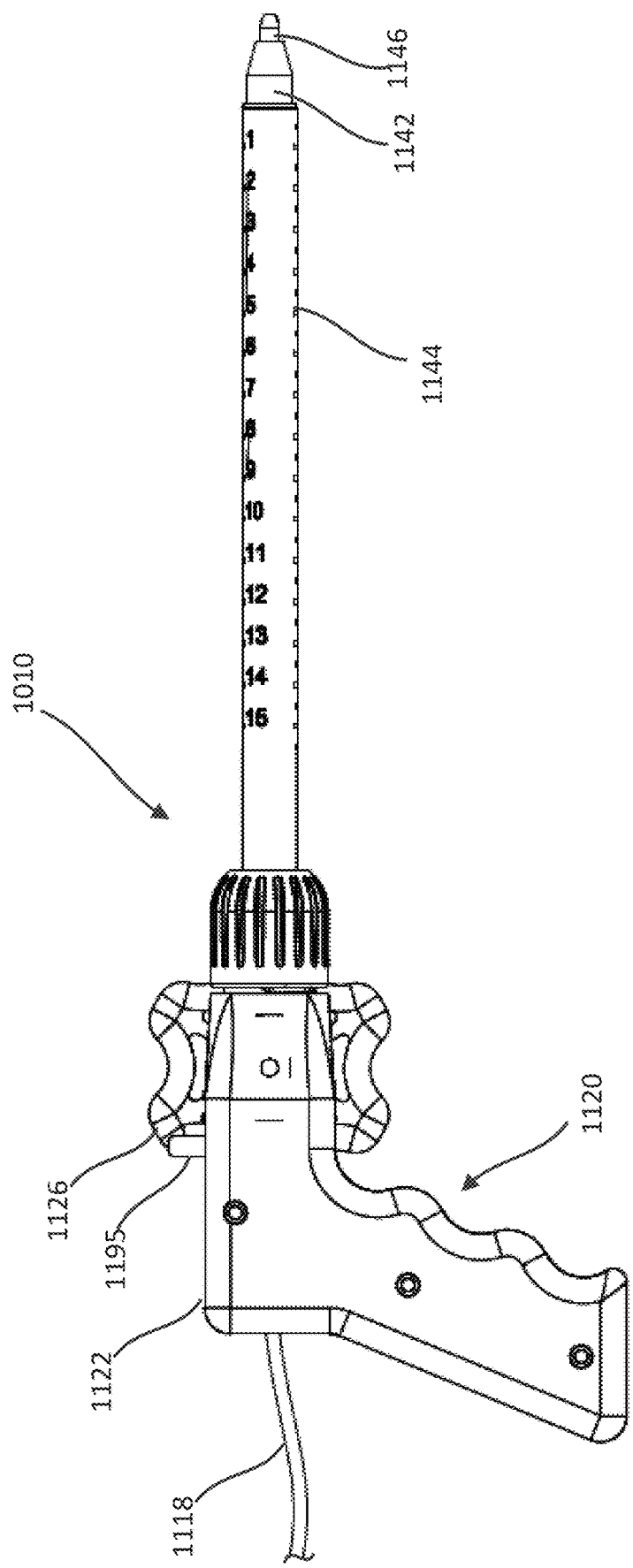
FIG. 48 is a side view of the recapture device of FIG. 47.
Figure 49:
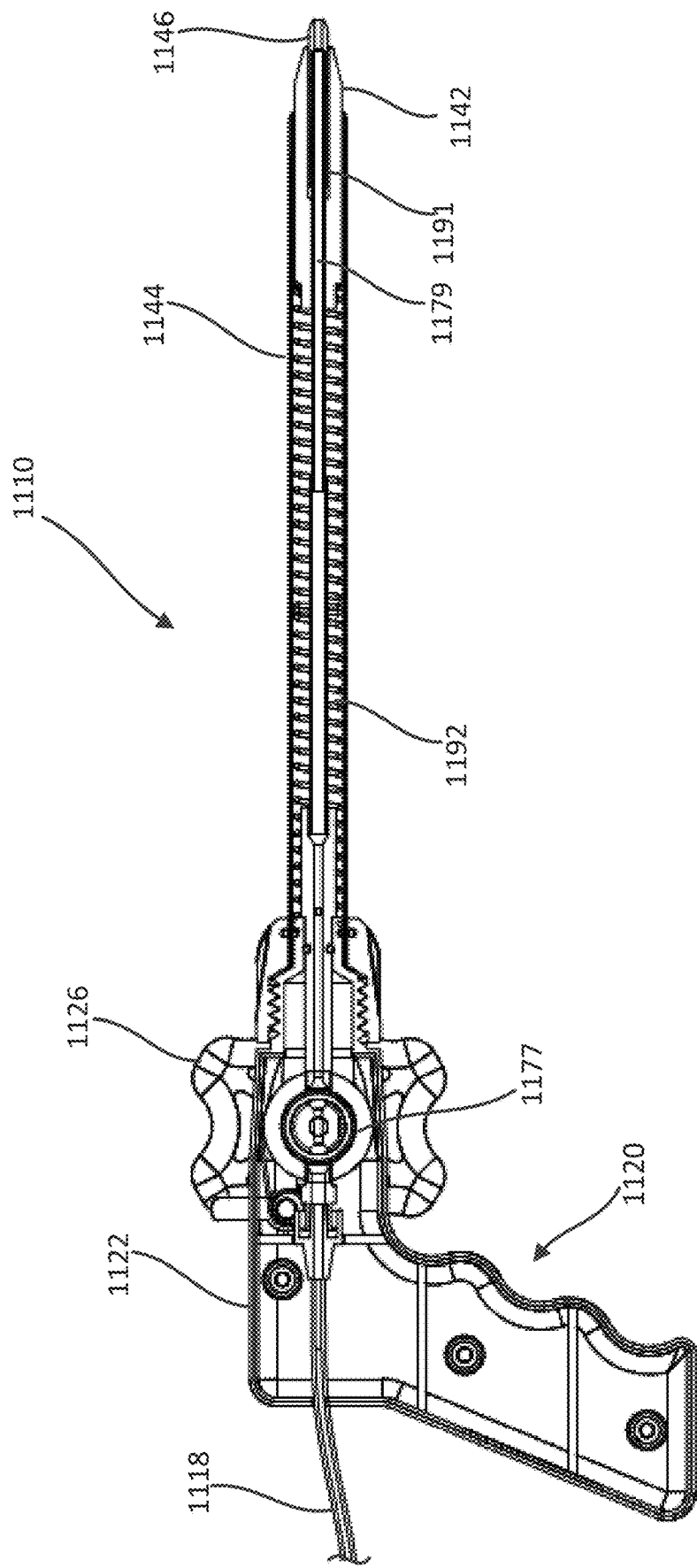
FIG. 49 is a side cross-sectional view of the recapture device of FIGS. 47 and 48.

FIGS. 47-49 illustrate another embodiment of a recapture device that can be used to recapture a deployed/implanted prosthetic heart valve (e.g., prosthetic mitral valve) to reposition and/or retrieve/remove the prosthetic heart valve. A recapture device 1110 includes an outer sheath 1144 coupled to a handle assembly 1120, an outer dilator 1142 operatively coupled to the handle assembly 1120 and movably disposed within a lumen of the outer sheath 1144, and an inner dilator 1146 movably disposed within a lumen of the outer dilator 1142 and operatively coupled to the handle assembly 1120. As with the previous embodiment, the recapture device 1110 includes a tether retention mechanism that is incorporated into the actuator assembly as described in more detail below. The inner dilator 1146 defines a lumen that can receive a tether extending from a prosthetic valve (not shown) and can receive a portion of the prosthetic valve during a recapture procedure. The inner dilator 1146 also includes a distal tip configured to engage the prosthetic valve implanted within a heart as described in more detail below.

As shown in FIG. 48, the handle assembly 1120 includes a housing 1122, an actuator knob 1126 coupled to the housing 1122 and operatively coupled to a drive shaft mechanism 1106. The drive shaft mechanism 1106 is operatively coupled to the inner dilator 1146 and includes a winding housing 1177 that winds the tether (extending from the prosthetic valve) during the recapture procedure as described in more detail below. A first spring 1191 is coupled to an elongate tube 1179 and to the inner dilator 1146. The first spring 1191 can be, for example a coil spring. In this embodiment, the outer dilator 1142 is coupled to the elongate rod 1179 which is also coupled to a second spring 1192, which can also be, for example, a coil spring. The spring 1191 has a softer spring rate than the second spring 1192. A release lever 1195 is couple to the drive shaft mechanism 1106 and can prevent the drive mechanism 1106 from moving backwards during a recapture procedure. If desired, however, the release lever 1195 can be actuated to allow the drive mechanism to back up if needed.

To capture a prosthetic heart valve with the recapture device 1110, the tether extending from the prosthetic valve can be inserted through a distal end of the inner dilator 1146, extend through the lumen of the inner dilator 1146, through the elongate tube 1179, through the winding housing 1177, through a hypotube 1118 and out a proximal end of the recapture device 1110. A Touhy valve 1117 is coupled to the hypotube 1118 and is configured to clamp the tether thereto and provide resistance as the tether is wound during a recapture procedure as described below. The valve 1117 can also provide a seal to allow for a saline flush of the system.

With the tether threaded through the recapture device 1110, the distal tip of the inner dilator 1146 can be moved distally along the tether to engage a proximal portion of the prosthetic valve. The actuator 1126 can then be actuated (e.g., rotate or turn the knob) to move the inner dilator 1146 proximally relative to the outer dilator 1142. As the inner dilator 1146 is moved proximally, the tether is wound within the winding housing 1177, and the valve will in turn be pulled proximally. For example, the tether can be wound from both directions into the winding housing 1177. One direction coming from the tether extending into the hypotube 1118 and the other direction being the tether entering the housing 1177 from the elongate tube 1179. The inner dilator 1146 can continue to be actuated to move proximally relative to the outer dilator 1142 pulling the prosthetic valve partially within the lumen of the outer dilator 1142 until the spring 1191 collapses fully and bottoms out against the outer dilator 1142 and the force on the spring 1191 increases. At this point, the valve has been partially captured and can be repositioned within the heart if desired.

To fully capture and retrieve/remove the valve, the actuator 1126 can continue to be actuated (e.g., rotated/turned), which will cause the outer dilator 1142 to begin to move proximally with the inner dilator 1146 and the valve coupled thereto. In other words, the inner dilator 1146 pulls the outer dilator 1142 proximally relative to the outer sheath 1144. The outer sheath 1144 remains fixed relative to the handle assembly 1120. As the outer dilator 1142 is moved proximally, the outer dilator 1142 applies a force against the second spring 1192. The second spring 1192 can help control the force used to move the outer dilator 1142 proximally. In some embodiments, the spring 1192 can provide a constant force of, for example, 8-10 lbs. In some embodiments, the springs 1191 and 1192 can each provide a variable force. As the outer dilator 1142 is moved proximally, the valve is pulled fully into the lumen of the outer sheath 1144 and moved to a collapsed configuration. The valve can then be removed/retrieved from the heart by removing the recapture device 1110 from the patient's body with the valve therein.

Figure 50:
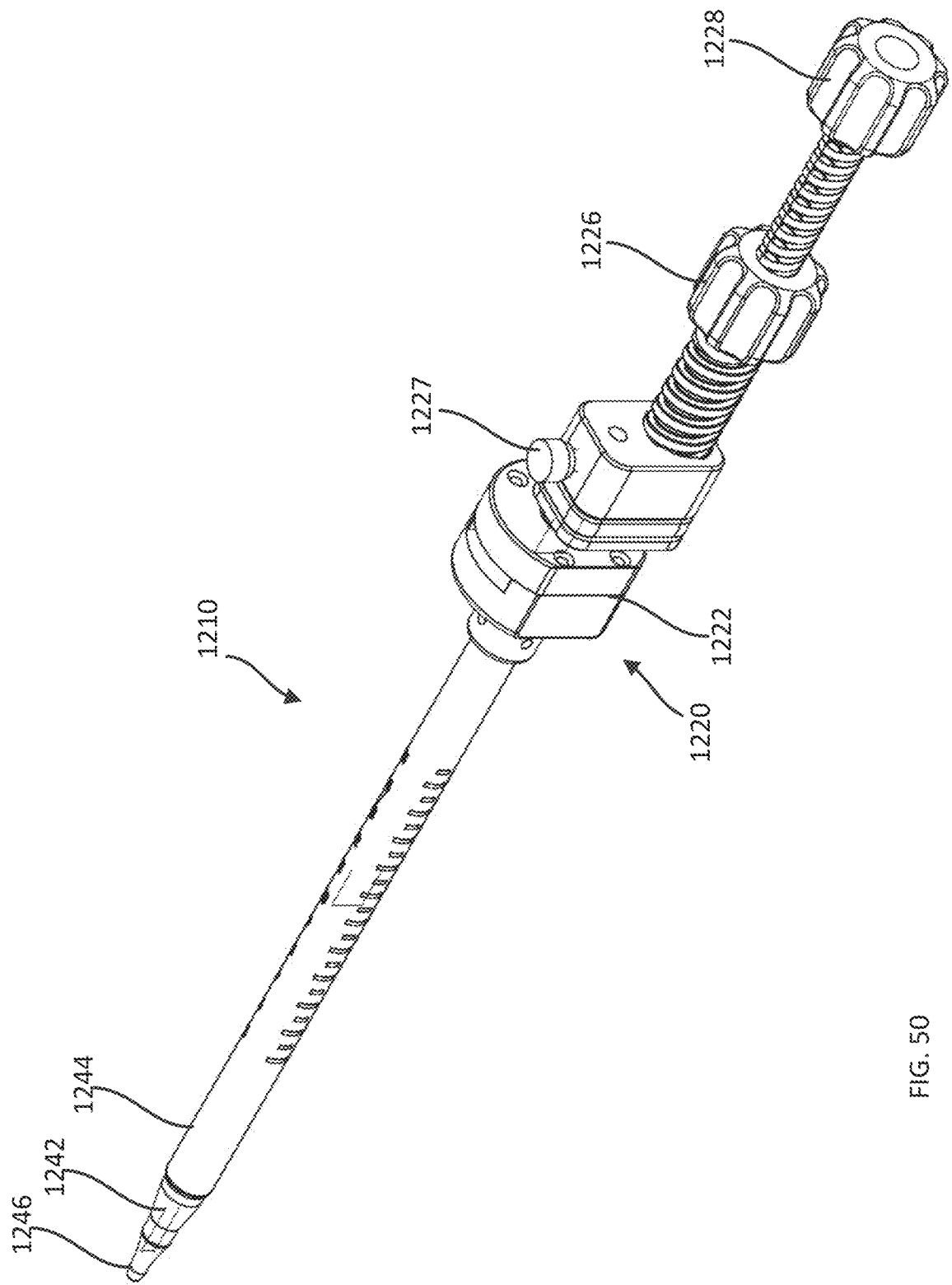
FIG. 50 is a perspective view of a recapture device, according to another embodiment.
Figure 51:
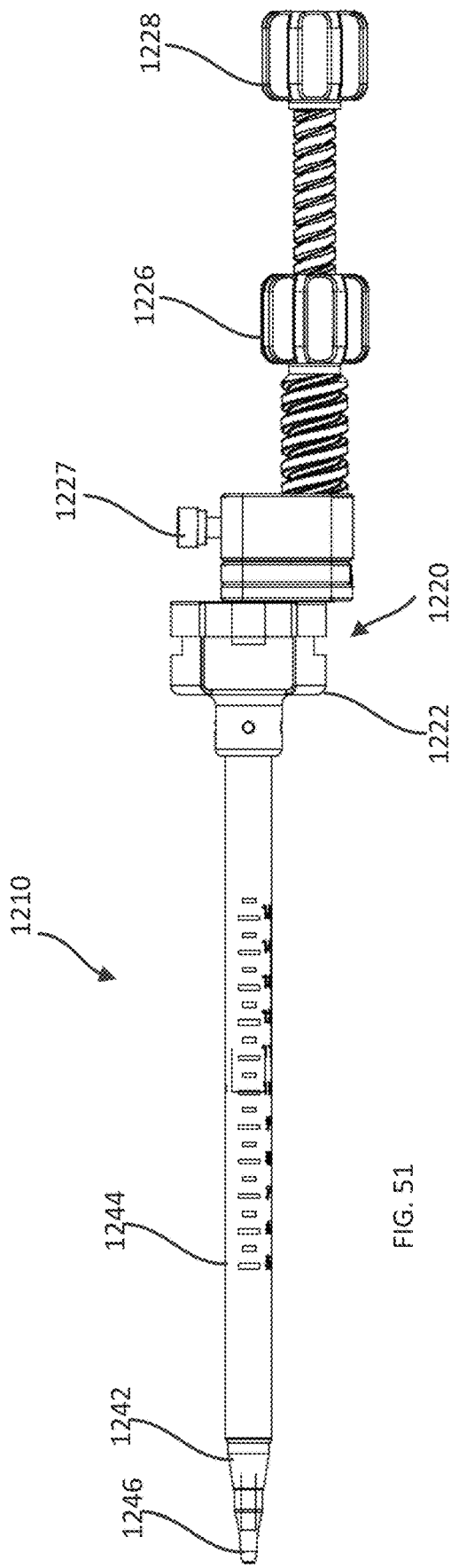
FIG. 51 is a side view of the recapture device of FIG. 50.
Figure 52:
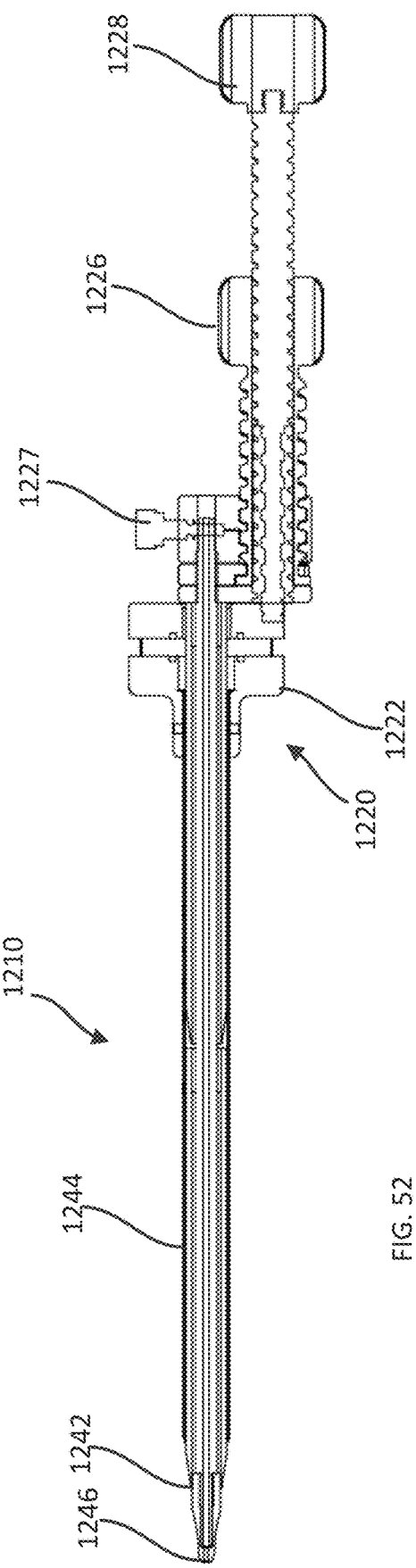
FIG. 52 is a side cross-sectional view of the recapture device of FIG. 50.

FIGS. 50-52 illustrate another embodiment of a recapture device that can be used to recapture a deployed/implanted prosthetic heart valve (e.g., prosthetic mitral valve) to reposition and/or retrieve/remove the prosthetic heart valve. A recapture device 1210 includes an outer sheath 1244 coupled to a handle assembly 1220, an outer dilator 1242 operatively coupled to the handle assembly 1220 and movably disposed within a lumen of the outer sheath 1244, and an inner dilator 1246 movably disposed within a lumen of the outer dilator 1242 and operatively coupled to the handle assembly 1220. The inner dilator 1246 defines a lumen that can receive a tether (not shown) extending from a prosthetic valve (not shown) and can receive a portion of the prosthetic valve during a recapture procedure. The inner dilator 1146 also includes a distal tip configured to engage the prosthetic valve implanted within a heart as described in more detail below. In this embodiment, the recapture device 1210 includes a tether retention mechanism 1227 that includes a pinning member that can pierce the tether and secure the tether to the recapture device 1210.

As shown in FIG. 52, the handle assembly 1220 includes a housing 1222, a first actuator knob 1226 operatively coupled to the inner dilator 1246, and a second actuator knob 1228 operatively coupled to the outer dilator 1242. An elongate tube 1279 is coupled to the inner dilator 1246 and extends through the housing 1222 and is coupled to the tether retention mechanism 1227.

To capture a prosthetic heart valve with the recapture device 1210, the tether extending from the prosthetic valve can be inserted through a distal end of the inner dilator 1246, extend through the lumen of the inner dilator 1246, through the elongate tube 1279, and is pinned by the retention mechanism 1227 at a proximal end of the handle assembly 1220. With the tether threaded through the recapture device 1210, the distal tip of the inner dilator 1246 can be moved distally along the tether to engage a proximal portion of the prosthetic valve. The first actuator 1226 can then be actuated (e.g., rotate or turn the knob) to move the inner dilator 1246 proximally relative to the outer dilator 1242. As the inner dilator 1246 is moved proximally, the retention mechanism 1227 and tether coupled thereto are pulled with the inner dilator 1246, and the valve will in turn be pulled proximally. As the valve is pulled proximally, a portion of the valve will be pulled into the lumen of the outer dilator 1242 and moved to a collapsed configuration within the lumen. At this point, the valve has been partially captured and can be repositioned within the heart if desired.

To fully capture and retrieve/remove the valve, the second actuator knob 1228 can be actuated (e.g., rotated/turned), which will cause the outer dilator 1242 to begin to move proximally with the inner dilator 1246 and the valve coupled thereto. The outer sheath 1244 remains fixed relative to the handle assembly 1220. The outer dilator 1242 can be moved proximally until the valve is fully disposed within the outer sheath 1244 and moved to a collapsed configuration. The valve can then be removed/retrieved from the heart by removing the recapture device 1210 from the patient's body with the valve disposed therein.

FIGS. 53-56 illustrate another embodiment of a recapture device that can be used to recapture a deployed/implanted prosthetic heart valve (e.g., prosthetic mitral valve) to reposition and/or retrieve/remove the prosthetic heart valve. A recapture device 1310 includes an outer sheath 1344 coupled to a handle assembly 1320, an outer dilator 1342 operatively coupled to the handle assembly 1320 and movably disposed within a lumen of the outer sheath 1344, and an inner dilator 1346 movably disposed within a lumen of the outer dilator 1342 and operatively coupled to the handle assembly 1320. The inner dilator 1346 defines a lumen that can receive a tether (not shown) extending from a prosthetic valve (not shown) and can receive a portion of the prosthetic valve during a recapture procedure. The inner dilator 1346 also includes a distal tip configured to engage the prosthetic valve implanted within a heart as described in more detail below. In this embodiment, the recapture device 1310 includes a tether retention mechanism 1327 that includes a pinning member that can pierce the tether and secure the tether to the recapture device 1310.

Figure 53:
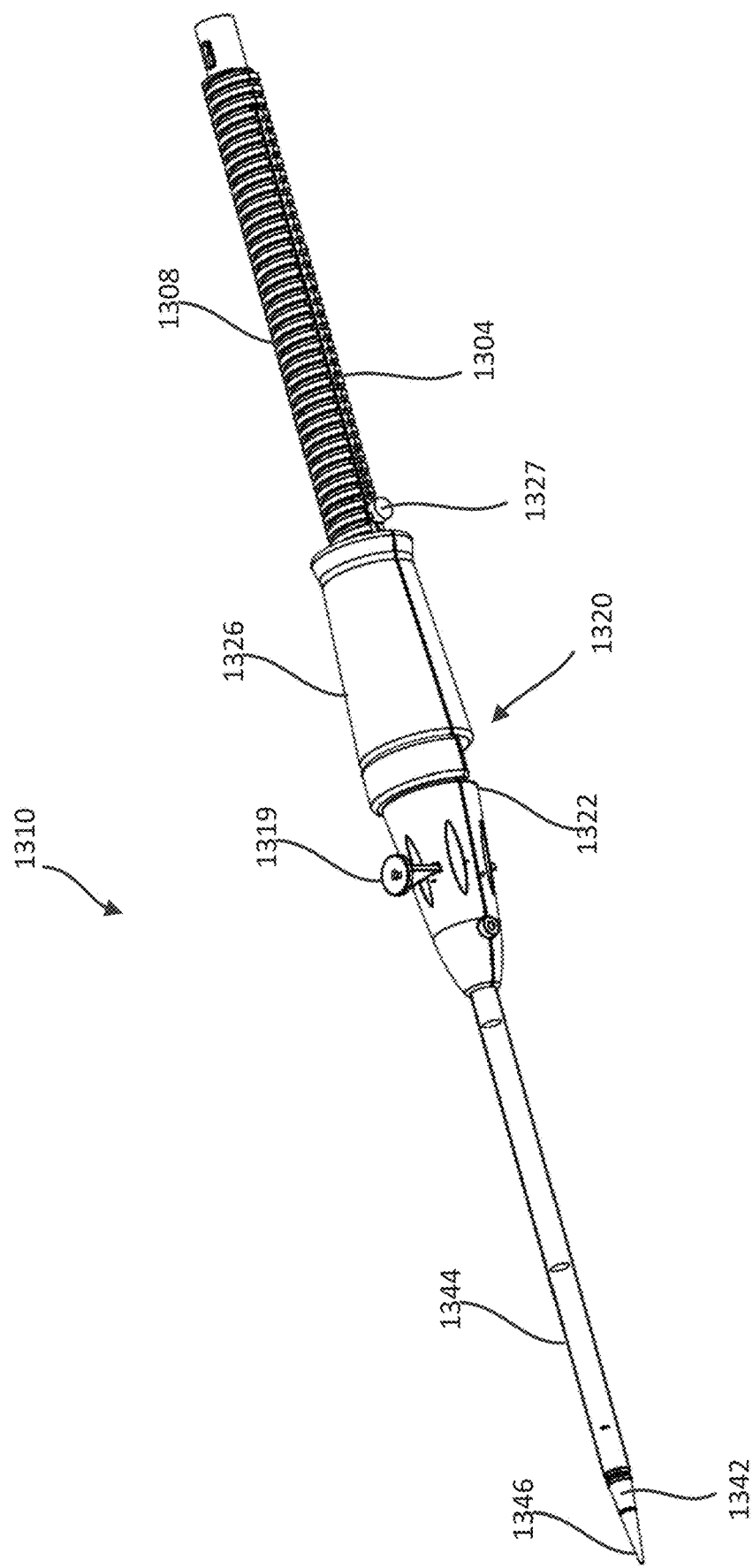
FIG. 53 is a perspective view of a recapture device, according to another embodiment.
Figure 54:
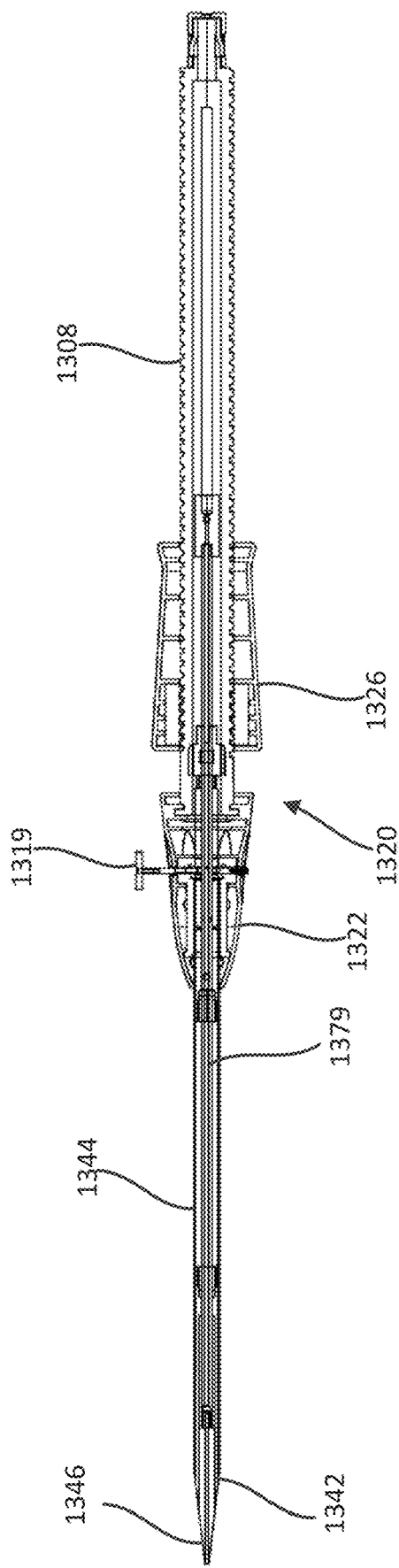
FIG. 54 is a side cross-sectional view of the recapture device of FIG. 53
Figure 55:
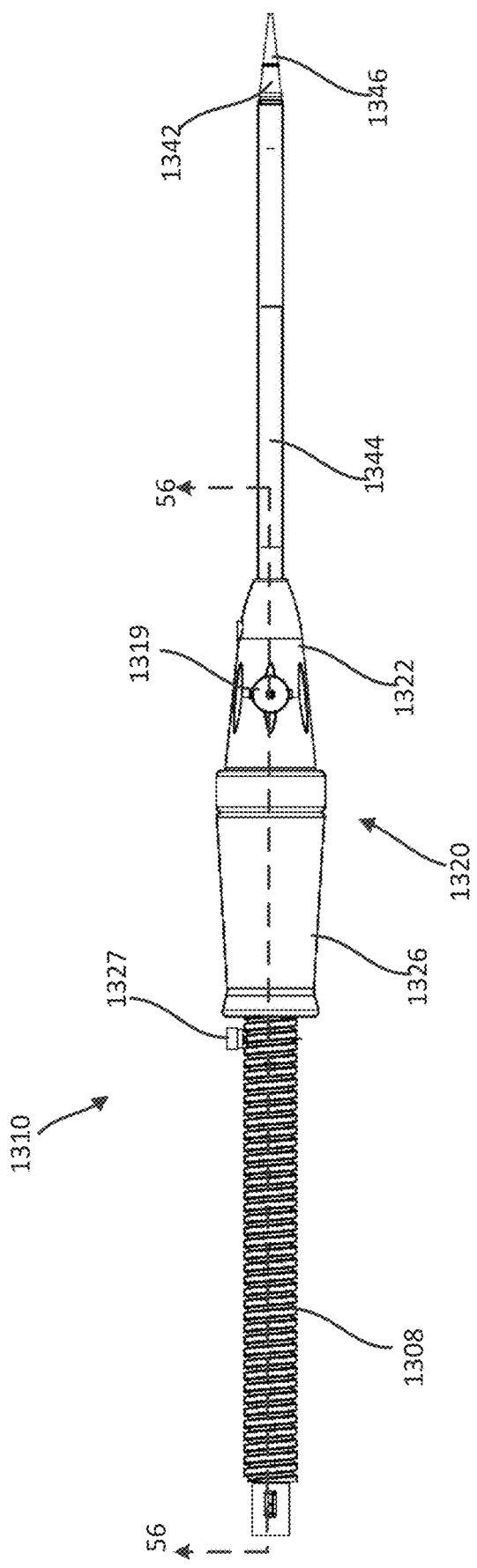
FIG. 55 is a top view of the recapture device of FIG. 53.
Figure 56:
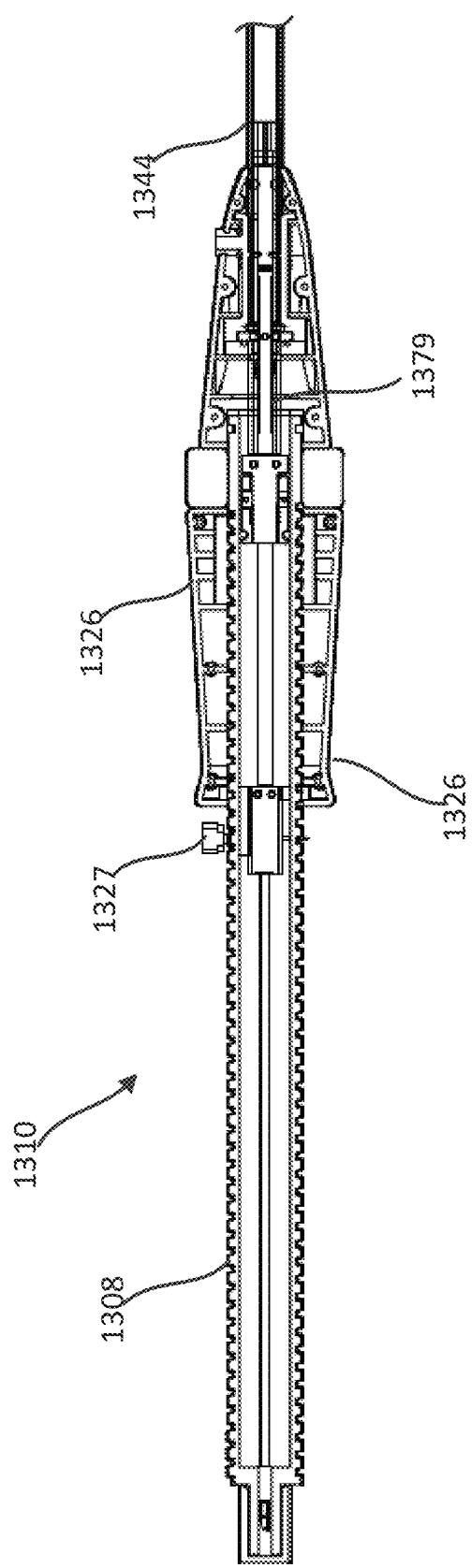
FIG. 56 is a cross-sectional view taken along line 56-56 in FIG. 55.

As shown in FIGS. 55 and 56, the handle assembly 1320 includes a housing 1322, an elongate threaded member 1308, and an actuator knob 1326. The actuator knob 1326 is operatively coupled to the inner dilator 1346 and to the outer dilator 1342. An elongate tube 1379 is coupled to the actuator knob 1326 and also to the inner dilator 1346 and to the outer dilator 1342, and extends through the housing 1322. The actuator knob 1326 can be actuated by rotating the actuator knob 1326, which causes the actuator knob to travel along the threaded member 1308. The tether retention mechanism 1327 is operatively coupled to the actuator knob 1326 such that when the actuator knob is actuated (e.g., rotated/turned) the tether retention mechanism 1327 moves with the actuator knob 1326 relative to the threaded member 1308. As shown in FIG. 53, the pinning member of the tether retention mechanism 1327 extends out a slot of the elongate threaded member 1308, and the tether retention mechanism 1327 can move along the slot 1307 as the actuator knob 1326 is actuated. In some embodiments, the actuator knob 1326 and/or threaded member 1308 includes a one-way mechanism that only allows the actuator knob 1326 to travel along the threaded member 1308 in one direction. This can prevent the actuator knob 1326 from being inadvertently moved back distally during a recapture procedure. A release lever 1319 is coupled to the outer dilator 1342 and is configured to releasably secure the outer dilator 1342 in a fixed position relative to the outer sheath 1344 as described in more detail below.

To capture a prosthetic heart valve with the recapture device 1310, the tether extending from the prosthetic valve can be inserted through a distal end of the inner dilator 1346, extend through the lumen of the inner dilator 1346, through the elongate tube 1379, and is pinned by the retention mechanism 1327. With the tether threaded through the recapture device 1310, the distal tip of the inner dilator 1346 can be moved distally along the tether to engage a proximal portion of the prosthetic valve. With the release lever 1319 engaged (e.g., pushed in) such that the outer dilator 1342 can't move relative to the outer sheath 1344, the actuator knob 1326 can be actuated (e.g., rotate or turn the knob) to move the inner dilator 1346 proximally relative to the outer dilator 1342 and relative to the outer sheath 1344. As the inner dilator 1346 is moved proximally, the retention mechanism 1327 and tether coupled thereto move proximally with the inner dilator 1346, and the valve will in turn be moved proximally such that a portion of the valve will be pulled into the lumen of the outer dilator 1342 and moved to a collapsed configuration within the lumen of the outer dilator 1342. At this point, the valve has been partially captured and can be repositioned within the heart if desired.

To fully capture and retrieve/remove the valve, the release lever 1319 can be pulled or moved to release the outer dilator 1342 from the outer sheath 1344. The actuator knob 1326 can be actuated to travel further proximally along the elongate threaded member 1308 which will cause the outer dilator 1342 to move proximally with the inner dilator 1346 and the valve coupled thereto. The outer sheath 1344 remains fixed relative to the handle assembly 1320. The outer dilator 1342 can be moved proximally until the valve is fully disposed within the lumen of the outer sheath 1344 and moved to a collapsed configuration. The valve can then be removed/retrieved from the heart by removing the recapture device 1310 from the patient's body with the valve disposed therein.

As described above for recapture device 410, each of the recapture devices described herein (i.e., 410, 1010, 1110, 1210, 1310) include a two-stage actuation of the recapture device that allows for a controlled capture of a prosthetic valve implanted within a heart to reposition and/or remove/retrieve the prosthetic valve. The proximal portion of the frame of the valve can first be collapsed sufficiently for a portion of the frame to be disposed within the lumen of the outer dilator (e.g., 442, 1042, 1142, 1242, 1342), and then can transition into a more fully collapsed configuration as it is moved into the lumen of the outer sheath (e.g., 444, 1044, 1144, 1244, 1344).

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

Where schematics and/or embodiments described above indicate certain components arranged in certain orientations or positions, the arrangement of components may be modified. While the embodiments have been particularly shown and described, it will be understood that various changes in form and details may be made. Any portion of the apparatus and/or methods described herein may be combined in any combination, except mutually exclusive combinations. The embodiments described herein can include various combinations and/or sub-combinations of the functions, components, and/or features of the different embodiments described.

What is claimed is:

1. An apparatus, comprising:
a recapture device configured to reposition or remove a prosthetic heart valve deployed within a heart, the recapture device including an outer sheath, an outer dilator, an inner dilator, and a handle assembly,
the outer sheath defining a first lumen,
the outer dilator defining a second lumen and movably disposed at least partially within the first lumen of the outer sheath,
the inner dilator defining a third lumen and movably disposed at least partially within the second lumen of the outer dilator, the inner dilator including a distal tip configured to engage a proximal portion of the prosthetic heart valve,
the handle assembly operatively coupled to the inner dilator and operatively coupled to the outer sheath, the handle assembly including a tether retention mechanism configured to secure a tether extending from the prosthetic heart valve to the handle assembly,
the inner dilator configured to be actuated to move the inner dilator proximally relative to the outer dilator when the tether extending from the prosthetic heart valve is secured to the tether retention mechanism such that a first portion of the prosthetic heart valve moves within the second lumen of the outer dilator and to a collapsed configuration,
the outer sheath configured to be actuated to move the outer sheath distally relative to the inner dilator and relative to the outer dilator such that a second portion of the prosthetic heart valve, distal of the first portion of the prosthetic heart valve, moves within the first lumen of the outer sheath and to a collapsed configuration.

2. The apparatus of claim 1, wherein the first portion of the prosthetic heart valve and the second portion of the prosthetic heart valve collectively form an entirety of the prosthetic heart valve such that the entire prosthetic heart valve is disposed within the outer sheath.

3. The apparatus of claim 1, wherein the handle assembly further includes a first actuator operatively coupled to the inner dilator and a second actuator operatively coupled to the outer sheath, the first actuator configured to move the inner dilator relative to the outer dilator, the second actuator configured to move the outer sheath relative to the inner dilator and relative to the outer dilator.

4. An apparatus, comprising:
a recapture device configured to reposition or remove a prosthetic heart valve deployed within a heart, the recapture device including an outer sheath, an outer dilator, an inner dilator, and a handle assembly,
the outer sheath defining a first lumen,
the outer dilator defining a second lumen and movably disposed at least partially within the first lumen of the outer sheath,
the inner dilator defining a third lumen and movably disposed at least partially within the second lumen of the outer dilator, the inner dilator including a distal tip configured to engage a proximal portion of the prosthetic heart valve,
the handle assembly including an actuator operatively coupled to the inner dilator and operatively coupled to the outer dilator, the handle assembly further including a tether retention mechanism configured to secure a tether extending from the prosthetic heart valve to the handle assembly,
the actuator including a drive mechanism operatively coupled to a first spring coupled to the inner dilator and to a second spring coupled to the outer dilator,
wherein when the actuator is actuated, the inner dilator is configured to move proximally relative to the outer dilator when the tether extending from the prosthetic heart valve is secured to the tether retention mechanism such that a first portion of the prosthetic heart valve is pulled within the second lumen of the outer dilator and moved to a collapsed configuration, and when the outer dilator is actuated after the inner dilator is actuated, the outer dilator is configured to move proximally relative to the outer sheath such that a second portion of the prosthetic heart valve, distal of the first portion of the prosthetic heart valve, is pulled within the first lumen of the outer sheath and moved to a collapsed configuration.

5. The apparatus of claim 4, wherein the first portion of the prosthetic heart valve and the second portion of the prosthetic heart valve collectively include an entirety of the prosthetic heart valve.

6. The apparatus of claim 4, wherein the actuator is further operatively coupled to the tether retention mechanism such that the inner dilator and the tether retention mechanism can be actuated to move together.

7. The apparatus of claim 4, wherein the actuator is further operatively coupled to the tether retention mechanism, the tether retention mechanism including a drive shaft configured to wind the tether into a winding housing as the inner dilator and the outer dilator are actuated.

8. The apparatus of claim 4, wherein the second spring comprises a different spring rate than the first spring.

9. The apparatus of claim 4, wherein the first spring includes a coil spring and the second spring includes a tape spring.

10. The apparatus of claim 4, wherein the first spring includes a coil spring and the second spring includes a coil spring.

11. The apparatus of claim 4, further comprising a release lever coupled to the outer dilator and configured to releasably secure the outer dilator in a fixed position relative to the outer sheath.

12. A method, comprising:
delivering a retrieval device into a heart such that a portion of the retrieval device is positioned adjacent a prosthetic heart valve implanted within the heart, the retrieval device including an inner dilator movably disposed within a lumen of an outer dilator, the outer dilator being disposed at least partially within a lumen of an outer sheath;
inserting a tether extending from the prosthetic heart valve through the lumen of the inner dilator;
securing the tether of the prosthetic heart valve to a tether retention mechanism of the retrieval device;
engaging a distal tip of the inner dilator to a first portion of the prosthetic heart valve; and
actuating the inner dilator to cause the inner dilator to move proximally such that the first portion of the prosthetic heart valve moves within the lumen of the outer dilator and to a collapsed configuration.

13. The method of claim 12, further comprising:
repositioning the prosthetic heart valve; and
actuating the inner dilator, after the prosthetic heart valve has been repositioned, to cause the inner dilator to move distally such that the first portion of the prosthetic heart valve is deployed from the lumen of the outer dilator and moves to an expanded configuration.

14. The method of claim 12, further comprising:
actuating the outer sheath to cause the outer sheath to move distally relative to the outer dilator and the inner dilator such that a second portion of the prosthetic heart valve moves within the lumen of the outer sheath and to a collapsed configuration, the second portion being distal of the first portion of the prosthetic heart valve; and
removing the retrieval device from the heart with the prosthetic heart valve disposed within the lumen of the outer sheath.

15. The method of claim 14, wherein actuating the inner dilator comprises actuating a first actuator disposed on a handle of the retrieval device to move the inner dilator relative to the outer dilator, and actuating the outer sheath comprises actuating a second actuator separate from the first actuator, the second actuator disposed on the handle of the retrieval device, to move the outer sheath relative to the inner dilator and relative to the outer dilator.

16. The method of claim 12, wherein actuating the inner dilator causes the inner dilator and the tether retention mechanism to move together relative to the outer sheath.

17. The method of claim 12, wherein securing the tether of the prosthetic heart valve to the tether retention mechanism comprises piercing the tether with a pinning member.

18. The method of claim 12, further comprising actuating the outer dilator after the inner dilator is actuated, to proximally move the outer dilator relative to the outer sheath such that a second portion of the prosthetic heart valve, distal of the first portion of the prosthetic heart valve, moves within the lumen of the outer sheath to a collapsed configuration.

19. The method of claim 18, further comprising winding the tether into a winding housing as the inner dilator and the outer dilator are actuated.

20. The method of claim 18, further comprising removing the retrieval device from the heart with the prosthetic heart valve completely disposed within the lumen of the outer sheath.

* * * * *